(12) United States Patent
Lin

(10) Patent No.: US 7,081,239 B2
(45) Date of Patent: *Jul. 25, 2006

(54) METHODS FOR MANIPULATING UPPER GASTROINTESTINAL TRANSIT, BLOOD FLOW, AND SATIETY, AND FOR TREATING VISCERAL HYPERALGESIA

(75) Inventor: Henry C. Lin, Manhattan Beach, CA (US)

(73) Assignee: Cedars-Sinai Medical Center Burns and Allen Research Center, Los Angeles, CA (US)

( * ) Notice: Subject to any disclaimer, the term of this patent is extended or adjusted under 35 U.S.C. 154(b) by 29 days.

This patent is subject to a terminal disclaimer.

(21) Appl. No.: 10/810,020

(22) Filed: Mar. 26, 2004

(65) Prior Publication Data

US 2004/0180834 A1    Sep. 16, 2004

Related U.S. Application Data

(60) Division of application No. 09/837,797, filed on Apr. 17, 2001, which is a continuation-in-part of application No. 09/546,119, filed on Apr. 10, 2000, now Pat. No. 6,558,708, and a continuation-in-part of application No. 09/374,143, filed on Aug. 11, 1999, now Pat. No. 6,562,629, and a continuation-in-part of application No. 09/374,142, filed on Aug. 11, 1999, now Pat. No. 6,861,053, said application No. 09/546,119 is a continuation-in-part of application No. 09/420,046, filed on Oct. 18, 1999, now abandoned, which is a continuation-in-part of application No. 09/359,583, filed on Jul. 22, 1999, now abandoned, which is a continuation of application No. 08/832,307, filed on Apr. 3, 1997, now Pat. No. 5,944,175, which is a continuation of application No. 08/442,843, filed on May 17, 1995, now abandoned.

(51) Int. Cl.
*A61K 49/00*    (2006.01)
*A61K 39/00*    (2006.01)
*A61K 35/00*    (2006.01)
*A61K 63/00*    (2006.01)

(52) U.S. Cl. .................. 424/9.2; 424/9.1; 424/116; 424/278.1; 424/439; 426/2; 426/71; 426/658; 426/800; 426/801; 435/4; 435/29

(58) Field of Classification Search ............. 424/9.1, 424/9.2, 116, 278.1, 439; 426/2, 71, 658, 426/800, 801; 435/4, 29

See application file for complete search history.

(56) References Cited

U.S. PATENT DOCUMENTS

| | | |
|---|---|---|
| 4,002,531 A | 1/1977 | Royer |
| 4,160,452 A | 7/1979 | Theeuwes |
| 4,183,960 A | 1/1980 | Asher et al. |
| 4,193,985 A | 3/1980 | Bechgaard et al. |
| 4,256,108 A | 3/1981 | Theeuwes |
| 4,265,874 A | 5/1981 | Bonsen et al. |
| 4,530,838 A | 7/1985 | Evans et al. |
| 4,572,833 A | 2/1986 | Pedersen et al. |
| 4,673,680 A | 6/1987 | Pendleton |
| 4,690,822 A | 9/1987 | Uemura et al. |
| 4,863,744 A | 9/1989 | Urquhart et al. |
| 4,970,207 A | 11/1990 | Sato et al. |
| 4,987,136 A | 1/1991 | Kreek et al. |
| 4,990,617 A | 2/1991 | Boswell et al. |
| 5,041,431 A | 8/1991 | Halskov |
| 5,120,306 A | 6/1992 | Gosselin |
| 5,122,614 A | 6/1992 | Zalipsky |
| 5,219,871 A | 6/1993 | Cross et al. |
| 5,225,352 A | 7/1993 | Zanetta et al. |
| 5,236,901 A | 8/1993 | Burks et al. |
| 5,284,839 A | 2/1994 | Siren et al. |
| 5,308,620 A | 5/1994 | Yen |
| 5,322,697 A | 6/1994 | Meyer |
| 5,349,052 A | 9/1994 | Delgado et al. |
| 5,354,757 A | 10/1994 | Flynn et al. |
| 5,362,756 A | 11/1994 | Riviere et al. |

(Continued)

FOREIGN PATENT DOCUMENTS

EP    0 200 902 A3    11/1986

(Continued)

OTHER PUBLICATIONS

Mei-Huei Chen; Balasubramanian; Murphy; Tabata; Fischer; Chen; Joffe, Sensitive Radioimmunoassay for Measurement of Ci'rculating Peptide YY, Gastroenterology, 1984, pp. 1332-1338, vol. 87, Publisher: American Gastroenterological Association, Published in: Cincinnati, Ohio.

(Continued)

*Primary Examiner*—Rodney P Swartz
(74) *Attorney, Agent, or Firm*—Peter J. Knudsen; Seth D. Levy

(57) ABSTRACT

Disclosed is a method of manipulating the rate of upper gastrointestinal transit of a substance in a mammal. Also disclosed are methods of manipulating satiety and postprandial visceral blood flow. A method of treating visceral pain or visceral hypersensitivity in a human subject is also described. A method for prolonging the residence time of an orally or enterally administered substance by promoting its dissolution, bioavailability and/or absorption in the small intestine is also described. These methods are related to a method of transmitting to and replicating at a second location in the central nervous system a serotonergic neural signal originating at a first location in the proximal or distal gut of a mammal and/or a method of transmitting to and replicating at a second location in the upper gastrointestinal tract a serotonergic neural signal originating at a first location in the proximal or distal gut.

12 Claims, 6 Drawing Sheets

U.S. PATENT DOCUMENTS

| | | |
|---|---|---|
| 5,380,522 A | 1/1995 | Day |
| 5,411,751 A | 5/1995 | Crissinger et al. |
| 5,426,028 A | 6/1995 | Levy et al. |
| 5,428,128 A | 6/1995 | Mensi-Fattohi et al. |
| 5,434,174 A | 7/1995 | Gidda et al. |
| 5,443,826 A | 8/1995 | Borody |
| 5,453,428 A | 9/1995 | Kaminski |
| 5,519,014 A | 5/1996 | Borody |
| 5,538,856 A | 7/1996 | Levy et al. |
| 5,547,961 A | 8/1996 | Ohta et al. |
| 5,550,132 A | 8/1996 | Benson et al. |
| 5,574,010 A | 11/1996 | McFadden |
| 5,589,168 A | 12/1996 | Allen et al. |
| 5,599,795 A | 2/1997 | McCann et al. |
| 5,604,203 A | 2/1997 | Balasubramaniam |
| 5,612,366 A | 3/1997 | Becker et al. |
| 5,616,311 A | 4/1997 | Yen |
| 5,627,200 A | 5/1997 | Kreutter et al. |
| 5,643,575 A | 7/1997 | Martinez et al. |
| 5,645,997 A | 7/1997 | Kline et al. |
| 5,648,355 A | 7/1997 | Theoharides |
| 5,648,359 A | 7/1997 | Ohashi et al. |
| 5,660,828 A | 8/1997 | Rodriguez et al. |
| 5,668,143 A | 9/1997 | Ku et al. |
| 5,677,326 A | 10/1997 | Tsuchiya et al. |
| 5,679,684 A | 10/1997 | Benson et al. |
| 5,684,017 A | 11/1997 | Harrison et al. |
| 5,691,343 A | 11/1997 | Sandborn |
| 5,696,093 A | 12/1997 | Tseng et al. |
| 5,703,100 A | 12/1997 | McDonald et al. |
| 5,707,642 A | 1/1998 | Yue |
| 5,716,643 A | 2/1998 | Yen |
| 5,725,804 A | 3/1998 | Yen |
| 5,726,187 A | 3/1998 | Gaster et al. |
| 5,728,380 A | 3/1998 | Allen et al. |
| 5,736,560 A | 4/1998 | Cosford et al. |
| 5,753,218 A | 5/1998 | Smith et al. |
| 5,753,253 A | 5/1998 | Meyer |
| 5,759,546 A | 6/1998 | Weinberg et al. |
| 5,759,565 A | 6/1998 | Azria et al. |
| 5,776,524 A | 7/1998 | Reinhart |
| 5,780,026 A | 7/1998 | Yoshii et al. |
| 5,821,259 A | 10/1998 | Theoharides |
| 5,830,668 A | 11/1998 | Mordechai et al. |
| 5,833,987 A | 11/1998 | Noelle et al. |
| 5,834,215 A | 11/1998 | Garry et al. |
| 5,846,933 A | 12/1998 | Korngold et al. |
| 5,849,708 A | 12/1998 | Maratos-Flier |
| 5,852,041 A | 12/1998 | Cosford et al. |
| 5,858,403 A | 1/1999 | Borody et al. |
| 5,869,262 A | 2/1999 | Gallatin et al. |
| 5,880,131 A | 3/1999 | Greenwald et al. |
| 5,883,529 A | 3/1999 | Kumata et al. |
| 5,912,227 A | 6/1999 | Croom, Jr. et al. |
| 5,916,869 A | 6/1999 | Croom, Jr. et al. |
| 5,936,092 A | 8/1999 | Shen et al. |
| 5,945,033 A | 8/1999 | Yen |
| 5,968,741 A | 10/1999 | Plevy et al. |
| 5,968,748 A | 10/1999 | Bennett et al. |
| 5,977,175 A | 11/1999 | Lin |
| 5,980,945 A | 11/1999 | Ruiz |
| 6,013,285 A | 1/2000 | Yen |
| 6,013,622 A | 1/2000 | Bruno et al. |
| 6,013,633 A | 1/2000 | Balasubramanium et al. |
| 6,017,879 A | 1/2000 | Mutter et al. |
| 6,040,188 A | 3/2000 | Holman |
| 6,046,167 A | 4/2000 | Balasubramaniam |
| 6,093,692 A | 7/2000 | Shen et al. |
| 6,127,355 A | 10/2000 | Greenwald et al. |
| RE37,020 E | 1/2001 | Lin et al. |
| 6,191,102 B1 | 2/2001 | DiMarchi et al. |
| 6,225,445 B1 | 5/2001 | Shen et al. |
| 6,235,718 B1 | 5/2001 | Balasubramanium et al. |
| 6,264,913 B1 | 7/2001 | Wagner |
| 6,264,988 B1 | 7/2001 | Yen |
| 6,355,478 B1 | 3/2002 | Baez et al. |
| 6,391,343 B1 | 5/2002 | Yen |
| 6,410,707 B1 | 6/2002 | Wagner et al. |
| 6,420,532 B1 | 7/2002 | Gerald et al. |
| 6,447,743 B1 | 9/2002 | Devic et al. |
| 6,558,708 B1 * | 5/2003 | Lin .......................... 424/490 |
| 6,562,629 B1 | 5/2003 | Lin et al. |
| 6,583,111 B1 | 6/2003 | DiMarchi et al. |
| 6,737,408 B1 | 5/2004 | Balasubramanium et al. |
| 2002/0018809 A1 | 2/2002 | Stoll |
| 2002/0068097 A1 | 6/2002 | Basu |
| 2003/0050308 A1 | 3/2003 | Brunner et al. |
| 2003/0124566 A1 | 7/2003 | Kong et al. |
| 2003/0152919 A1 | 8/2003 | Roelens et al. |
| 2003/0185754 A1 | 10/2003 | Cohen et al. |
| 2003/0215421 A1 | 11/2003 | McDonald et al. |
| 2004/0228846 A1 | 11/2004 | Pang et al. |

FOREIGN PATENT DOCUMENTS

| | | |
|---|---|---|
| EP | 0 349 949 | 7/1989 |
| EP | 0 401 384 A1 | 12/1990 |
| EP | 0 539 319 A2 | 4/1993 |
| EP | 0 955 314 A2 | 11/1999 |
| EP | 1 288 223 A1 | 3/2003 |
| EP | 1 288 224 A1 | 3/2003 |
| EP | 0 678 018 B1 | 4/2003 |
| EP | 1 051 194 B1 | 5/2003 |
| EP | 1 468 610 A1 | 10/2004 |
| FR | 2 769 915 | 4/1999 |
| JP | 60007934 | 1/1985 |
| WO | WO 93/19175 A1 | 9/1993 |
| WO | WO 94/03380 | 3/1994 |
| WO | WO 94/22467 | 10/1994 |
| WO | WO 95/06058 A1 | 3/1995 |
| WO | WO 96/22783 | 8/1996 |
| WO | WO 96/18374 | 11/1996 |
| WO | WO 98/20885 | 5/1998 |
| WO | WO 98/32466 A1 | 7/1998 |
| WO | WO 98/46997 | 10/1998 |
| WO | WO 98/56397 | 12/1998 |
| WO | WO 99/02135 | 1/1999 |
| WO | WO 85/02840 | 7/1999 |
| WO | WO 99/43707 A1 | 9/1999 |
| WO | WO 00/34236 A1 | 6/2000 |
| WO | WO 00/42026 A1 | 7/2000 |
| WO | WO 00/47219 | 8/2000 |
| WO | WO 00/59887 | 10/2000 |
| WO | WO 00/68197 | 11/2000 |
| WO | WO 00/78333 A2 | 12/2000 |
| WO | WO 01/04156 A1 | 1/2001 |
| WO | WO 01/14368 A1 | 3/2001 |
| WO | WO 01/14386 A1 | 3/2001 |
| WO | WO 01/35988 A1 | 5/2001 |
| WO | WO 01/51078 A1 | 7/2001 |
| WO | WO 01/66135 A1 | 9/2001 |
| WO | WO 01/76831 A2 | 10/2001 |
| WO | WO 01/89554 A2 | 11/2001 |
| WO | WO 02/03978 A2 | 1/2002 |
| WO | WO 02/47712 | 6/2002 |
| WO | WO 02/066479 A1 | 8/2002 |
| WO | WO 02/067918 A1 | 9/2002 |
| WO | WO 03/026591 | 4/2003 |
| WO | WO 03/057235 | 7/2003 |
| WO | WO 03/105763 | 12/2003 |

OTHER PUBLICATIONS

Morley, John E.; Levine, Allen S.; Grace, Martha; Kneip, Julie, "Peptide YY (PYY), a potent orexigenic agent," Brain Research, 1985, vol. 341, pp. 200-203. Elsevier Science Publishers.

John E. Morley and James F. Flood, An Investigation of Tolerance to the actions of Leptogenic and Anorexigenic Drugs in Mice, Life Sciences, Sep. 10, 1987, pp. 22157-22165, vol. 41, Publisher. Pergamon Journals, Published in: Sepulveda, CA, US.

Kazuhiko Tatemoto; Nakano; Makk; Angwin; Mann; Schilling; Go, Isolation and Primary Structure of Human Peptide YY, Biochemical and Biophysical Research Communications, Oct. 31, 1988, pp. 713-717, vol. 157(2), Publisher: Academic Press, Inc., Published in: Los Angeles, California, US.

Balasubramaniam, A.; Servin, A. L.; Rigel, D. F.; Rouyer-Fessard, C. R.; Laburthe, M, Syntheses and receptor affinities of partial sequences of peptide YY (PYY) Peptide. Research., date- 1988, vol. 1, No. 1, pp. 32-35.

John E. Morley, An approach to the development of drugs for appetite discorders, Neuropsychobiology , Date 1989, vol. 21, issue 1, pp. 22-30, Karger AG, Basel.

Eberlein, G. A.;Eysselein, V. E.;Schaeffer, M.; Layer, P.;Grandt, D.;Goebell, H.;Niebel, W.;Davis, M.;Lee, T.D.; Shively,J. E.; Reeve, J. R., Jr.; A new molecular form of PYY: structural Characterization of human PYY(3-36) and PYY(1-36) Peptides, Date- 1989, vol. 10, No. 4, pp. 797-803, Pergamon Press, US.

Eysselein, V. E.;Eberlein, G. A.;Grandt, D.;Schaeffer, M.;Zehres, B.; Behn, U.;Schaefer, D.; Goebell, H.;Davis, M.; Lee,T. D.; Shively, J. E.; Meyer, H. E.; Reeve, J. R., Jr, Structural characterization of canine PYY, Peptides, Jun. 15, 1989, vol. 11, pp. 111-116, Pergamon Press, US.

Hiroyuki Minakata, Takashi Iwashita, Synthesis of analogues of peptide YY with modified N-terminal regions: relationships of amphiphilic secondary structures and activity in rat vas deferens, Journal: Biopolymers, vol. 29, Jan. 29, 1990, pp. 61-67, John Wiley & Sons, Inc.

Ramo, O. J.; Balasubramaniam, A.; Sheriff, S.; Rogers, D. H.; McCullough, P. J.; Bell, R. H., Jr., Neuropeptide Y and peptide YY stimulate the growth of exocrine pancreatic carcinoma cells, Neuropeptides, 1990, vol. 15, pp. 101-106, Longman Group UK.

S.F. Leibowitz, J.T. Alexander, Analysis of Neuropeptide Y-Induced Feeding: Dissociation of Y1 and Y2 Receptor Effects on Natural Meal Patterns, Peptides, Jul. 25, 1991, pp. 1251-1260, vol. 12, Publisher. Pergamon Press, Published in: New York NY, US.

Inui Akio, Minoru Okita, Masaharu Nakajima, Toru Inoue, Noriaki Sakatani, Manabu Oya, Hideki Morioka, Yasuhiko Okimura, Kazuo Chihara, and Shigeaki Baba, Neuropeptide regulation of feeding in dogs, Neuropeptides and Food Intake, 1991, pp. R5888-R594, 0363-6119, The American Physiological Society.

Grandt, D.; Teyssen, S.; Schimiczek, M.; Reeve, J. R., Jr.; Feth, F.; Rascher, W.; Hirche, H.; Singer, M. V.; Layer, P.; Goebell, H.; Ho, F.J.; Eysselein, V.E.: Novel generation of hormone receptor specificity by amino terminal processing of peptide YY, Biochemical and Biophysical Research Communications, Aug. 14, 1992, vol. 186, No. 3, pp. 1299-1306, Academic Press, Inc.

S. Okada, Ohshima, Mori, K. Tatemoto, Peripherally not Centrally Administered Peptide YY(PYY) Decreases High Fat Diet Intake, Jun. 9, 1993, vol. 520, Publisher; Endocrinology , Published in: Gunmo, Japan.

Grandt, D.; Schimiczek, M.; Struk, K.; shively, J.; Eysselein, V. E.; Goebell, H.; Reeve, J. R., JR—Characterization of two forms of peptide YY, PYY(1-36) and PYY(3-36), in the rabbit, Peptides, Jul. 29, 1994, vol. 15, No. 5, pp. 815-820, Pergamon, Elsevier Science Ltd, US.

Dumont, Yvan.; Cadieux, Alain.; Pheng, L. H.; Fournier, A.; St Pierre, S.; Quirion, R., Peptide YY derivatives as selective neuropeptide Y/peptide YY $Y^1$ and $Y^2$ agonists devoided of activity for the $Y^3$ receptor sub-type, Brain Research.Molecular.Brain Research,—Jun. 28, 1994, vol. 26, No. 1-2, pp. 320-324, Elsevier Science B.V.

Margaret Dos Santos Medeiros, M. D.; Anthony J. Turner, Processing and metabolism of peptide-YY: pivotal roles of dipeptidylpeptidase-IV, aminopeptidase-P, and endopeptidase-24.11, Endocrinology 1994, Vo 134, No. 5, pp. 2088-2094, The Endocrine Society, US.

Grandt, D.; Schimiczek, M.; Beglinger, C.; Layer, P.; Goebell, H.; Eysselein, V. E.; Reeve, J. R., JR, Two molecular forms of peptide YY (PYY) are abundant in human blood: characterization of a radioimmunoassay recognizing PYY 1-36 and PYY 3-36, Regulatory Peptides, May 5, 1994, vol. 51, No. 2, pp. 151-159, Elsevier Sciences B.V.

Kazuhiko Tatemono, New Developments in Research on digestive tract hormones, Progress in Medicine, vol. 15, No. 9, date Sep. 1995, pp. 1793-1804, 46$^{th}$ Pepsin Research Meeting (translated from Japanese) JP.

Norio Tani, Digestive Tract Hormones, digestive Tract, 1996, Article Serial No.: 0012 (translated from Japanese) JP.

Gue, M.; Junien, J. L.; Reeve, J. R., Jr.; Rivier, J.; Grandt, D.; Tache, Y. Reversal by NPY, PYY and 3-36 Molecular forms of NPY and PYY of intracisternal CRF-induced inhibition of gastric acid secretion in rats, British Journal of Pharmacology, May 1996, pp. 118(2), 237-242, Stockton Press.

Kazuhiko Tatemoto, Chemical and clinical Applications of Digestive Tract hormones, Digestive Tract hormones, 1994, pp. 38-45, vol. 2, No. 4, G. I. Research (translated Japanese article) JP.

Chen, C.H.; Stephens, R. L., Jr.; Rogers, R. C. PYY and NPY: control of gastric motility via action on Y1 and Y2 receptors in the DVC, Neurogastroenterol.Motil. 1997, pp. 109-116, vol. 9, Blackwell Science Ltd., US.

Xiao, Q.; Han, X.; Arany, E.; Hill, D.; Challis, J. R.; McDonald, T. J, Human placenta and fetal membranes contain peptide YY1-36 and peptide YY3-36, Journal of Enocrinology, 1998, pp. 485-492, vol. 156, Journal of Endocinology Ltd, UK.

Naruto yamawaki, Yasuaki Okamoto, Is there a biological case for eating disorders?. From the perspective of neurochemistry, Brian Science, 1998, pp. 29-36, Article Serial No. 0003, vol. 20, Special Edition (Eating Disorders and Obesity) Think also presented at conference Apr. 24, 1998 at Showa University, Yokohama, Japan (translated Japanese article) JP.

Noboru Yanaihara , VIP, PYY and Others , All About Hormone Illustrated No. 381, 1998, p. 382-387, Article Serial No. 0033, vol. 46, VI. Gastrointestinal Hormones, (translated Japanese article) JP.

Kazuhiko Tatemoto, Development of Neuropeptide Y Receptor Antagonists, Research on Biologically Active Substances, Research Papers of the Suzuken Memorial Foundation, vol. 14, p. 243-244 (translated Japanese article) JP.

David A. Keire, Mitsuo Kobayashi, Travis E. Solomon, Joseph R. Reeve, Jr., Solution structure of monomeric peptide YY supports the functional significance of the PP-Fold, Biochemistry 2000, pp. 9935-9942, Nov. 8, 1999, American Chemical Society, published on web Jul. 21, 2000, US.

Philippe Naveilhan, Hessameh Hassani, Josep M. Canals, A. Jonas Ekstrand, ASA Larefalk, Vijay Chhajlani, Ernest Arenas, Karin Gedda, Lennart Svensson, Peter Thoren, and Patrik Ernfors, Normal feeding behavior, body weight and leptin response require the neuropeptide Y Y2 receptor, Nature America Inc. Oct. 1999, pp. 1188-1193, vol. 5, No. 10, Nature Medicine.

Akihiro Asakawa, Akio Inui, Naohiko Ueno, Mineko Fujimiya, Masayuki A. Fujino, Masato Kasuga, Mouse pancreatic polypeptide modulated food intake, while not influencing anxiety in mice, Peptides, 1999, pp. 1445-1448, vol. 20, Elsevier Science Inc.

Keire, D. A.; Mannon P.; Kobayashi, M.; Walsh, J. H.; Solomon, T. E.; Reeve, J. R., Jr., Primary structures of PYY, [Pro$^{34}$]PYY, and PYY-(3-36) confer different conformations and receptor selectivity, Am.J.Physiol Gastrointest.Liver Physiol, Feb. 1, 2000, p. G126-G131, vol. 279.

Rachel L. Batterham, Michael A. Cowley, Caroline S. Small, Herbert Herzog, Mark A. Cohen, Catherine L. Dakin, Alison M. Wren, Audrey E. Brynes, Malcom J. Low, Mohammad A Ghatei, Roger D. Cone, Stephen R. Bloom. "Gut hormone PYY3-36 physiologically inhibits food intake," Nature, 2002, vol. 418, pp. 650-654, Nature Publishing Group.

Herbert Herzog, Hypothalamic Y2 Receptors: Central Coordination of Energy Homeostasis and Bone Mass Regulation, Drug News Perspect. Oct. 2002, pp. 506-510, vol. 15 (8), Prous Science.

Batterham, Rachel. L.; Cohen, Mark. A.; Ellis, Sandra, M.; Le Roux, Carel. W.; Withers, Dominic, J.; Frost, Gary. S.; Ghatei, M. A.; Bloom, S. R., Inhibition of food intake in obese subjects by peptide YY3-36, The New.England.Journal of Medicine, Date- Sep. 4, 2003, pp. 941-948, vol. 349.

Rachel L. Batterham, Stephen R. Bloom,. The gut hormone peptide YY regulates appetite , N.Y.Academy.of Sciences, 2003, pp. 162-168, vol. 994.

R. L. Batterham, C.W. Le Roux, M.A. Choen, A.J. Park, S.M. Ellis, M. Patterson, G.S. Frost, M.A.Ghatei and S.R. Bloom, Pancreatic polypeptide reduces appetite and food intake in humans, The Journal of Clinical Endocrinology and Metobolism, 2003, pp. 3989-3992, vol. 88(8), the Endocrine Society, US.

Abuchowski, A.; Kazo, G.M.; Verhoest, C. R., Jr.; Van, ES T.; Kafkewitz, D.; Nucci, M. L.; Viau, A. T.; and Davis, F. F.; "Cancer Therapy With Chemically Modified Enzymes. I. Antitumor Properties of Polyethylene Glycol-Asparaginase Conjugates;" *Cancer Biochem. Biophys.*; Jun. 1984; 7 (2); 175-186.

Barlow, S. E. and Dietz, W. H.; "Obesity Evaluation and Treatment: Expert Committee Recommendations. The Material and Child Health Bureau, Health Resources and Services Administration and the Department of Health and Human Services;" *Pediatrics*; Sep. 1998; 102 (3); E29.

Caliceti, P.; Schiavon, O.; and Veronese, F. M.; "Biopharmaceutical Properties of Uricase Conjugated to Neutral and Amphiphilic Polymers;" *Bioconjug. Chem.*; Jul. 1999; 10 (4); 638-646.

Chelikani, P. K.; Haver, A. C.; and Reidelberger, R. D.; "Intravenous Infusion of Peptide YY(3-36) Potently Inhibits Food Intake in Rats;" *Endocrinology*; Feb. 2005; 146 (2); 879-888.

Clapham, J.C.; Arch, J.R.S.; Tadayyon, M.; "Anti-obesity drugs; a critical review of current therapies and future opportunities;" *Pharmacology and Therapeutics*; 2001; vol. 89; 81-121.

Cox, J. E. and Randich, A.; "Enhancement of Feeding Suppression by PYY(3-36) in Rats With Area Postrema Ablations 1;" *Peptides*; Jun. 2004; 25 (6); 985-989.

Delgado, C.; Francis, G. E.; and Fisher, D.; "The Uses and Properties of PEG-Linked Proteins;" *Crit Rev. Ther. Drug Carrier Syst.*; 1992; 9 (3-4); 249-304.

Dreborg, S. and Akerblom, E. B.; "Immunotherapy With Monomethoxypolyethylene Glycol Modified Allergens;" *Crit Rev. Ther. Drug Carrier Syst.*; 1990; 6 (4); 315-365.

Eng, J.; Kleinman, W. A.; Singh, L.; Singh, G.; and Raufman, J. P.; "Isolation and Characterization of Exendein-4, an Exendin-3 Analogue, From Heloderma Suspectrum Venom. Further Evicence for an Exendin Receptor on Dispersed Acini From Guinea Pig Pancreas;" *J. Biol. Chem.*; Apr. 1992; 267 (11); 7402-7405.

Francis, G. E.; Fisher, D.; Delgado, C.; Malik, F.; Gardiner, A.; and Neale, D.; "PEGylation of Cytokines and Other Therapeutic Proteins and Peptides: the Importance of Biological Optimisation of Coupling Techniques;" *Int. J. Hematol.*; Jul. 1998; 68 (1); 1-18.

Jëquier, E.; "Energy, obesity and body weight standards;" *Am. J. Clin. Nutr.*; 45; 1035-1047.

Kenchaiah, S.; Evans, J. C.; Levy, D.; Wilson, P. W.; Benjamin, E. J.; Larson, M. G.; Kannel, W. B.; and Vasan, R. S.; "Obesity and the Risk of Heart Failure;" *N. Engl. J. Med.*; Aug. 2002; 347 (5); 305-313.

Kopelman, P. G.; "Obesity As a Medical Problem;" *Nature*; Apr. 2000; 404 (6778); 635-643.

Langer, R.; "New Methods of Drug Delivery;" *Science*; Sep. 1990; 249 (4976); 1527-1533.

Malik, F.; Delgado, C.; Knusli, C.; Irvine, A. E.; Fisher, D.; and Francis, G. E.; "Polyethylene Glycol (PEG)-Modified Granulocyte-Macrophage Colony-Stimulating Factor (GM-CSF) With Conserved Biological Activity;" *Exp. Hematol.*; Sep. 1992; 20 (8): 1028-1035.

Massie, B. M.; "Obesity and Heart Failure—Risk Factor or Mechanism?;" *N. Engl. J. Med.*; Aug. 2002; 347 (5); 358-359.

McGowan, B. and Bloom, S.; "Peptide YY and Appetite Control 1;" *Curr. Opin. Pharmacol*; Dec. 2004; 4 (6); 583-588.

Moran, Timothy H.; Smedh, Ulrika; Kinzig, Kimberly P.; Scott, Karen A.; Knipp, Susan; and Ladenheim, Ellen E.; "Peptide YY (3-36) Inhibits Gastric Emptying and Produces Acute Reductions in Food Intake in Rhesus Monkeys;" *AJP—Regulatory, Integrative and Comparative Physiology*; Sep. 2004: 00535-.

Morpurgo, M.; Schiavon, O.; Caliceti, P.; and Veronese, F. M.; "Covalent Modification of Mushroom Tyrosinase With Different Amphiphic Polymers for Pharmaceutical and Biocatalysis Applications;" *Appl. Biochem. Biotechnol.*; Jan. 1996; 56 (1): 59-72.

Pittner, R. A.; Moore, C. X.: Bhavsar, S. P.: Gedulin, B. R.; Smith, P. A.; Jodka, C. M.; Parkes, D. G.; Paterniti, J. R.; Srivastava, V. P.; and Young, A. A.; "Effects of PYY[3-36] in Rodent Models of diabetes and Obesity 1;" *Int. J Obes. Relat Metab Disord.*; Aug. 2004; 28 (8); 963-971.

Rissanen, A.; Heliovaara, M.; Knekt, P.; Reunanen, A.; Aromaa, A.; and Maatela, J.; "Risk of Disability and Mortality Due to Overweight in a Finnish Propulation;" *BMJ*; Oct. 1990; 301 (6756); 835-837.

Rossi, M. and Bloom, S.R.; "Central Nervous System Neuropeptides Involved in Obesity;" *Handbook of Experimental Pharmacology*; 149; 313-341.

Schutz, Y.; Bessard, T.; and Jequier, E.; "Exercise and Postprandial Thermogenesis in Obese Women Before and After Weight Loss;" *Am. J. Clin. Nutr.*; Jun. 1987; 45 (6); 1424-1432.

Verma, I. M.; Deschamps, J.: Van, Beveren C.; and Sassone-Corsi, P.; "Human Fos Gene;" *Cold Spring Harb. Symp. Quant. Biol.*; 1986; 51 Pt 2 949-958.

Vorobjev, P. E.; Zarytova, V.F.; and Bonora, G. M.; "Oligonucleotide Conjugated to Linear and Branched high Molecular Weight Polyethylene Glycol As Substrates for RNase H;" *Nucleosides Nucleotides*; Nov. 1999; 18 (11-12); 2745-2750.

Walker, M. W.; Ewald, D. A.; Perney, T. M.; and Miller, R. J.; "Neuropeptide Y Modulates Neurotransmitter Release and Ca2+ Currents in Rat Sensory Neurons;" *J. Neurosci.*; Jul. 1988; 8 (7); 2438-2446.

Wang, Y.J. and Hanson, M.A.; "Parenteral Formulations of Proteins and Peptides: Stability and Stabilizers;" *J. Paren. Sci. & Tech.*; 1988; 42; S1-S24.

Casafont Morencos, F.; De Las Heras Castano, G.; Martin Ramos, L.; Lopez Arias, M. J.; Ledesma, F.; and Pons Romero, F.; "Small Bowel Bacterial Overgrowth in Patients With Alcoholic Cirrhosis;" *Digestive Diseases and Sciences*; Jun. 1995; 40 (6); 1252-1256.

Alander, M.; De, Smet, I; Nollet, L.; Verstraete, W.; Von, Wright A.; and Mattila-Sandholm, T.; "The Effect of Probiotic Strains on the Microbiota of the Simulator of the Human Intestinal Microbial Ecosystem (SHIME);" *Int. J Food Microbiol.*; Jan. 1999; 46 (1); 71-79: Abstract Only.

Albano,S.A. et al; "Small Intestinal Bacterial Overgrowth in Systemic Lupus Erythematosus (SLE);" *Arthritis & Rheumatism*; Nov. 1999; 42(9 Suppl.); S305; Abstract 1409a.

Alpert, J. E.; Maddocks, A.: Nierenberg, A. A.; O'Sullivan, R.; Pava, J. A.; Worthington, J. J., III; Biederman, J.; Rosenbaum, J. F.; and Fava, M.; "Attention Deficit Hyperactivity Disorder in Childhood Among Adults With Major Depression;" *Psychiatry Res.*; Jun. 1996; 62 (3); 213-219; Abstract Only.

Anderson, B. W.; Kneip, J. M.; Levine, A. S.; and Levitt, M. D.; "Influence of Infusate Viscosity on Intestinal Absorption in the Rat. An Explanation of Previous Discrepant Results;" *Gastroenterology*; Oct. 1989; 97 (4); 938-943.

Annese, V.; Bassotti, G.; Napolitano, G.; Usai, P.; Andriulli, A.; and Vantrappen, G.; "Gastrointestinal Motility Disorders in Patients With Inactive Crohn's Disease;" *Scand. J Gastroenterol.*; Nov. 1997; 32 (11); 1107-1117; Abstract Only.

Asarian, L.; Corp, E. S.; Hrupka, B.; and Geary, N.; "Intracerebroventricular Glucagon-Like Peptide-1 (7-36) Amide Inhibits Sham Feeding In Rats Without Eliciting Satiety; " *Physiol Behav.*; Jun. 1998; 64 (3); 367-372; Abstract Only.

Autschbach, F.; Braunstein, J.; Helmke, B.; Zuna, I.; Schurmann, G.; Niemir, Z. I.; Wallich, R.; Otto, H. F.; and Meuer, S. C.; "In Situ Expression of Interleukin-10 in Noninflamed Human Gut and in Inflammatory Bowel Disease;" *Am J Pathol.*; Jul. 1998; 153 (1); 121-130; Abstract Only.

Babyatsky, M. W.; Rossiter, G.; and Podolsky, D. K.; "Expression of Transforming Growth Factors Alpha and Beta in Colonic Mucosa in Inflammatory Bowel Diseases;" *Gastroenterology*; Apr. 1996; 110 (4); 975-984; Abstract Only.

Bagnol, D.; Mansour, A.; Akil, H.; and Watson, S. J.; "Cellular Localization and Distribution of the Cloned Mu and Kappa Opioid Receptors in Rat Gastrointestinal Tract;" *Neuroscience*; Nov. 1997; 81 (2); 579-591; Abstract Only.

Barnes, R. M.; Allan, S.; Taylor-Robinson, C. H.; Finn, R.; and Johnson, P. M.; "Serum Antibodies Reactive With *Saccharomyces cerevisiae* in Inflammatory Bowel Disease: Is IgA Antibody a Marker for Crohn's Disease?;" *Int. Arch. Allergy Appl. Immunol.*; 1990; 92 (1); 9-15.

Bartlett, J. G.; "Treatment of Antibiotic-Associated Pseudomembranous Colitis;" *Rev Infect Dis*; 1984; 6 (Suppl 1); S235-S241.

Baskin, D. G.; Hahn, T. M.; and Schwartz, M. W.; "Leptin Sensitive Neurons in the Hypothalamus;" *Horm. Metab Res.*; May 1999; 31 (5); 345-350; Abstract Only.

Bell, I. R.; Baldwin, C. M.; and Schwartz, G. E.; "Illness Form Low Levels of Environmental Chemicals: Relevance to Chronic Fatigue Syndrome and Fibromyalgia;" *Am J Med.*; Sep. 1998; 105 (3A); 74S-82S.

Bennett, G.; Al-Rashed, S.; Hoult, J. R.; and Brain, S. D.; "Nerve Growth Factor Induced Hyperalgesia in the Rat Hind Paw Is Dependent on Circulating Neutrophils;" *Pain*; Sep. 1998; 77 (3); 315-322.

Bergstrom, J.; "Mechanisms of Uremic Suppression of Appetite;" *J Ren Nutr.*; Jul. 1999: 9 (3); 129-132; Abstract Only.

Bilchik, A. J.; Hines, O. J.; Zinner, M. J.; Adrian, T. E.; Berger, J. J.; Ashley, S. W.; and McFadden, D. W.; "Peptide YY Augments Postprandial Small Intestinal Absorption in the Conscious Dog 1;" *Am. J Surg.*; Jun. 1994; 167 (6); 570-574.

Bjornsson, E. S. and Abrahamsson, H.; "Comparison Between Physiologic and Erythromycin-Induced Interdigestive Motility;" *Scand. J Gastroenterol.*; Feb. 1995; 30 (2); 139-145; Abstract Only.

Blevins, J. E.; Stanley, B. G.; and Reidelberger, R. D.; "Brain Regions Where Cholecystokinin Suppresses Feeding in Rats;" *Brain Res.*; Mar. 2000; 860 (1-2); 1-10.

Booyse, F. M.; Osikowicz, G.; and Quarfoot, A. J.; "Effects of Chronic Oral Consumption of Nicotine on the Rabbit Aortic Endothelium;" *Am J Pathol.*; Feb. 1981; 102 I2); 229-238.

Brown, Michael S. and Goldstein, Joseph S.; "The Hyperlipoproteinemias and Other Disorders of Lipid Metabolism;" 1994; 13 (344); 2058-2069.

Brown, N. J.; Read, N. W.; Richardson, A.; Rumsey, R. D.; and Bogentoft, C.; "Characteristics of Lipid Substances Activating the Ileal Brake in the Rat;" *Gut*; Oct. 1990; 31 (10); 1126-1129.

Brown, N. J.; French, S. J.; Rumsey, R. D.; and Read, N. W.; "The Effect of a 5-HT3-Antagonist on the Ileal Brake Mechanism in the Rat;" *J Pharm. Pharmacol.*; Jul. 1991; 43 (7); 517-519; Abstract Only.

Brown, N. J.; Rumsey, R. D.; Bogentoft, C.; and Read, N. W.; "The Effect of an Opiate Receptor Antagonist on the Ileal Brake Mechanism in the Rat," *Pharmacology*; Oct. 1993; 47 (4); 230-236; Abstract Only.

Brown, N. J.; Horton, A.; Rumsey, R. D.; and Read, N. W.; "Granisetron and Ondansetron: Effects on the Ileal Brake Mechanism in the Rat;" *J Pharm. Pharmacol.*; Jun. 1993; 45 (6); 521-524; Abstract Only.

Bruin, K. F.; Hommes, D. W.; Jansen, J.; Tytgat, G. N.; Wouter Ten, Cate J.; and Van Deventer, S. J.; "Modulation of Cytokine Release From Human Monocytes by Drugs Used in the Therapy of Inflammatory Bowel Diseases;" *Eur. J. Gastroenterol. Hepatol.*; Aug. 1995; 7 (8); 791-795; Abstract Only.

Bruno, R. L.; Creange, S. J.; and Frick, N. M.; "Parallels Between Post-Polio Fatigue and Chronic Fatigue Syndrome: a Common Pathophysiology?;" *Am J Med.*; Sep. 1998; 105 (3A); 66S-73S.

Buhner, S. and Ehrlein, H. J.; "Characteristics of Postprandial Duodenal Motor Patterns in Dogs;" *Dig. Dis. Sci.*; Dec. 1989; 34 (12); 1873-1881.

Bushnik, T.; Bielajew, C.; Konkle, A. T.; and Merali, Z.; "Influence of Bombesin on Threshold for Feeding and Reward in the Rat;" *Acta Neurobiol. Exp. (Wars.)*; 1999; 59 (4); 295-302; Abstract Only.

Cammack, J.; Read, N. W.; Cann, P. A.; Greenwood, B.; and Holgate, A. M.; "Effect of Prolonged Exercise on the Passage of a Solid Meal Through the Stomach and Small Intestine;" *Gut*; Nov. 1982; 23 (11); 957-961.

Camoglio, L.; Te Velde, A. A.; Tigges, A. J.; Das, P. K.; and Van Deventer, S. J.; "Altered Expression of Interferon-Gamma and Interleukin-4 In Inflammatory Bowel Disease;" *Inflamm. Bowel. Dis.*; Nov. 1998; 4 (4); 285-290; Abstract Only.

Carlson, G. M.; Ruddon, R. W.; Hug, C. C., Jr.; and Bass, P.; "Effects of Nicotine on Gastric Antral and Duodenal Contractile Activity in the Dog;" *J Pharmacol. Exp. Ther.*; Apr. 1970; 172 (2); 367-376.

Casafont Morencos, F.; De Las Heras, Castano G.; Martin, Ramos L.; Lopez Arias, M. J.; Ledesma, F.; and Pons, Romero F.; "Small bowel Bacterial Overgrowth in Patients With Alcoholic Cirrhosis;" *Dig. Dis. Sci.*; Mar. 1996; 41 (3); 552-556; Abstract Only.

Casellas, F.; Chicharro, L.; and malagelada, J. R.; "Potential Usefulness of Hydrogen Breath Test With D-Xylose in Clinical Management of Intestinal Malabsorption;" *Dig. Dis. Sci.*, Feb. 1993; 38 (2); 321-327.

Casini-Raggi, V.; Kam, L.; Chong, Y. J.; Fiocchi, C.; Pizarro, T. T.; and Cominelli, F.; "Mucosal Imbalance of IL-1 and IL-1 Receptor Antagonist in Inflammatory Bowel Disease. A Novel Mechanism of Chronic Intestinal Inflammation;" *J Immunol.*; Mar. 1995; 154 (5); 2434-2440; Abstract Only.

Castedal, M.; Bjornsson, E.; and Abrahamsson, H.; "Postprandial Peristalsis in the Human Duodenum;" *Neurogastroenterol. Motil.*; Jun. 1998; 10 (3); 227-233; Abstract Only.

Cater, R. E.; "The Clinical Importance of Hypochlorhydria (a Consequence of Chronic Helicobacter Infection): Its Possible Etiological Role in Mineral and Amino Acid Malabsorption, Depression, and Other Syndromes;" *Med. Hypotheses*; Dec. 1992; 39 (4); 375-383.

Chang, C. S.; Chen, G. H.; Kao, C. H.; Wang, S. J.; Peng, S. N.; Huang, C. K.; and Poon, S. K.; "Increased Accuracy of the Carbon–D-Xylose Breath Test in Detecting Small-Intestinal Bacterial Overgrowth by Correction With the Gastric Emptying Rate;" *Eur. J Nucl. Med.*; Oct. 1995; 22 (10); 1118-1122; Abstract Only.

Chang, C. S.; Chen, G. H.; Lien, H. C.; and Yeh, H. Z.; "Small Intestine Dysmotility and Bacterial Overgrowth in Cirrhotic Patients With Spontaneous Bacterial Peritonitis;" *Hepatology*; Nov. 1998; 28 (5); 1187-1190; Abstract Only.

Chen, J. X.; Pan, H.; Rothman, T. P.; Wade, P. R.; and Gershon, M. D.; "Guinea Pig 5-HT Transporter: Cloning, Expression, Distribution, and Function in Intestinal Sensory Reception;" *Am J Physiol*; Sep. 1998; 275 (3 Pt 1); (3 Pt 1); G433-G448; Abstract Only.

Cherbut, C.; Aube, A. C.; Blottiere, H. M.; and Galmiche, J. P.; "Effects of Short-Chain Fatty Acids on Gastrointestinal Motility;" *Scand. J Gastroenterol. Suppl*; 1997; 222 58-61; Abstract Only.

Chesta, J.: Defilippi, C.; and Defilippi, C.; "Abnormalities in Proximal Small Bowel Motility in Patients With Cirrhosis;" *Hepatology*; May 1993; 17 (5); 828-832; Abstract Only.

Christophe, J.; "Is There Appetite After GLP-1 and PACAP?;" *Ann. N. Y. Acad. Sci.*; Dec. 1998; 865 323-335; Abstract Only.

Cohn, C.; "Meal-Eating, Nibbling, and Body Metabolism;" *J Am Diet. Assoc.*; May 1961; 38 433-436.

Cohn, C.; "Feeding Patterns and Some Aspects of Cholesterol Metabolism;" *Fed. Proc.*; Jan. 1964; 23 76-81.

Collins, S. M.; Conover, K. L.; Forsyth, P. A.; and Weingarten, H. P.; "Endogenous Cholecystokinin and Intestinal Satiety;" *Am J Physiol*; Dec. 1985; 249 (6 Pt 2); R667-R671; Abstract Only.

Cominelli, F. and Pizarro, T. T.; "Interleukin-1 and Interleukin-1 Receptor Antagonist in Inflammatory Bowel Disease;" *Aliment. Pharmacol. Ther.*; 1996; 10 Suppl 2 49-53; Abstract Only.

Corazza, G.: Strocchi, A.; Sorge, M.; Bentai, G.; and Gasbarrini, G.; "Prevalence and Consistency of Low Breath H2 Excretion Following Lactulose Ingestion. Possible Implications for the Clinical Use of the H2 Breath Test;" *Dig. Dis. Sci.*; Nov. 1993; 38 (11); 2010-2016; Abstract Only.

Corazza, G. R.; Menozzi, M. G.; Strocchi, A.; Rasciti, L.; Vaira, D.; Lecchini, R.; Avanzini, P.; Chezzi, C.; and Gasbarrini, G.; "The Diagnosis of Small Bowel Bacterial Overgrowth. Reliability of Jejunal Culture and Inadequacy of Breath Hydrogen Testing;" *Gastroenterology*; Feb. 1990; 98 (2); 302-309; Abstract Only.

Costello,A.J.; "The Effect of an Elemental Diet on Stool Output in Irritable Bowel Syndrome," *Proceedings of the Nutrition Society*; 1994; 53 (3), 223A.

Cross-Mellor, S. K.; Kavaliers, M.; and Ossenkopp, K. P.; "Repeated Injfections of Lipopolysaccharide Attenuate the Satiety Effects of Cholecystokinin;" *Neuroreport*; Dec. 1999; 10 (18); 3847-3851; Abstract Only.

Culpepper-Morgan, J. A.; Inturrisi, C. E.; Portenoy, R. K.; Foley, K.; Houde, R. W.; Marsh, F.; and Kreek, M. J.; "Treatment of Opioid-Induced Constipation With Oral Naloxone: a Pilot Study;" *Clin Pharmacol. Ther.*; Jul. 1992; 52 (1); 80-95; Abstract Only.

Cummings, J. H. and Macfarlane, G. T.; "The Control and Consequences of Bacterial Fermentation in the Human Colon;" *J Appl. Bacteriol.*; Jun. 1991; 70 (6); 443-459.

Cunningham, K. M.; Daly, J.; Horowitz, M.; and Read, N. W.; "Gastrointestinal Adaptation to Diets of Differing Fat Composition in Human Volunteers;" *Gut*; May 1991; 32 (5); 483-486.

Cuoco, L.; Cammarota, G.; Jorizzo, R.; and Gasbarrini, G.; "Small Intestinal Bacterial overgrowth and Symptoms of Irritable Bowel Syndrome;" *Am J Gastroenterol.*; Jul. 2001; 96(7); 2281-2282.

Daig, R.; Andus, T.; Aschenbrenner, E.; Falk, W.; Scholmerich, J.; and Gross, V.; "Increased Interleukin 8 Expression in the Colon Mucosa of Patients With Inflammatory Bowel Disease;" *Gut*; Feb. 1996; 38 (2); 216-222; Abstract Only.

Dantzer, R.; Bluthe, R. M.; Laye, S.; Bret-Dibat, J. L.; Parnet, P.; and Kelley, K. W.; "Cytokines and Sickness Behavior;" *Ann. N. Y. Acad. Sci.*; May 1998; 840 586-590.

Darroch, C. J.; Barnes, R. M.; and Dawson, J.; "Circulating Antibodies to *Saccharomyces cerevisiae* (Bakers'/Brewers' Yeast) in Gastrointestinal Disease;" *J Clin Pathol.*; Jan. 1999; 52 (1); 47-53.

Davis, Stanley S.; Stockwell, Anita F.; Margaret J. Taylor; John G. Hardy; David R. Whalley; C.G.Wilson; Helle Bechgaard; and Finn N.Christensen; "The Effect of Density on the Gastric Emptying of Single- and Multiple-Unit Dosage Forms;" *Pharmaceutical Research*; 1986; 3 (4); 208-213.

De Campos, R. O.; Henriques, M. G.; and Calixto, J. B.; "Systemic Treatment With Mycobacterium Bovis Bacillus Calmette-Guerin (BCG) Potentiates Kinin B1 Receptor Agonist-Induced Nociception and Oedema Formation in the Formalin Test in Mice;" *Neuropeptides*; Oct. 1998; 32 (5); 393-403.

De Becker, P.; Dendale, P.; De, Meirleir K.; Campine, I.; Vandenborne, K.; and Hagers, Y.; "Autonomic Testing in Patients With Chronic Fatigue Syndrome;" *Am J Med.*; Sep. 1998; 105 (3A); 22S-26S.

De Boissieu, D.; Chaussain, M.; Badoual, J.; Raymond, J.; and Dupont, C.; "Small-Bowel Bacterial Overgrowth in Children With Chronic Diarrhea, Abdominal Pain, or Both;" *J Pediatr.*; Feb. 1996; 128 (2); 203-207.

Delin, N. A.; Axelsson, B.; Johansson, C.; and Poppen, B.; "Comparison of Gamma Camera and Withdrawal Methods for the Measurement of Gastric Emptying;" *Scand. J Gastroenterol.*; 1978; 13 (7); 867-872.

Dellert, S. F.; Nowicki, M. J.; Farrell, M. K.; Delente, J.; and Heubi, J. E.; "The 13C-Xylose Breath Test for the Diagnosis of Small Bowel Bacterial Overgrowth in Children;" *J Pediatr. Gastroenterol. Nutr.*; Aug. 1997; 25 (2); 153-158.

Demitrack, M. A.; "Neuroendocrine Aspects of Chronic Fatigue S;yndrome: a Commentary;" *Am J Med.*; Sep. 1998; 105 (3A); 11S-14S.

Dinarello, C. A.; "Role of Pro- and Anti-Inflammatory Cytokines During Inflammation: Experimental and Clinical Findings;" *J Biol. Regul. Homeost. Agents*; Jul. 1997; 11 (3); 91-103; Abstract Only.

Dobson, C. L.; Davis, S. S.; Chauhan, S.; Sparrow, R. A.; and Wilding, I. R.; "The Effect of Oleic Acid on the Human Ileal Brake and Its Implications for Small Intestinal Transit of Tablet Formulations;" *Pharm. Res.*; Jan. 1999; 16 (1); 92-96.

Dreznik, Z.; Meininger, T. A.; Barteau, J. A.; Brocksmith, D.; and Soper, N. J.; "Effect of Ileal Oleate on Interdigestive Intestinal Motility of the Dog;" *Dig. Dis. Sci.*; Jul. 1994; 39 (7); 1511-1518.

Drossman, D. A.; Patrick, D. L.; Whitehead, W. E.; Toner, B. B.; Diamant, N. E.; Hu, Y.; Jia, H.; and Bangdiwala, S. I.; "Further Validation of the IBS-QOL: a Disease-Specific Quality-of-Life Questionnaire;" *Am J Gastroenterol.*; Apr. 2000; 95 (4); 999-1007.

Eberle-Wang, K. and Simansky, K. J.; "The CCK-A Receptor Antagonist, Devazepide, Blocks the Anorectic Action of CCK but Not Peripheral Serotonin in Rats;" *Pharmacol. Biochem. Behav.*; Nov. 1992; 43 (3); 943-947; Abstract Only.

Edes, T. E.; Walk, B. E.; and Austin, J. L.; "Diarrhea in Tube-Fed Patients: Feeding Formula Not Necessarily the Cause;" *Am J Med.*; Feb. 1990; 88 (2); 91-93.

Edwards, S. and Stevens, R.; "Peripherally Administered 5-Hydroxytryptamine elicits the Full Behavioural Sequence of Satiety;" *Physiol Behav.*; Nov. 1991; 50 (5); 1075-1077.

El-Salhy, M. and Norrgard, O.; "Colonic Neuroendocrine Peptide levels in Patients With Chronic Idiopathic Slow Transit Constipation;" *Ups. J Med. Sci.*; 1998; 103 (3); 223-230; Abstract Only.

Erickson, J.C.; Hollopeter, G.; and Palmiter, R. D.; "Attenuation of the Obesity Syndrome of Ob-Ob Mice by the Loss of Neuropeptide Y;" *Science*; Dec. 1996; 274 (5293); 1704-1707.

Evans, P. R.; Bak, Y. T.; Shuter, B.; Hoschl, R.; and Kellow, J. E.; "Gastroparesis and Small Bowel Dysmotility in irritable Bowel Syndrome;" *Dig. Dis. Sci.*; Oct. 1997; 42 (10); 2087-2093; Abstract Only.

Faraone, S. V.; Biederman, J.; Weber, W.; and Russell, R. L.; "Psychiatric, Neuropsychological, and Psychosocial Features of DSM-IV Subtypes of Attention-Deficit/Hyperactivity Disorder: Results From a Clinically Referred Sample;" *J Am Acad. Child Adolesc. Psychiatry*; Feb. 1998; 37 (2); 185-193; Abstract Only.

Faris, P. L.; Kim, S. W.; Meller, W. H.; Goodale, R. L.; Oakman, S. A.; Hofbauer, R. D.; Marshall, A. M.; Daughters, R. S.; Banerjee-Stevens, D.; Eckert, E. D.; and Hartman, B. K.; "Effect of Decreasing Afferent Vagal Activity With Ondansetron on Symptoms of Bulimia Nervosa: a Randomised, Double-Blind Trial;" *Lancet*; Mar. 2000; 355 (9206); 792-797: Abstract Only.

Farthing, M. J.; "5-Hydroxytryptamine and 5-Hydroxytryptamine-3 Receptor Antagonists;" *Scand. J Gastroenterol. Suppl*; 1991; 188 92-100; Abstract Only.

Farup, P. G.; Hovedenak, N.; Wetterhus, S.; Lange, O. J.; Hovde, O.; and Trondstad, R.; "The Symptomatic Effect of Cisapride in Patients With Irritable Bowel Syndrome and Constipation;" *Scand. J Gastroenterol.*; Feb. 1998; 33 (2); 128-131.

Fausa,L.E. et al; "Crohn's Disease. Clinical Manifestations." *Scand J Gastroenterol*; Aug. 1985; 20 (6); 665-670.

Feghali, C. A. and Wright, T. M.; "Cytokines in Acute and Chronic Inflammation;" *Front Biosci.*; Jan. 1997; 2 d12-d26; Abstract Only.

Feher, E.; Kovacs, A.; Gallatz, K.; and Feher, J.; "Direct Morphological Evidence of Neuroimmunomodulation in Colonic Mucosa of Patients With Crohn's Disease;" *Neuroimmunomodulation.*; Sep. 1997; 4 (5-8); 250-257; Abstract Only.

Fellermann, K.; Ludwig, D.; Stahl, M.; Vid-Walek, T.; and Stange, E. F.; "Steroid-Unresponsive Acute Attacks of Inflammatory Bowel. Disease: Immunomodulation by Tacrolimus (FK508);" *Am J Gastroenterol.*; Oct. 1998; 93 (10); 1860-1866; Abstract Only.

Fenner, H.; "[Immunopharmacologic Profile and Therapeutic Prospects of Anti-TNF-Alpha Therapy];" *Z. Rheumatol.*; Oct. 1998; 57 (5); 294-297; Abstract Only.

Ferrara, A.; Zinner, M. J.; Hinsdale, J. G.; and Jaffe, B. M.; "Intraluminal Release of Serotonin During the Interdigestive Migrating Complex in the Canine Small Intestine;" *J Surg. Res.*; Sep. 1986; 41 (3); 308-311; Abstract Only.

Ferrara, A.; Zinner, M. J.; and Jaffe, B. M.; "Intraluminal Release of Serotonin, Substance P, and Gastrin in the Canine Small Intestine;" *Dig. Dis. Sci.*; Mar. 1987; 32 (3); 289-294; Abstract Only.

Fox-Threlkeld, J. A.; Daniel, E. E.; Christinck, F.; Woskowska, Z.; Cipris, S.; and McDonald, T. J.; "Peptide YY Stimulates Circular Muscle Contractions of the Isolated Perfused Canine Ileum by Inhibiting Nitric Oxide Release and Enhancing Acetylcholine Release;" *Peptides*; Nov. 1993; 14 (6); 1171-1178; Abstract Only.

Foxx-Orenstein, A. E.; Jin, J. G.; and Grider, J. R.; "5-HT4 Receptor Agonists and Delta-Opioid Receptor Antagonists Act Synergistically to Stimulate Colonic Propulsion;" *Am J Physiol*; Nov. 1998; 275 (5 Pt 1); G979-G983; Abstract Only.

Francis, C. Y.; Morris, J.; and Whorwell, P. J.; "The irritable Bowel Severity Scoring System: a Simple Method of Monitoring Irritable Bowel Syndrome and Its Progress;" *Aliment. Pharmacol. Ther.*; Apr. 1997; 11 (2); 395-402; Abstract Only.

Frankenfield, D. C. and Beyer, P. L.; "Soy-Polysaccharide Fiber: Effect on diarrhea in Tube-Fed, Head-Injured Patients;" *Am J Clin Nutr.*; Sep. 1989; 50 (3); 533-538; Abstract Only.

Fraser, R.; Cliff, W. J.; and Courtice, F. C.; "The Effect of Dietary Fat Load on the Size and Composition of Chylomicrons in Thoracic Duct Lymph;" *Q. J Exp. Physiol Cogn Med. Sci.*; Oct. 1968; 53 (4); 390-398.

Friedman, G.; "Diet and the Irritable Bowel Syndrome;" *Gastroenterol. Clin North Am*; Jun. 1991; 20 (2); 313-324.

Fu, L. W. and Longhurst, J. C.; "Role of 5-HT3 Receptors in Activation of Abdominal Sympathetic C Fibre Afferents During Ischaemia In Cats;" *J Physiol*; Jun. 1998; 509 (Pt 3) 729-740; Abstract Only.

Fujimiya, M.; Miyazaki, M.; Fujimura, M.; and Kimura, H.; "Effect of Carbachol on the Release of Peptide YY From Isolated Vascularly and Luminally Perfused Rat Ileum;" *Peptides*; 1995; 16 (5); 939-944; Abstract Only.

Funakoshi, K.; Sugimura, K.; Anezaki, K.; Bannai, H.; Ishizuka, K.; and Asakura, H.; "Spectrum of Cytokine Gene Expression in Intestinal Mucosal Lesions of Crohn's Disease and Ulcerative Colitis;" *Digestion*; 1998; 59 (1); 73-78; Abstract Only.

Yuji Funayama; Iwao Sasaki; Hiroo Naito; Kohei Fukushima; Tsuyoshi Masuko; Ken-Ichi Takahashi; Hitoshi Ogawa; Shun Sato; Tatsuya Ueno; Mitsunori Naguchi; Nobuo Hiwatashi; and Seiki Matsuno; "Anti-Bacterial Tretment for Postoperative Bacterial Overgrowth in Crohn's Disease;" *Minerva Gastroenterol. Dietol.*; May 1997; 112 (4 Suppl.); A1444-: Abstract Only.

Galatola, G.; Grosso, M.; Barlotta, A.; Ferraris, R.; Rovera, L.; Ariano, M.; Cottino, F.; and De La, Pierre M.; "[Diagnosis of Bacterial Contamination of the Small Intestine Using the 1 g [14C] Xylose Breath Test in Various Gastrointestinal Diseases];" *Minerva Gastroenterol. Dietol.*; Jul. 1991; 37 (3); 169-175; Abstract Only.

Galligan, J. J.; "Electrophysiological Studies of 5-Hydroxytryptamine Receptors on Enteric Neurons;" *Behav. Brain Res.*; 73 (1-2); 199-201; Abstract Only.

Gardiner, G.; Ross, R. P.; Collins, J. K.; Fitzgerald, G.; and Stanton, C.; "Development of a Probiotic Cheddar Cheese Containing Human-Derived lactobacillus Paracasei Strains;" *Appl. Environ. Microbiol.*; Jun. 1998; 64 (6); 2192-2199.

Gershon, M. D.; Wade, P. R.; Kirchgessner, A. L.; and Tamir, H.; "5-HT Receptor Subtypes Outside the Central Nervous System. Roles in the Physiology of the Gut;" *Neuropsychopharmacology*; Oct. 1990; 3 (5-6); 385-395; Abstract Only.

Gershon, M. D.; "Serotonin: Its Role and Receptors in Enteric Neurotransmission;" *Adv. Exp. Med. Biol.* 1991; 294 221-230; Abstract Only.

Gershon, M. D.; "Review Article: Roles Played by 5-Hydroxytryptamine in the Physiology of the Bowel;" *Aliment. Pharmacol. Ther.*; May 1999; 13 Suppl 2 15-30; Abstract Only.

Gielkens, H. A.; Nieuwenhuizen, A.; Biemond, I.; Lamers, C. B.; and Masclee, A. A.; "Interdigestive Antroduodenal Motility and Gastric Acid Secretion;" *Aliment. Pharmacol. Ther.*; Jan. 1998; 12 (1): 27-33; Abstract Only.

Giralt, M. and Vergara, P.; "Both Afferent and Efferent Nerves Are Implicated in Cholecytokinin Motor Actions in the Small Intestine of the Rat;" *Regul. Pept.*; May 1999; 81 (1-3); 73-80; Abstract Only.

Girardet, R. E. and Benninghoff, D. L.; "Surgical Techniques for Long-Term Study of Thoracic Duct Lymph Circulation in Dogs;" *J Surg. Res.*; Sep. 1973; 15 (3); 168-175.

Glaser, R. and Kiecolt-Glaser, J. K.; "Stress-Associated Immune Modulation: Relevance to Viral Infections and Chronic Fatigue Syndrome;" *Am J Med.*; Sep. 1998; 105 (3A); 35S-42S.

Gorard, D. A. and Farthing, M. J.; "Intestinal Motor Function in Irritable Bowel Syndrome;" *Dig. Dis.*; Mar. 1994; 12 (2); 72-84; Abstract Only.

Gorard, D. A.; Libby, G. W.; and Farthing, M. J.; "Ambulatory Small Intestinal Motility in 'Diarrhea' Predominant Irritable Bowel Syndrome;" *Gut*; Feb. 1994; 35 (2); 203-210.

Gotz, V. P. and Rand, K. H.; "Medical Management of Antimicrobial-Associated Diarrhea and Colitis;" *Pharmacotherapy*; Mar. 1982; 2 (2); 100-109.

Grider, J. R.; Foxx-Orsenstein, A. E.; and Jin, J. G.; "5-Hydroxytryptamine4 Receptor Agonists Initiate the Peristaltic Reflex in Human, Rat, and Guinea Pig Intestine;" *Gastroenterology*; Aug. 1998; 115 (2); 370-380; Abstract Only.

Groll, D.; Vanner, S. J.; Depew, W. T.; Dacosta, L. R.; Simon, J. B.; Groll, A.; Roblin, N.; and Paterson, W. G.; "The IBS-36: a New Quality of Life Measure for Irritable Bowel Syndrome;" *Am J Gastroenterol.*; Apr. 2002; 97 (4); 962-971.

Gruy-Kapral, C.; Little, K. H.; Fordtran, J. S.; Meziere, T. L.; Hagey, L. R.; and Hofmann, A. F.; "Conjugated Bile Acid Replacement Therapy for Short-Bowel Syndrome;" *Gastroenterology*; Jan. 1999; 116 (1); 15-21.

Gue, M.; Junien, J. L.; Reeve, J. R., Jr.; Rivier, J.; Grandt, D.; and Tache, Y.; "Reversal by NPY, PYY and 3-36 Molecular Forms of NPY and PYY of Intracisternal CRF-Induced Inhibition of Gastric Acid Secretion in Rats 1;" *Br. J. Pharmacol.*; May 1996; 118 (2); 237-242.

Guimbaud, R.; Bertrand, V.; Chauvelot-Moachon, L.; Quartier, G.; Vidon, N.; Giroud, J. P.; Couturier, D.; and Chaussade, S.; "Network of Inflammatory Cytokines and Correlation With Disease Activity in Ulcerative Colitis;" *Am J Gastroenterol.*; Dec. 1998; 93 (12); 2397-2404; Abstract Only.

Gunn, M. C.; Cavin, A. A.; and Mansfield, J. C.; "Management of Irritable Bowel Syndrome;" *Postgrad. Med. J*; Mar. 2003; 79 (929); 154-158.

Gwinup, G.; Byron, R. C.; Roush, W. H. Kruger, F. A.; and Hamwi, G. J.; "Effect of Nibbling Versus Gorging on Serum Lipids in Man;" *Am J Clin Nutr.*; Oct. 1963; 13 209-213.

Hang, L.; Wullt, B.; Shen, Z.; Karpman, D.; and Svanborg, C.; "Cytokine Repertoire of Epithelial Cells Lining the Human Urinary Tract;" *J Urol.*; Jun. 1998; 159 (6); 2185-2192; Abstract Only.

Harlow, B. L.; Signorello, L. B.; Hall, J. E.; Dailey, C.; and Komaroff, A. L.; "Reproductive Correlates of Chronic Fatigue Syndrome;" *Am J Med.*; Sep. 1998; 105 (3A); 94S-99S.

Hayashi, Hiroshoi et al; "Fat Feeding Increases Size, but Not Number, of Chylomicrons produced by small intestine;" *The American Physiological Society*; Chapter 22, G709-G719; 1990.

Hellstrom, P. M.; Nilsson, I.; and Svenberg, T.; "Role of Bile in Regulation of Gut Motility;" *J Intern. Med.*; Apr. 1995; 237 (4); 395-402; Abstract Only.

Hollopeter, G.; Erickson, J. C.; Seeley, R. J.; Marsh, D. J.; Palmiter, R. D.; "Response of. Neuropeptide Y-Deficient Mice to Feeding Effectors;" *Regul. Pept.*; Sep. 1998; 75-76 383-389; Abstract Only.

Hori, T.; Oka, T.; Hosoi, M.; and Aou, S.; "Pain Modulatory Actions of Cytokines and Prostaglandin E2 in the Brain;" *Ann. N. Y. Acad. Sci.*; May 1998; 840 269-281; Abstract Only.

Hudziak, J. J.; Heath, A. C.; Madden, P. F.; Reich, W.; Bucholz, K. K.; Slutske, W.; Bierut, L. J.; Neuman, R. J.; and Todd, R. D.; "Latent Class and Factor Analysis of DSM-IV ADHD: a Twin Study of Female Adolescents;" *J Am Acad. Child Adolesc. Psychiatry*; Aug. 1998; 37 (8); 848-857; Abstract Only.

Huge, A.; Weber, E.; and Ehrlein, H. J.; "Effects of Enteral Feedback Inhibition on Motility, Luminal Flow, and Absorption of Nutrients in Proximal Gut of Minipigs;" *Dig. Dis. Sci.*; May 1995; 40 (5); 1024-1034.

Hughes, J. J.; Levine, A. S.; Morley, J. E.; Gosnell, B. A.; and Silvis, S. E.; "Intraventricular Calcitonin Gene-Related Peptide Inhibits Gastric Acid Secretion;" *Peptides*;Jul. 1984; 5 (4); 665-667.

Hyams, J. S.; Fitzgerald, J. E.; Wyzga, N.; Muller, R.; Treem, W. R.; Justinich, C. J.; and Kreutzer, D. L.; "Relationship of Interleukin-1 Receptor Antagonist to Mucosal Inflammation in Inflammatory Bowel Disease;" *J Pediatr. Gastroenterol. Nutr.*; Nov. 1995; 21 (4); 419-425; Abstract Only.

Inui, A.; "Feeding and Body-Weight Regulation by Hypothalamic Neuropeptides—Mediation of the Actions of Leptin;" *Trends Neurosci.*; Feb. 1999; 22 (2); 62-67; Abstract Only.

Irwin, M. I. and Feeley, R. M.; "Frequency and Size of Meals and Serum Lipids, Nitrogen and Mineral Retention, Fat Digestibility, and Urinary Thiamine and Riboflavin in Young Women;" *Am J Clin Nutr.*; Aug. 1967; 20 (8); 816-824.

Jackerott, M. and Larsson, L. I.; "Immunocytochemical Localization of the NPY/PYY Y1 Receptor in Enteric Neurons, Endothelial Cells, and Endocrine-Like Cells of the Rat Intestinal Tract;" *J Histochem. Cytochem.*; Dec. 1997; 45 (12); 1643-1650; Abstract Only.

Jagannathan, S. N.; Connell, W. F.; and Beveridge, J. M.; "Effects of Gormandizing and Semicontinuous Eating of Equicaloric Amounts of Formula-Type High Fat Diets on Plasma Cholesterol and Triglyceride Levels in Human Volunteer Subjects;" *Am J Clin Nutr.*; Aug. 1964; 15 90-93.

Jason, L. A.; Wagner, L.; Rosenthal, S.; Goodlatte, J.; Lipkin, D.: Papernik, M.; Plioplys, S.; and Plioplys, A. V.; "Estimating the Prevalence of Chronic Fatigue Syndrome Among Nurses;" *Am J Med.*; Sep. 1998; 105 (3A); 91S-93S.

Jenkins, D. J.; Wolever, T. M.; Vuksan, V.; Brighenti, F.; Cunnane, S. C.; Rao, A. V.; Jenkins, A. L.; Buckley, G.; Patten, R.; Singer, W.; and .; "Nibbling Versus Gorging: Metabolic Advantages of Increased Meal Frequency;" *N. Engl. J Med.*; Oct. 1989; 321 (14); 929-934.

Jenkins, P. J.; Harper, R. W.; and Nestel, P. J.; "Severity of Coronary Atherosclerosis Related to Lipoprotein Concentration;" *Br. Med. J*; Aug. 1978; 2 (6134); 388-391.

Jin, J. G.; Foxx-Orenstein, A. E.; and Grider, J. R.; "Propulsion in Guinea Pig Colon Induced by 5-Hydroxytryptamine (HT) Via 5-HT4 and 5-HT3 Receptors;" *J Pharmacol. Exp. Ther.*; Jan. 1999; 288 (1); 93-97; Abstract Only.

Kanik, K. S.; Hagiwara, E.; Yarboro, C. H.; Schumacher, H. R.; Wilder, R. L.; and Klinman, D. M.; "Distinct Patterns of Cytokine Secretion Characterize New Onset Synovitis Versus Chronic Rheumatoid Arthritis;" *J Rheumatol.*; Jan. 1998; 25 (1); 16-22; Abstract Only.

Karcher, R. E.; Truding, R. M.; and Stawick, L. E.; "Using a Cutoff of <10 Ppm for Breath Hydrogen Testing: a Review of Five Years' Experience;" *Ann. Clin Lab Sci.*; Jan. 1999; 29 (1); 1-8.

Keinke, O. and Ehrlein, H. J.; "Effect of Oleic Acid on Canine Gastroduodenal Motility, Pyloric Diameter and Gastric Emptying;" *Q. J Exp. Physiol*; Oct. 1983; 68 (4); 675-686.

Keinke, O.; Schemann, M.; and Ehrlein, H. J.; "Mechanical Factors Regulating Gastric Emptying of Viscous Nutrient Meals in Dogs;" *Q. J Exp. Physiol*; Oct. 1984; 69 (4); 781-795.

Kellow, J. E.; Eckersley, C. M.; and Jones, M. P.; "Enhanced Perception of Physiological Intestinal Motility in the irritable Bowel Syndrome;" *Gastroenterology*; Dec. 1991; 101 (6); 1621-1627; Abstract Only.

Kellum, J. M.; Albuquerque, F. C.; Stoner, M. C.; and Harris, R. P.; "Stroking Human Jejunal Mucosa Induces 5-HT Release and Cl- Secretion Via Afferent Neurons and 5-HT4 Receptors;" *Am J Physiol*; Sep. 1999; 277 (3 Pt 1): G515-G520; Abstract Only.

Kerlin, P. and Wong, L.; "Breath Hydrogen Testing in Bacterial Overgrowth of the Small Intestine;" *Gastroenterology*; Oct. 1988; 95 (4); 982-988; Abstract Only.

Khosla, R. and Davis, S. S.; "The Effect of Polycarbophil on the Gastric Emptying of Pellets;" *J Pharm. Pharmacol.*; Jan. 1987; 39 (1); 47-49.

King, C. E. and Toskes, P. P.; "Breath Tests in the Diagnosis of Small Intestine Bacterial Overgrowth;" *Crit Rev. Clin Lab Sci.*; 1984: 21 (3); 269-281.

King, C. E. and Toskes, P. P.; "Comparison of the 1-Gram [14C]Xylose, 10-Gram Lactulose-H2, and 80-Gram Glucose-H2 Breath Tests in Patients With Small Intestine Bacterial Overgrowth;" *Gastroenterology*; Dec. 1986; 91 (6); 1447-1451; Abstract Only.

King, P. J.; Widdowson, P. S.; Doods, H. N.; and Williams, G.; "Regulation of Neuropeptide Y Release by Neuropeptide Y Receptor Ligands and Calcium Channel Antagonists in Hypothalamic Slices;" *J Neurochem.*, Aug. 1999; 73 (2); 641-646; Abstract Only.

King, P. J.; Widdowson, P. S.; Doods, H.; and Williams, G.; "Effects of Cytokines on Hypothalamic Neuropeptide Y Release in Vitro;" *Peptides*; Jan. 2000; 21 (1); 143-146; Abstract Only.

King, P. J.; Widdowson, P. S.; Doods, H.; and Williams, G.; "Regulation of Neuropeptide Y Release From Hypothalamic Slices by Melanocortin-4 Agonists and Leptin;" *Peptides*; Jan. 2000; 21 (1); 45-48; Abstract Only.

King, T. S.; Elia, M.; and Hunter, J. O.; "Abnormal Colonic Fermentation in Irritable Bowel Syndrome;" *Lancet*; Oct. 1998; 352 (9135); 1187-1189.

Kirchgessner, A. L.; Liu, M. T.; Raymond, J. R.; and Gershon, M. D.; "identification of Cells That Express 5-Hydroxytryptamine1A Receptors in the Nervous Systems of the Bowel and Pacreas;" *J Comp Neurol.*; Jan. 1996; 364 (3); 439-455: Abstract Only.

Kitchener, S. J. and Dourish, C. T.; "An Examination of the Behavioural Specificity of Hypophagia Induced by 5-HT1B, 5-HT1C and 5-HT2 Receptor Agonists Using the Post-Prandial Satiety Sequence in Rats;" *Psychopharmacology (Berl)*; Jan. 1994; 113 (3-4); 369-377; Abstract Only.

Knutson, D.; Greenberg, G.; and Cronau, H.; "Management of Crohn's Disease—a Practical Approach;" *Am Fam. Physician*; Aug. 2003; 68 (4); 707-714.

Kokot, F. and Ficek, R.; "Effects of Neuropeptide Y on Appetite;" *Miner. Electrolyte Metab*; Jul. 1999; 25 (4-6): 303-305; Abstract Only.

Kontula, P.; Suihko, M. L.; Von, Wright A.; and Mattila-Sandholm, T.; "The Effect of Lactose Derivatives on Intestinal Lactic Acid Bacteria;" *J Dairy Sci.*; Feb. 1999; 82 (2); 249-256; Abstract Only.

Kuboyama, S.; "Increased Circulating Levels of Interleukin-1 Receptor Antagonist in Patients With Inflammatory Bowel Disease;" *Kurume Med. J*; 1998; 45 (1); 33-37; Abstract Only.

Kucharzik, T.; Stoll, R.; Lugering, N.; and domschke, W.; "Circulating Antiinflammatory Cytokine IL-10 in Patients With Inflammatory Bowel Disease (IBD);" *Clin Exp. Immunol.*; Jun. 1995; 100 (3); 452-456; Abstract Only.

Kucharzik, T.; Lugering, N.; Weigelt, H.; Adolf, M.; Domschke, W.; and Stoll, R.; "Immunoregulatory Properties of IL-13 in Patients With Inflammatory Bowel Disease; Comparison With IL-4 and IL-10;" *Clin Exp. Immunol.*; Jun. 1996; 104 (3); 483-490; Abstract Only.

Kucharzik, T.; Lugering, N.; Adolf, M.; Domschke, W.; and Stoll, R.; "Synergistic Effect of Immunoregulatory Cytokines on Peripheral Blood Monocytes From Patients With Inflammatory Bowel Disease;" *Dig. Dis. Sci.*; Apr. 1997; 42 (4); 805-812; Abstract Only.

Kuemmerle, J. F. and Kellum, J. M.; "Serotonin Neural Receptors Mediate Motilin-Induced Motility in Isolated, Vascularly Perfused Canine Jejunum;" *J Surg. Res.*; Oct. 1988; 45 (4); 357-362; Abstract Only.

Lai, K. K.; Melvin, Z. S.; Menard, M. J.; Kotilainen, H. R.; and Baker, S.; "Clostridium Difficile-Associated Diarrhea: Epidemiology, Risk Factors, and Infection Control;" *Infect. Control Hosp. Epidemiol.*; Sep. 1997; 18 (9); 628-632.

Lamanca, J. J.; Sisto, S. A.; Deluca, J.; Johnson, S. K.; Lange, G.; Pareja, J.; Cook, S.; and Netelson, B. H.; "Influence of Exhaustive Treadmill Exercise on Cognitive Functioning in Chronic Fatigue Syndrome;" *Am J Med.*; Sep. 1998; 105 (3A); 59S-65S.

Lange, G.; Wang, S.; Deluca, J.; and Natelson, B. H.; "Neuroimaging in Chronic Fatigue Syndrome;" *Am J Med.*; Sep. 1998; 105 (3A); 50S-53S.

Laviano, A.; Cangiano, C.; Fava, A.; Muscaritoli, M.; Mulieri, G.; and Rossi, Fanelli F.; "Peripherally Injected IL-1 Induces Anorexia and Increases Brain Tryptophan Concentrations;" *Adv. Exp. Med. Biol.*1999; 467 105-108; Abstract Only.

Lederman, E.; Neut, C.; Desreumaux, P.; Klein, O.; Gambiez, L.; Cortot, A.; and Quandalle, P.; "Bacterial Overgrowth in the Neoterminal Ileum After Illeocolonic Resection for Crohn's Disease;" *Gastroenterology*; 1997; 112 (4 Suppl.); A1023-.

Leiper, K.; London, I.; and Rhodes, J. M.; "Adjuvant Post-Operative Therapy;" *Baillieres Clin Gastroenterol.*; Mar. 1998; 12 (1); 179-199; Abstract Only.

Lembcke, B.; "[Breath Tests in Intestinal Diseases and Functional Gastrointestinal Diagnosis];" *Schweiz. Rundsch. Med. Prax.*; Jun. 1997; 86 (25-26); 1060-1067; Abstract Only.

Lepionka, L.; Malbert, C. H.; and Laplace, J. P.; "Proximal Gastric Distension Modifies Ingestion Rate in Pigs;" *Reprod. Nutr.Dev.*; Jul. 1997; 37 (4); 449-457; Abstract Only.

Levine, P. H.; "What We Know About Chronic Fatigue Syndrome and Its Relevance to the Practicing Physician;" *Am J Med.*; Sep. 1998; 105 (3A); 100S-103S.

Lewindon, P. J.; Robb, T. A.; Moore, D. J.; Davidson, G. P.; and Martin, A. J.; "Bowel Dysfunction in Cystic Fibrosis; Importance of Breath Testing;" *J Paediatr. Child Health*; Feb. 1998; 34 (1); 79-82; Abstract Only.

Lin, H. C.; Doty, J. E.; Reedy, T. J.; and Meyer, J. H.; "Inhibition of Gastric Emptying by Glucose Depends on Length of Intestine Exposed to Nutrient;" *Am J Physiol*; Feb. 1989; 256 (2 Pt 1); G404-G411.

Lin, H. C.; Doty, J. E.; Reedy, T. J.; and Meyer, J. H.; "Inhibition of Gastric Emptying by Sodium Oleate Depends on Length of Intestine Exposed to Nutrient;" *Am J Physiol*; Dec. 1990; 259 (6 Pt 1); G1031-G1036; Abstract Only.

Lin, H. C.; Zhao, X. T.; Reddy , S. N.; Wang, L. J.; and Y.-G.Gu; "Inhibition of Intestinal Transit by Fat Depends on Length of Exposure to Nutrient;" *Gastroenterology*; 1994; 106 A531; Abstract Only.

Lin, H. C.; Y.-G.Gu; and J.H.Meyer; "Acute Desensitization of Intestinal Motility Response;" *Gastroenterology*; 1995; 103 1392-; Abstract Only.

Lin, H. C.; G.Bonorris; and J.W.Marks; "Oleate Slows Upper Gut Transit and Reduces Diarrhea in Patients With Rapid Upper Gut Transit and Diarrhea;" *Gastroenterology*; 1995; 108 (4); A638-.

Lin, H. C.; Zhao, X. T.; Wang, L.; and Wong, H.; "Fat-Induced Ileal Brake in the Dog Depends on Peptide YY;" *Gastroenterology*; May 1996; 110 (5); 1491-1495; Abstract Only.

Lin, H. C.; Zhao, X. T.; Chung, B.; Gu, Y. G.; and Elashoff, J. D.; "Frequency of Gastric Pacesetter Potential Depends on Volume and Site of Distension;" *Am J Physiol*; Mar. 1996; 270 (3 Pt 1); G470-G475.

Lin, H. C.; Zhao, X. T.; and Wang, L. J.; "Intestinal Transit of Fat in Proximal Gut Depends on Accelerating Effect of CCK and Slowing Effect of Opioid Pathway;" *Digestive diseases and Sciences*; Sep. 1996; 41 (9) ; Abstract Only.

Lin, H. C.; Zhao, X. T.; and Wang, L.; "Jejunal Brake: Inhibition of Intestinal Transit by Fat in the Proximal Small Intestine;" *Dig. Dis. Sci.*; Feb. 1996; 41 (2); 326-329.

Lin, H. C.; Zhao, X. T.; and Wang, L.; "Intestinal Transit Is More Potently Inhibited by Fat in the Distal (Ileal Brake) Than in the Proximal (Jejunal Brake) Gut;" *Dig. Dis. Sci.*; Jan. 1997; 42 (1); 19-25; Abstract Only.

Lin, H. C.; Walsh, J. H.; Zhao, X. T.; Wang, L. J.; and Wong, H.; "Immunoneutralization of Calcitonin Gene-Related Peptide (CGRP) During Inhibition of Intestinal Transit by Fat;" *Gastorentology*; 1998; 114 (4); A790-; Abstract Only.

Lin, H. C.; Chey, W. Y.; Tso, P.; and Zhao, X. T.; "Release of Cholecystokinin by Proximal Gut Fat Independent of Chylomichron Transport;" *Gastroenterology*; 1998; 114 (4); A1159-: Abstract Only.

Lin, H. C.; Wang, L. J.; and Zhao, X. T.; "Slowing of Intestinal Transit by Fat in Proximal Gut Depends on Peptide YY;" *Neurogastroenterology and Motility*; 1998; 82-: Abstract Only.

Lin, H. C.; Taylor, I. L.; Wang, L. J.; and Zhao, X. T.; "PYY Release by Fat in the Proximal But Not Distal of Gut Depends on Atropine-Blockable Cholinergie Pathway;" *Gastroenterology*; 1998; 114 (4); A1149-; Abstract Only.

Lin, H. C.; "Intestinal Transit Response to Fat in the Proximal Gut Depends on 5-Hydroxytryptamine;" *Gastroenterology*; 1998; 114 (4); A790-; Abstract Only.

Lin, H. C.; Zhao, X. T.; and Wang, L. J.; "Fat-Induced Ileal Brake Depends on Cholecstokinin;" *Gastroenterology*; 1998; 114 (4); A790-; Abstract Only.

Litvak, D. A.; Iseki, H.; Evers, B. M.; Greeley, G. H., Jr.; Hellmich, M. R.; Iwase, K.; Balasubramaniam, A.; and Townsend, C. M., Jr.; "Characterization of Two Novel Proabsorptive Peptide YY Analogs, BIM-43073D and BIM-43004C;" *Dig. Dis. Sci.*; Mar. 1999; 44 (3); 643-648; Abstract Only.

Liu, C. D.; Aloia, T.; Adrian, T. E.; Newton, T. R.; Bilchik, A. J.; Zinner, M. J.; Ashley, S. W.; and McFadden, D. W.; "Peptide YY; a Potential Proabsorptive Hormone for the Treatment of Malabsorptive Disorders;" *Am Surg.*; Mar. 1996; 62 (3); 232-236; Abstract Only.

Liu, C. D.; Newton, T. R.; Zinner, M. J.; Ashley, S. W.; and McFadden, D. W.; "Intraluminal Peptide YY Induces Colonic Absorption in Vivo;" *Dis. Colon Rectum*; Apr. 1997; 40 (4); 478-482; Abstract Only.

Liu, M.; Shen, L.; and Tso, P.; "The Role of Enterostatin and Apolipoprotein AIV on the Control of Food Intake;" *Neuropeptides*; Oct. 1999; 33 (5); 425-433; Abstract Only.

Lugering, N.; Kucharzik, T.; Stoll, R.; and Domschke, W.; "Current Concept of the Role of Monocytes/Macrophages in Inflammatory Bowel Disease-Balance of Proinflammatory and Immunosuppressive Mediators;" *Ital. J Gastroenterol. Hepatol.*; Jun. 1998; 30 (3); 338-344; Abstract Only.

Luiking, Y. C.; Van Der Reijden, A. C.; Van Berge Henegouwen, G. P.; and Akkermans, L. M.; "Migrating Motor Complex Cycle Duration is Determined by Gastric or Duodenal Origin of Phase III;" *Am J Physiol*; Dec. 1998; 275 (6 Pt 1); G1246-G1251; Abstract Only.

MacDermott, R. P.; "Alterations of the Mucosal Immune System in Inflammatory Bowel Disease;" *J Gastroenterol.*; Dec. 1996; 31 (6); 907-916.

MacIntosh, C. G.; Andrews, J. M.; Jones, K. L.; Wishart, J. M.; Morris, H. A.; Jansen, J. B.; Morley, J. E.; Horowitz, M.; and Chapman, I. M.; "Effects of Age on Concentrations of Plasma Cholecystokinin, Glucagon-Like Peptide 1, and Peptide YY and Their Relation to Appetite and Pyloric Motility;" *Am J Clin Nutr.*; May 1999; 69 (5); 999-1006; Abstract Only.

Mack, D. R.; Dhawan, A.; Kaufman, S. S.; Langnas, A. N.; and Seemayer, T. A.; "Small Bowel Bacterial Overgrowth As a Cause of Chronic Diarrhea After Liver Transplantation in Children;" *Liver Transpl. Surg.*; Mar. 1998; 4 (2); 166-169; Abstract Only.

Maida, V. and Howlett, G. J.; "Effects of Cigarette Smoking and Dietary Lipids on Rat Lipoprotein Metabolism;" *Atherosclerosis*; Jan. 1990; 80 (3); 209-216.

Maini, R. N.; "A Perspective on Anti-Cytokine and Anti-T Cell-Directed Therapies in rheumatoid Arthritis;" *Clin. Exp. Rheumatol.*; Sep. 1995; 13 Suppl 12 S35-S40; Abstract Only.

Mannon, P. J.; Kanungo, A.; Mannon, R. B.; and Ludwig, K. A.; "Peptide YY/Neuropeptide Y Y1 Receptor Expression in the Epithelium and Mucosal Nerves of the Human Colon;" *Regul. Pept.*; Aug. 1999; 83 (1); 11-19; Abstract Only.

Marlin, R. G.; Anchel, H.; Gibson, J. C.; Goldberg, W. M.; and Swinton, M.; "An Evaluation of Multidisciplinary Intervention for Chronic Fatigue Syndrome With Long-Term Follow-Up, and a Comparison With Untreated Controls;" *Am J Med.*; Sep. 1998; 105 (3A); 110S-114S.

Mastropaolo, G. and Rees, W. D.; "Evaluation of the Hydrogen Breath Test in Man: Definition and Elimination of the Early Hydrogen Peak;" *Gut*; Jun. 1987; 28 (6); 721-725; Abstract Only.

Matsukawa, A.; Yoshimura, T.; Miyamoto, K.; Ohkawara, S.; and Yoshinaga, M.; "Analysis of the Inflammatory Cytokine Network Among TNF Alpha, IL-1 Receptor Antagonist, and IL-8 in LPS-Induced Rabbit Arthritis;" *Lab Invest*; May 1997; 76 (5); 629-638; Abstract Only.

Matsukawa, A. and Yoshinaga, M.; "Sequential Generation of Cytokines During the Initiative Phase of Inflammation, With Reference to Neutrophils;" *Inflamm. Res.*; Oct. 1998; 47 Suppl 3 S137-S144; Abstract Only.

Mawe, G. M.; Branchek, T. A.; and Gershon, M. D.; "Peripheral Neural Serotonin Receptors: indentification and Characterization With Specific Antagonists and Agonists;" *Proc. Natl. Acad. Sci. U. S. A*; Dec. 1986; 83 (24); 9799-9803; Abstract Only.

McColl, K. E.; Murray, L. S.; Gillen, D.; Walker, A.; Wirz, A.; Fletcher, J.; Mowat, C.; Henry, E.; Kelman, A.; and Dickson, A.; "Randomised Trial of Endoscopy With Testing for Helicobacter Pylori Compared With Non-Invasive H Pylori Testing Alone in the Management of Dyspepsia;" *BMJ*; Apr. 2002; 324 (7344); 999-1002.

McGill, H. C., Jr.; "Potential mechanisms for the Augmentation of Atherosclerosis and Atherosclerotic Disease by Cigarette Smoking;" *Prev. Med.*; May 1979; 8 (3); 390-403.

McHugh, P. R. and Moran, T. H.; "The Stomach, Cholecystokinin, and Satiety;" *Fed. Proc.*; Apr. 1986; 45 (5); 1384-1390; Abstract Only.

McKeown, L. A.; "Breath Test Helps Sniff Out Irritable Bowel Syndrome: Majority of Sufferers May Have Treatable Bacterial Infections;" *WebMD Medical News*; Dec. 2000.

McVay, L. D.; Li, B.; Biancaniello, R.; Creighton, M. A.; Bachwich, D.; Lichtenstein, G.; Rombeau, J. L.; and Carding, S. R.; "Changes in Human Mucosal Gamma Delta T Cell Repertoire and Function Associated With the Disease Process in Inflammatory Bowel Disease;" *Mol. Med.*; Mar. 1997; 3 (3); 183-203; Abstract Only.

Meissner, W.; Schmidt, U.; Hartmann, M.; Kath, R.; and Reinhart, K.; "Oral Naloxone Reverses Opioid-Associated Constipation;" *Pain*; Jan. 2000; 84 (1); 105-109; Abstract Only.

Mishkin, D. and Mishkin, S.; "Re: Pimentel Et Al.—Eradication of Small Intestinal Bacterial Overgrowth Reduces Symptoms of irritable Bowel Syndrome;" *Am J Gastroenterol.*; Aug. 2001; 96 (B); 2505-2506.

Mjos, O. D.; Faergeman, O.; Hamilton, R. L.; and Havel, R. J.; "Characterization of Remnants Produced During the Metabolism of Triglyceride-Rich Lipoproteins of Blood Plasma and Intestinal Lymph in the Rat;" *J Clin Invest*; Sep. 1975; 56 (3); 603-615.

Moran, T. H. and McHugh, P. R.; "cholecystokinin Suppresses Food Intake by Inhibiting Gastric Emptying;" *Am J Physiol*; May 1982; 242 (5); R491-R497.

Morisse, J.P.; "Effect of a Fructo-Oglio-Saccharides Compound in Rabbits Experimentally Infected with *E. coli;*" *Journal of Applied Rabbit Research*; 1995; 15, 1137-1143.

Muller, S.; Lory, J.; Corazza, N.; Griffiths, G. M.; Z'Graggen, K.; Mazzucchelli, L.; Kappeler, A.; and Mueller, C.; "Activated CD4+ and CD8+ Cytotoxic Cells Are Present in Increased Numbers in the Intestinal Mucosa From Patients With Active Inflammatory Bowel Disease;" *Am J Pathol.*; Jan. 1998; 152 (1); 261-268; Abstract Only.

Muranishi, S.; Tokunaga, Y.; Taniguchi, K.; and Sezaki, H.; "Potential Absorption of Heparin From the Small Intestine and the Large Intestine in the Presence of Monoolein Mixed Micelles;" *Chem. Pharm. Bull. (Tokyo)*; May 1977; 25 (5); 1159-1161.

Murata, Y.; Ishiguro, Y.; Itoh, J.; Munakata, A.; and Yoshida, Y.; "The Role of Proinflammatory and Immunoregulatory Cytokines in the Pathogenesis of Ulcerative Colitis;" *J Gastroenterol.*; Nov. 1995; 30 Suppl 8 56-60; Abstract Only.

Murphy, B. V.; Ion, F.; and Winstanley, J. R.; "Intestinal Pseudo-Obstruction Associated With Oral Morphine;" *Eur J Anaesthesiol*; May 1998; 15 (3); 370-371; Abstract Only.

Murphy, K.; "Adults With Attention Deficit Hyperactivity Disorder: Assessment and Treatment Considerations;" *Semin. Speech Lang*; Aug. 1996; 17 (3); 245-253; Abstract Only.

Naidu, A. S.; Bidlack, W. R.; and Clemens, R. A.; "Probiotic Specta of Lactic Acid Bacteria (LAB);" *Crit Rev. Food Sci. Nutr.*; Jan. 1999; 39 (1); 13-126; Abstract Only.

Nassif, A.; Longo, W. E.; Mazuski, J. E.; Vernava, A. M.; and Kaminski, D. L.; "Role of Cytokines and Platelet-Activating Factor in Inflammatory Bowel Disease. Implications for Therapy;" *Dis. Colon Rectum*; Feb. 1996; 39 (2); 39 (2); 217-223; Abstract Only.

Natelson, B. H.; Lamanca, J. J.; Denny, T. N.; Vladutiu, A.; Oleske, J.; Hill, N.; Bergen, M. T.; Korn, L.; and Hay, J.; "Immunologic Parameters in Chronic Fatigue Syndrome, Major Depression, and Multiple Sclerosis;" *Am J Med.*; Sep. 1998; 105 (3A); 43S-49S.

Naveilhan, P.; Hassani, H.; Canals, J. M.; Ekstrand, A. J.; Larefalk, A.; Chhajlani, V.; Arenas, E.; Gedda, K.; Svensson, L.; Thoren, P.; and Ernfors, P.; "Normal Feeding Behavior, Body Weight and Leptin Response Require the Neuropeptide Y Y2 Receptor 1;" *Nat. Med.* ; Oct. 1999; 5 (10); 1188-1193; Abstract Only.

Nielsen, O. H.; Rudiger, N.; Gaustadnes, M.; and Horn, T.; "Intestinal Interleukin-8 Concentration and Gene Expression in Inflammatory Bowel Disease;" *Scand. J Gastroenterol.*; Oct. 1997; 32 (10); 1028-1034; Abstract Only.

Niessner, M. and Volk, B. A.; "Altered Th1/Th2 Cytokine Profiles in the Intestinal Mucosa of Patients With Inflammatory Bowel Disease As Assessed by Quantitative Reversed Transcribed Polymerase Chain Reaction (RT-PCR);" *Clin Exp. Immunol.*; Sep. 1995; 101 (3); 428-435; Abstract Only.

Nieuwenhuijs, V. B.; Luiking, Y. C.; Verheem, A.; Vanberge-Henegouwen, G. P.; Gooszen, H. G.; and Akkermans, L. M.; "Disrupted Bile Flow Affects Interdigestive Small Bowel Motility in Rats;" *Surgery*; Sep. 1997; 122 (3); 600-608; Abstract Only.

Nieuwenhuijs, V. B.; Verheem, A.; Van Duijvenbode-Beumer, H.; Visser, M. R.; Verhoef, J.; Gooszen, H. G.; and Akkermans, L. M.; "The Role of Interdigestive Small Bowel Motility in the Regulation of Gut Microflora, Bacterial Overgrowth, and Bacterial Translocation in Rats;" *Ann. Surg.*; Aug. 1998; 228 (2); 188-193; Abstract Only.

Nieuwenhuijs, V. B.; Van Duijvenbode-Beumer, H.; Verheem, A.; Visser, M. R.; Verhoef, J.; Gooszen, H. G.; and Akkermans, L. M.; "The Effects of ABT-229 and Octreotide on Interdigestive Small Bowel Motility, Bacterial Overgrowth and Bacterial Translocation in Rats;" *Eur. J Clin Invest*; Jan. 1999; 29 (1); 33-40; Abstract Only.

Noor, N.; Small, P. K.; Loudon, M. A.; Hau, C.; and Campbell, F. C.; "Effects of Cisapride on Symptoms and Postcibal Small-Bowel Motor Function in Patients With Irritable Bowel Syndrome;" *Scand. J Gastroenterol.*; Jun. 1998; 33 (6); 605-611.

O'Brien, J. D.; Thompson, D. G.; McIntyre, A.; Burnham, W. R.; and Walker, E.; "Effect of Codeine and Loperamide on Upper Intestinal Transit and Absorption in Normal Subjects and Patients With Postvagotomy Diarrhoea;" *Gut*; Mar. 1988; 29 (3); 312-318.

Ohtani, N.; Sasaki, I.; Naito, H.; Tsuchiya, T.; Takahashi, M.; Shibata, C.; and Matsuno, S.; "Mediators For Ileal Brake Differ Between the Stomach and Small Intestine in Conscious Dogs;" *Gastroenterology*; 1995; 108 (4 Supp.) Abst. 660.

Ormsbee, H. S., III and Fondacaro, J. D.; "Action of Serotonin on the Gastrointestinal Tract;" *Proc. Soc. Exp. Biol. Med.*; Mar. 1985; 178 (3); 333-338; Abstract Only.

Panja, A.; Goldberg, S.; Eckmann, L.; Krishen, P.; and Mayer, L.; "The Regulation and Functional Consequence of Proinflammatory Cytokine Binding on Human Intestinal Epithelial Cells;" *J Immunol.*; Oct. 1998; 161 (7); 3675-3684.

Pappas, T. N.; Melendez, R. L.; and Debas, H. T.; "Gastric Distension Is a Physiologic Satiety Signal in the Dog;" *Dig. Dis. Sci.*; Oct. 1989; 34 (10); 1489-1493; Abstract Only.

Parkes, M.; Satsangi, J.; and Jewell, D.; "Contribution of the IL-2 and IL-10 Genes to Inflammatory Bowel Disease (IBD) Susceptibility;" *Clin Exp. Immunol.*; Jul. 1998; 113 (1); 28-32; Abstract Only.

Peterson, R. L.; Wang, L.; Albert, L.; Keith, J. C., Jr.; and Dorner, A. J.; "Molecular Effects of Recombinant Human Interleukin-11 in the HLA-B27 Rat Model of Inflammatory Bowel Disease;" *Lab Invest*; Dec. 1998; 78 (12); 1503-1512; Abstract Only.

Phillips, R. J. and Powley, T. L.; "Gastric Volume Rather Than Nutrient Content Inhibits Food Intake;" *Am J Physiol*; Sep. 1996; 271 (3 Pt 2); R766-R769; Abstract Only.

Pimentel, M.; Chow, E. J.; and Lin, H. C.; "Normalization of Lactulose Breath Testing Correlates With Symptom Improvement In Irritable Bowel Syndrome. a Double-Blind, Randomized, Placebo-Controlled Study;" *Am J Gastroenterol.*; Feb. 2003; 98 (2); 412-419.

Pimentel, M.; Mayer, A. G.; Park, S.; Chow, E. J.; Hasan, A.; and Kong, Y.; "Methane Production During Lactulose Breath Test Is Associated With Gastrointestinal Disease Presentation;" *Dig. Dis. Sci.*; Jan. 2003: 48 (1); 86-92.

Pimentel, M.; Constantino, T.; Kong, Y.; Bajwa, M.; Rezaei, A.; and Park, S.; "A 14-Day Elemental Diet is Highly Effective in Normalizing the Lactulose Breath Test;" *Dig. Dis. Sci.*; Jan. 2004; 49 (1); 73-77.

Pimentel., M.; Wallace, D.; Hallegua, D.; Chow, E.; Kong, Y.; Park, S.; and Lin, H. C.; "A Link Between Irritable Bowel Syndrome and Fibromyalgia May Be Related To Findings on Lactulose Breath Testing;" *Ann. Rheum. Dis.*; Apr. 2004; 63 (4); 450-452.

Pironi, L.; Stanghellini, V.; Miglioli, M.; Corinaldesi, R.; De, Giorgio R.; Ruggeri, E.; Tosetti, C.; Poggioli, G.; Morselli Labate, A. M.; Monetti, N.; and .; "Fat-Induced Ileal Brake In Humans: a Dose-Dependent Phenomenon Correlated to the Plasma Levels of Peptide YY;" *Gastroenterology*; Sep. 1993; 105 (3); 733-739.

Poole, S.; Lorenzetti, B. B.; Cunha, J. M.; Cunha, F. Q.; and Ferreira, S. H.; "Bradykinin B1 and B2 Receptors, Tumour Necrosis Factor Alpha and Inflammatory Hyperalgesia;" *Br. J Pharmacol.*; Feb. 1999; 126 (3); 649-656; Abstract Only.

Prantera, C.; Zannoni, F.; Scribano, M. L.; Berto, E.; Andreoli, A.; Kohn, A.; and Luzi, C.; "An Antibiotic Regimen for the Treatment of Active Crohn's Disease: a Randomized, Controlled Clinical Trial of Metronidazole Plus Ciprofloxacin;" *Am J Gastroenterol.*; Feb. 1996; 91 (2); 328-332.

Propst, A.; Propst, T.; Herold, M.; Vogel, W.; and Judmaier, G.; "INterleukin-1 Receptor Antagonist in Differential Diagnosis of Inflammatory Bowel Diseases;" *Eur. J Gastroenterol. Hepatol.*; Nov. 1995; 7 (11); 1031-1036; Abstract Only.

Quinton, J. F.; Sendid, B.; Reumaux, D.; Duthilleul, P.; Cortot, A.; Grandbastien, B.; Charrier, G.; Targan, S. R.; Colombel, J. F.; and Poulain, D.; "Anti-*Saccharomyces cerevisiae* Mannan Antibodies Combined With Antineutrophil Cytoplasmic Autoantibodies in Inflammatory Bowel Disease: Prevalence and Diagnostic Role:" *Gut*; Jun. 1998; 42 (6): 788-791.

Radford-Smith, G. and Jewell, D. P.; "Cytokines and INflammatory Bowel Disease:" *Baillieres Clin Gastroenterol.*; Mar. 1996; 10 (1); 151-164; Abstract Only.

Read, N. W.; McFarlane, A.; Kinsman, R. I.; Bates, T. E.; Blackhall, N. W.; Farrar, G. B.; Hall, J. C.; Moss, G.; Morris, A. P.; O'Neill, B.; and .; "Effect of Infusion of Nutrient Solutions into the Ileum on Gastrointestinal Transit and Plasma Levels of Neurotensin and Enteroglucagon;" *Gastroenterology*; Feb. 1984; 86 (2); 274-280.

Reasbeck, P. G. and Van Rij, A. M.; "The Effect of somatostatin on Dumping After Gastric Surgery: a Preliminary Report;" *Surgery*; Apr. 1986; 99 (4); 462-468.

Redgrave, T. G. and Carlson, L. A.; "Changes in Plasma Very Low Density and Low Density Lipoprotein Content, Composition, and Size After a Fatty Meal in Normo- and Hypertriglycendemic Man;" *J Lipid Res.*; Feb. 1979; 20 (2); 217-229.

Reimund, J. M.; Allison, A. C.; Muller, C. D.; Dumont, S.; Kenney, J. S.; Baumann, R.; Duclos, B.; and Poindron, P.; "Antioxidants Inhibit the in Vitro Production of Inflammatory Cytokines in Crohn's Disease and Ulcerative Colitis;" *Eur. J Clin Invest*; Feb. 1998; 28 (2); 145-150; Abstract Only.

Rhodes, J. M.; Middleton, P.; and Jewell, D. P.; "The Lactulose Hydrogen Breath Test As a Diagnostic Test for Small-Bowel Bacterial Overgrowth;" *Scand. J Gastroenterol.*; 1979; 14 (3); 333-336; Abstract Only.

Riordan, S. M.; McIver, C. J.; Walker, B. M.; Duncombe, V. M.; Bolin, T. D.; and Thomas, M. C.; "The Lactulose Breath Hydrogen Test and Small Intestinal Bacterial Overgrowth;" *Am J Gastroenterol.*; Sep. 1996; 91 (9); 1795-1803; Abstract Only.

Riordan, S. M.; McIver, C. J.; Wakefield, D.; Bolin, T. D.; Duncombe, V. M.; and Thomas, M. C.; "Small Intestinal Bacterial Overgrowth in the Symptomatic Elderly;" *Am J Gastroenterol.*; Jan. 1997; 92 (1); 47-51.

Rogler, G. and Andus, T.; "Cytokines in Inflammatory Bowel Disease;" *World J Surg.*; Apr. 1998; 22 (4); 382-389; Abstract Only.

Rolak, L. A.; "The Diagnosis of Multiple Sclerosis;" *Neurol. Clin*; Feb. 1996; 14 (1); 27-43.

Rombeau, J. L. and Rolandelli, R. H.; "Enteral and Parenteral Nutrition in Patients With enteric Fistulas and Short Bowel Syndrome;" *Surg. Clin North Am*; Jun. 1987; 67 (3); 551-571.

Rowe, P. C. and Calkins, H.; "Neurally Mediated Hypotension and Chronic Fatigue Syndrome;" *Am J Med.*; Sep. 1998; 105 (3A); 15S-21S.

Ruemmele, F. M.; Targan, S. R.; Levy, G.; Dubinsky, M.; Braun, J.; and Seidman, E. G.; "Diagnostic Accuracy of Serological Assays in Pediatric Inflammatory Bowel Disease;" *Gastroenterology*; Oct. 1998; 115 (4); 822-829.

Ruseler-Van Embden, J. G. and Both-Patoir, H. C.; "Anaerobic Gram-Negative Faecal Flora in Patients With Crohn's Disease and Healthy Subjects;" *Antonie Van Leeuwenhoek*; Jun. 1983; 49 (2); 125-132; Abstract Only.

Rutgeerts, P.; Ghoos, Y.; Vantrappen, G.; and Eyssen, H.; "Small Bowel Bacterial Overgrowth, Ileal Dysfunction and Stool Fat Excretion in Patients With Unoperated Crohn's Disease;" *Gastroenterology*; 1979; 76 (5, part 2); 1232-.

Sahu, A.; Sninsky, C. A.; and Kalra, S. P.; "Evidence That Hypothalamic Neuropeptide Y Gene Expression and NPY Levels in the Paraventricular Nucleus Increase Before the Onset of Hyperphagia in Experimental Diabetes;" *Brain Res.*; May 1997; 755 (2); 339-342; Abstract Only.

Sahu, A.; "Evidence Suggesting That Galanin (GAL), Melanin-Concentrating Hormone (MCH), Neurotensin (NT), Proopiomelanocortin (POMC) and Neuropeptide Y (NPY) Are Targets of Leptin Signaling in the Hypothalamus;" *Endocrinology*; Feb. 1998; 139 (2); 795-798; Abstract Only.

Saiki, T.; Mitsuyama, K.; Toyonaga, A.; Ishida, H.; and Tanikawa, K.; "Detection of Pro- and Anti-Inflammatory Cytokines in Stools of Patients With Inflammatory Bowel Disease;" *Scand. J Gastroenterol.*; Jun. 1998; 33 (6); 616-622; Abstract Only.

Sakai, T.; Kusugami, K.; Nishimura, H.; Ando, T.; Yamaguchi, T.; Ohsuga, M.; Ina, K.; Enomoto, A.; Kimura, Y.; and Yoshikai, Y.; "Interleukin 15 Activity in the Rectal Mucosa of Inflammatory Bowel Disease;" *Gastroenterology*; Jun. 1998; 114 (6); 1237-1243; Abstract Only.

Sanger, G. J.; "5-Hydroxytryptamine and Functional Bowel Disorders;" *Neurogastroenterol. Motil.*; Dec. 1996; 8 (4); 319-331; Abstract Only.

Sanger, G. J.; "Hypersensitivity and Hyperreactivity in the Irritable Bowel Syndrome: An Opportunity for Drug Discovery;" *Dig. Dis.*; 1999; 17 (2); 90-99; Abstract Only.

Sanger, G. J.; Yoshida, M.; Yahyah, M.; and Kitazumi, K.; "Increased Defecation During Stress or After 5-Hydroxytryptophan: Selective Inhibition by the 5-HT(4) Receptor Antagonist, SB-207266;" *Br. J Pharmacol.*; Jun. 2000; 130 (3); 706-712; Abstract Only.

Santos, F. A. and Rao, V. S.; "Quinine-Induced Inhibition of Gastrointestinal Transit in Mice: Possible Involvement of Endogenous Opioids;" *Eur. J Pharmacol.*; Jan. 1999; 364 (2-3); 193-197; Abstract Only.

Sartor, R. B.; "Pathogenesis and Immune Mechanisms of Chronic Inflammatory Bowel Diseases;" *Am J Gastroenterol.*; Dec. 1997; 92 (12 Suppl); 5S-11S.

Saunders, D. R. and Sillery, J. K.; "Absorption of Triglyceride by Human Small Intestine: Dose-Response Relationships;" *Am J Clin Nutr.*; Oct. 1988; 48 (4); 988-991.

Schemann, M. and Ehrlein, H. J.; "The Utility of Cellulose Meals for Studies on Gastrointestinal Motility in Dogs;" *Digestion*; 1982; 25 (3); 194-196.

Schemann, M. and Ehrlein, H. J.; "Postprandial Patterns of Canine Jejunal Motility and Transit of Luminal Content;" *Gastroenterology*; Apr. 1986; 90 (4); 991-1000.

Schmidt, T.; Hackelsberger, N.; Widmer, R.; Meisel, C.; Pfeiffer, A.; and Kaess, H.; "Ambulatory 24-Hour Jejunal Motility in Diarrhea-Predominant Irritable Bowel Syndrome;" *Scand. J Gastroenterol.*; Jun. 1996; 31 (6); 581-589; Abstract Only.

Schneider, A.; Novis, B.; Chen, V.; and Leichtman, G.; "Value of the 14C-D-Xylose Breath Test in Patients With Intestinal Bacterial Overgrowth;" *Digestion*; 1985; 32 (2); 86-91.

Schreiber, S.; Heinig, T.; Thiele, H. G.; and Raedler, A.; "Immunoregulatory Role of Interleukin 10 in Patients With Inflammatory Bowel Disease;" *Gastroenterology*; May 1995; 10B (5); 1434-1444; Abstract Only.

Schreiber, S.; Heinig, T.; Panzer, U.; Reinking, R.; Bouchard, A.; Stahl, P. D.; and Raedler, A.; "Impaired Response of Activated Mononuclear Phagocytes to Interleukin 4 in Inflammatory Bowel Disease;" *Gastroenterolgy*; Jan. 1995; 108 (1); 21-33; Abstract Only.

Schreiber, S.; "Experimental Immunomodulatory Therapy of Inflammatory Bowel Disease;" *Neth. J Med.*; Dec. 1998; 53 (6); S24-S31; Abstract Only.

Sharpe, M.; "Cognitive Behavior Therapy for Chronic Fatigue Syndrome; Efficacy and Implications;" *Am J Med.*; Sep. 1998; 105 (3A); 104S-109S.

Shigematsu, S.; "Therapeutic Potential of Interleukin-1 Receptor Antagonist in Inflammatory Bowel Disease;" *Kurume Med. J*; 1998; 45 (2); 175-179; Abstract Only.

Shirachi, A.; "Therapeutic Implications of Interleukin-10 in Inflammatory Bowel Disease;" *Kurume Med. J*; 1998; 45 (1); 63-67; Abstract Only.

Siegle, M. L.; Schmid, H. R.; and Ehrlein, H. J.; "Effects of Ileal Infusions of Nutrients on Motor Partterns of Canine Small Intestine;" *Am J Physiol*; Jul. 1990; 259 (1 Pt 1); G78-G85.

Silberbauer, C. J.; Surina-Baumgartner, D. M.; Arnold, M.; and Langhans, W.; "Prandial Lactate Infusion Inhibits Spontaneous Feeding in Rats;" *Am J Physiol Regul. Integr. Comp Physiol*; Mar. 2000; 278 (3); R646-R653; Abstract Only.

Simansky, K. J.; Jakubow, J.; Sisk, F. C.; Vaidya, A. H.; and Eberle-Wang, K.; "Peripheral Serotonin Is an Incomplete Signal for Eliciting Satiety in Sham-Feeding Rats;" *Pharmacol. Biochem. Behav.*; Nov. 1992; 43 (3); 847-854; Abstract Only.

Simpson,J.W.; "Diet and Large Intestinal Disease in Dogs and Cats;" *Journal of Nutrition*; Dec. 1996; 128 (12 Suppl.); 2717S-2722S.

Smith, B. K.; York, D. A.; and Bray, G. A.; "Activation of Hypothalamic Serotonin Receptors Reduced Intake of Dietary Fat and Protein but Not Carbohydrate;" *Am J Physiol*; Sep. 1999; 277 (3 Pt 2); R802-R811; Abstract Only.

Soderholm, J. D.; Peterson, K. H.; Olaison, G.; Franzen, L. E.; Westrom; B.; Magnusson, K. E.; and SJODAHL, R.; "Epithelial Permeability to Proteins in the Noninflamed Ileum of Crohn's Disease?;" *Gastroenterology*; Jul. 1999; 117 (1); 65-72.

Soll, A.H.; "Medical Treatment of Peptic Ulcer Disease;" *JAMA*; Feb. 28, 1996; 275(8).

Soll,A.H.; "Concensus conference. Medical treatment of Peptic ulcer disease. Practice guidelines. Practice Parameters Committee of the American College of Gastroenterology;" *JAMA*; Feb. 28, 1996; 257(8); 622-629.

Soper, N. J.; Chapman, N. J.; Kelly, K. A.; Brown, M. L.; Phillips, S. F.; and Go, V. L.; "The 'Ileal Brake' After Ileal Pouch-Anal Anastomosis;" *Gastroenterology*; Jan. 1990; 98 (1); 111-116.

Spanhaak, S.; Havenaar, R.; and Schaafsma, G.; "The Effect of Consumption of Milk Fermented by Lactobacillus Casel Strain Shirota on the Intestinal Microflora and Immune Parameters in Humans;" *Eur. J Clin Nutr.*; Dec. 1998; 52 (12); 899-907; Abstract Only.

Sperber, A. D.; Carmel, S.; Atzmon, Y.; Weisberg, I.; Shalit, Y.; Neumann, L.; Fich, A.; Friger, M.; and Buskila, D.; "Use of the Functional Bowel Disorder Severity Index (FBDSI) in a Study of Patients With the Irritable Bowel Syndrome and Fibromyalgia;" *Am J Gastroenterol.*; Apr. 2000; 95 (4); 995-998.

Spiller, R. C.; Trotman, I. F.; Higgins, B. E.; Ghatei, M. A.; Grimble, G. K.; Lee, Y. C.; Bloom, S. R.; Misiewicz, J. J.; and Silk, D. B.; "The Ileal Brake—Inhibition of Jejunal Motility After Ileal Fat Perfusion in Man;" *Gut*; Apr. 1984; 25 (4); 365-274.

Spiller, R. C.; Trotman, I. F.; Adrian, T. E.; Bloom, S. R.; Misiewicz, J. J.; and Silk, D. B.; "Further Characterisation of the 'Ileal Brake' Reflexin Man—Effect of Ileal Infusion of Partial Digests of Fat, Protein, and Starch on Jejunal Motility and Release of Neurotensin, Enteroglucagon, and Peptide YY;" *Gut*; Aug. 1988; 29 (8); 1042-1051.

Stack, W. A.; Mann, S. D.; Roy, A. J.; Heath, P.; Sopwith, M.; Freeman, J.; Holmes, G.; Long, R.; Forbes, A.; and Kamm, M. A.; "Randomised Controlled Trial of CDP571 Antibody to Tumour Necrosis Factor-Alpha in Crohn's Disease;" *Lancet*; Feb. 1997; 349 (9051); 521-524; Abstract Only.

Starha, L. and Chalabala, M.; "[Oral Long-Acting Drugs. 8. Effects of Palmitic and Lauric Acid and Their Glycerine Esters on the Slowing of the Drug Release];" *Cesk. Farm.*; Sep. 1972; 21 (7); 311-314.

Steadman, C. J.; Talley, N. J.; Phillips, S. F.; and Zinsmeister, A. R.; "Selective 5-Hydroxytryptamine Type 3 Receptor Antagonism With Ondansetron As Treatment for Diarrhea-Predominant Irritable Bowel Syndrome: a Pilot Study;" *Mayo Clin Proc.*; Aug. 1992; 67 (8); 732-738; Abstract Only.

Steele, L.; Dobbins, J. G.; Fukuda, K.; Reyes, M.; Randall, B.; Koppelman, M.; and Reeves, W. C.; "The Epidemiology of Chronic Fatigue in San Francisco;" *Am J Med.*; Sep. 1998; 105 (3A); 83S-90S.

Stotzer, P. O.; Bjornsson, E. S.; and Abrahamsson, H.; "Interdigestive and Postprandial Motility in Small-Intestinal Bacterial Overgrowth;" *Scand. J Gastroenterol.*; Sep. 1996; 31 (9); 875-880; Abstract Only.

Strocchi, A.; Corazza, G.; Ellis, C. J.; Gasbarrini, G.; and Levitt, M. D.; "Detection of Malabsorption of Low Doses of Carbohydrate: Accuracy of Various Breath H2 Crileria;" *Gastroenterology*; Nov. 1993; 105 (5); 1404-1410; Abstract Only.

Summers, R. W.; Cramer, J.; and Flatt, A. J.; "Computerized Analysis of Spike Burst Activity in the Small Intestine;" *IEEE Trans. Biomed. Eng*; May 1982; 29 (5); 309-314.

Swanink, C. M.; Stolk-Engelaar, V. M.; Van Der Meer, J. W.; Vercoulen, J. H.; Bleijenberg, G.; Fennis, J. F.; Galama, J. M.; and Hoogkamp-Korstanje, J. A.; "Yersinia Enterocolitica and the Chronic Fatigue Syndrome;" *J infect.*; May 1998; 36 (3); 269-272; Abstract Only.

Swart, G. R. and Van Den Berg, J. W.; "13C Breath Test in Gastroenterological Practice;" *Scand. J Gastroenterol. Suppl*; 1998; 225 13-18; Abstract Only.

Swinard and Lowenthal; "Emulsifying and Suspending Agents;" 1985; 17 (68); 1296-1300.

Talley, N. J.; "Review Article: 5-Hydroxytryptamine Agonists and Antagonists in the Modulation of Gastrointestinal Motility and Sensation: Clinical Implications;" *Aliment. Pharmacol. Ther.*; Jun. 1992; 6 (3); 273-289; Abstract Only.

Targan, S. R.; Hanauer, S. B.; Van Deventer, S. J.; Mayer, L.; Present, D. H.; Braakman, T.; Dewoody, K. L.; Schaible, T. F.; and Rutgeerts, P. J.; "A Short-Term Study of Chimeric Monoclonal Antibody CA2 to Tumor Necrosis Factor Alpha for Crohn's Disease. Crohn's Disease CA2 Study Group;" *N. Engl. J Med.*; Oct. 1997; 337 (15); 1029-1035.

Targan, S. R.; "The Utility of ANCA and ASCA in Inflammatory Bowel Disease;" *Inflamm. Bowel. Dis.*; Feb. 1999; 5 (1); 61-63.

Terman, M.; Levine, S. M.; Terman, J. S.; and Doherty, S.; "Chronic Fatigue Syndrome and Seasonal Affective Disorder; Comorbidity, Diagnostic Overlap, and Implications for Treatment;" *Am J Med.*; Sep. 1998; 105 (3A); 115S-124S.

Tirelli, U.; Chierichetti, F.; Tavio, M.; Simonelli, C.; Bianchin, G.; Zanco, P.; and Ferlin, G.; "Brain Positron Emission Tomography (PET) in Chronic Fatigue Syndrome: Preliminary Data;" *Am J Med.*; Sep. 1998; 105 (3A); 54S-58S.

Triadafilopoulos, G.; Simms, R. W.; and Goldenberg, D. L.; "Bowel Dysfunction in Fibromyalgia Syndrome;" *Dig. Dis. Sci.*; Jan. 1991; 36 (1); 59-64.

Turton, M. D.; O'Shea, D.; Gunn, I.; Beak, S. A.; Edwards, C. M.; Meeran, K.; Choi, S. J.; Taylor, G. M.; Heath, M. M.; Lambert, P. D.; Wilding, J. P.; Smith, D. M.; Ghatei, M. A.; Herbert, J.; and Bloom, S. R.; "A Role for Glucagon-Like Peptide-1 in the Central Regulation of Feeding;" *Nature*; Jan. 1996; 379 (6560); 69-72; Abstract Only.

Van Den Berg, W. B.; "Joint Inflammation and Cartilage Destruction May Occur Uncoupled;" *Springer Semin. Immunopathol.*; 1998; 20 (1-2); 149-164; Abstract Only.

Van Dijk, G. and Thiele, T. E.; "Glucagon-Like Peptide-1 (7-36) Amide: a Central Regulator of Satiety and Interoceptive Stress;" *neuropeptides*; Oct. 1999; 33 (5); 406-414; Abstract Only.

Van Dullemen, H. M.; Van Deventer, S. J.; Hommes, D. W.; Bijl, H. A.; Jansenm J.; Tytgat, G. N.; and Woody, J.; "Treatment of Crohn's Disease With Anti-Tumor Necrosis Factor Chimeric Monoclonal Antibody (CA2);" *Gastroenterology*; Jul. 1995; 109 (1); 129-135; Abstract Only.

Van Hogezand, R. A. and Verspaget, H. W.; "Selective Immunomodulation in Patients With Inflammatory Bowel Disease-Future Therapy or Reality?;" *Neth. J Med.*; Feb. 1996; 48 (2); 64-67; Abstract Only.

Van Hogezand, R. A. and Verspaget, H. W.; "The Future Role of Anti-Tumour Necrosis Factor-Alpha Products in the Treatment of Crohn's Disease;" *Drugs*; Sep. 1998; 56 (3); 299-305; Abstract Only.

Vanderhoof, J. A. and Young, R. J.; "Use of Probiotics in Childhood Gastrointestinal Disorders;" *J Pediatr. Gastroenterol. Nutr.*; Sep. 1998; 27 (3); 323-332; Abstract Only.

Vanderhoof, J. A.; Young, R. J.; Murray, N.; and Kaufman, S. S.; "Treatment Strategies for Small Bowel Bacterial Overgrowth in Short Bowel Syndrome;" *J Pediatr. Gastroenterol. Nutr.*; Aug. 1998; 27 (2); 155-160; Abstract Only.

Varga, G.; Kordas, K.; Burghardt, B.; Gacsalyi, I.; and Szenasi, G.; "Effect of Deramciciane, a New 5-HT Receptor Antagonist, on Cholecystokinin-Induced Changes in Rat Gastrointestinal Function;" *Eur. J Pharmacol.*; Feb. 1999; 367 (2-3); 315-323; Abstract Only.

Varni, J. W.; Rapoff, M. A.; Waldron, S. A.; Gragg, R. A.; Bernstein, B. H.; and Lindsley, C. B.; "Chronic Pain and Emotional Distress in Children and Adolescents;" *J Dev. Behav. Pediatr.*; Jun. 1996; 17 (3); 154-161; Abstract Only.

Verkijk, M.; Gielkens, H. A.; Lamers, C. B.; and Masclee, A. A.; "Effect of Gastrin on Antroduodenal Motility: Role of Intraluminal Acidity;" *Am J Physiol*; Nov. 1998; 275 (5 Pt 1); G1209-G1216.

Voigt, J. P.; Fink, H.; and Marsden, C. A.; "Evidence for the Involvement of the 5-HT1A Receptor in CCK Induced Satiety in Rats;" *Naunyn Schmledebergs Arch. Pharmacol.*; Mar. 1995; 351 (3); 217-220; Abstract Only.

Voigt, J. P.; Kienzle, F.; Sohr, R.; Rex, A.; and Fink, H.; "Feeding and 8-OH-DPAT-Related Release of Serotonin in the Rat Lateral Hypothalamus;" *Pharmacol. Biochem. Behav.*; Jan. 2000; 65 (1); 183-189; Abstract Only.

Wade, P. R.; Tamir, H.; Kirchgessner, A. L.; and Gershon, M. D.; "Analysis of the Role of 5-HT in the Enteric Nervous System Using Anti-Idiotopic Antibodies to 5-HT Receptors;" *Am J Physiol*; Mar. 1994; 266 (3 Pt 1); G403-G416; Abstract Only.

Wade, P. R.; Chen, J.; Jaffe, B.; Kassem, I. S.; Blakely, R. D.; and Gershon, M. D.; "Localization and Function of a 5-HT Transporter in Crypt Epithelia of the Gastrointestinal Tract:" *J Neurosci.*; Apr. 1996; 16 (7); 2352-2364; Abstract Only.

Warnick, G. R.; "Enzymatic Methods for Quantification of Lipoprotein Lipids;" *Methods Enzymol.*; 1986; 129 101-123.

Way, Lawrence W.; "Current Surgical Diagnosis & Treatment;" 1991; 9 1083- Appleton & Lange (Norwalk, Connecticut).

Website Reference: Great Smokies Diagnostic Library (May 4, 1999).

Weckmann, A. L. and Cocer-Varela, J.; "Cytokine Inhibitors in Autoimmune Disease;" *Semin. Arthritis Rheum.*; Oct. 1996; 26 (2); 539-557; Abstract Only.

Welch, I. M.; Davison, P. A.; Worlding, J.; and Read, N. W.; "Effect of Ileal Infusion of Lipid on Jejunal Motor Patterns After a Nutrient and Nonnutrient Meal;" *Am J Physiol*; Dec. 1988; 255 (6 Pt 1); G800-G806.

Wellmann, W. and Schmidt, F. W.; "Intestinal Lavage in the Treatment of Crohn's Disease: A Pilot Study;" *Klinische Wochenschrift*; 1982; 60 (7); 371-374.

Whitehead, W. E.; Palsson, O.; and Jones, K. R.; "Systematic Review of the Comorbidity of irritable Bowel Syndrome With Other Disorders: What Are the Causes and Implications?;" *Gastroenterology*; Apr. 2002; 122 (4); 1140-1156.

Whiteside, T. L. and Friberg, D.; "Natural Killer Cells and Natural Killer Cell Activity in Chronic Fatigue Syndrome;" *Am J Med.*; Sep. 1998; 105 (3A); 27S-34S.

Wolf, B. W.; Wheeler, K. B.; Ataya, D. G.; and Garleb, K. A.; "Safety and Tolerance of Lactobacillus Reuteri Supplementation to a Population Infected With the Human Immunodeficiency Virus;" *Food Chem. Toxicol.*; Dec. 1998; 36 (12); 1085-1094; Abstract Only.

Wolf, G.; "Neuropeptides Responding to Leptin;" *Nutr. Rev.*; Mar. 1997; 55 (3); 85-88; Abstract Only.

Wolfe, F.; "Fibromyalgia: the Clinical Syndrome;" *Rheum. Dis. Clin North Am*; Feb. 1989; 15 (1); 1-18.

Wolfe, F.; Ross, K.; Anderson, J.; and Russell, I. J.; "Aspects of Fibromyalgia in the General Population: Sex, Pain Threshold, and Fibromyalgia Symptoms;" *J Rheumatol.*; Jan. 1995; 22 (1); 151-156.

Woo, P.; "Cytokines in Juvenile Chronic Arthritis;" *Baillieres Clin Rheumatol.*; May 1998; 12 (2); 219-228; Abstract Only.

Wu, A. L.; Clark, S. B.; and Holt, P. R.; "Transmucosal Triglyceride Transport Rates in Proximal and Distal Rat Intestine In Vivo;" *J Lipid Res.*; Jul. 1975; 16 (4); 251-257.

Wu, A. L. and Bennett, Clark S.; "Resistance of Intestinal Triglyceride Transport Capacity in the Rat to Adaptation to Altered Luminal Environment;" *Am J Clin Nutr.*; Feb. 1976; 29 (2); 157-168.

Wu, A. L.; Clark, S. B.; and Holt, P. R.; "Composition of Lymph Chylomicrons From Proximal or Distal Rat Small Intestine;" *Am J Clin Nutr*, Mar. 1980; 33 (3); 582-589.

Young, Graeme P.; "Colorectal Disorders: a Dietary Management Perspective;" *Asia Pacific J Clin Nutr*, 2000; 9 (Suppl); S76-S82.

Yuan, C. S.; Foss, J. F.; Osinski, J.; Toledano, A.; Roizen, M. F.; and Moss, J.; "The Safety and Efficacy of Oral Methylnaltrexone in Preventing Morphine-Induced Delay in Oral-Cecal Transit Time;" *Clin Pharmacol. Ther.*; Apr. 1997; 61 (4); 467-475; Abstract Only.

Yuan, C. S.; Foss, J. F.; O'Connor, M.; Osinski, J.; Roizen, M. F.; and Moss, J.; "Effects of Intravenous Methylnaltrexone on Opioid-Induced Gut Motility and Transit Time Changes in Subjects Receiving Chronic Methadone Therapy: a Pilot Study;" *Pain*; Dec. 1999; 83 (3); 631-635; Abstract Only.

Yuan, C. S.; Foss, J. F.; O'Connor, M.; Osinski, J.; Karrison, T.; Moss, J.; and Roizen, M. F.; "Methyinaltrexone for Reversal of Constipation Due to Chronic Methadone Use; a Randomized Controlled Trial;" *JAMA*; Jan. 2000; 283 (3); 367-372; Abstract Only.

Zhou, X. T.; Wang, L. J.; Elashoff, J. D.; and Lin, H. C.; "Fat in Distal Gut Inhibits Intestinal Transit More Potently Than Fat in Proximal Gut;" *Gastroenterology*; Apr. 1995; 108 (4); A714-; Abstract Only.

Zilversmit, D. B.; "Chylomicrons:" 1969; (C1); 329-368; Academic (New York, NY).

Zilversmit, D. B.; "Atherogenesis: a Postprandial Phenomenon;" *Circulation*; Sep. 1979; 60 (3); 473-485.

Adrian, T. E.; Ferri, G. L.; Bacarese-Hamilton, A. J.; Fuessl, H. S.; Polak, J. M.; and Bloom, S. R.; "Human Distribution and Release of a Putative New Gut Hormone, Peptide YY;" *Gastroenterology*; Nov. 1985; 89 (5); 1070-1077.

Pimentel,M. et al; "Eradication of Small Intestinal Bacterial Overgrowth Decreases the Gastrointestinal Symptoms in Fibromyalgia," *Gastroenterology*; Apr. 2000; 118 (4 Supl.2 Part 1); AGA p. A413.

Pimentel,M. et al; "Comparison of Peak Breath Hydrogen Production in Patients with Irritable Bowel Syndrome, Chronic Fatigue Syndrome and Fibromyalgia;" *Gastroenterology*; Apr. 2000; 118 (4 Supl.2 Part 1); AGA p. A413.

Pimentel,M. et al; "Eradication of Small Intestinal Bacterial Decreases Symptons in Fibromyalgia: A Double Blind Randomized Study;" *Arthritis & Rheumatism*; Nov. 13-14, 1999; 42 (9 Suppl.); S343; Abstract 1632.

Pimentel,M. et al; "Eradication of Small Intestinal Bacterial Overgrowth Decreases Symptoms in Chronic Fatigue Syndrome: A Double Blind, Randomized Study;" *Gastroenterology*; Apr. 2000; 118 (4 Supl.2 Part 1); AGA p. A414; *Arthritis & Rheumatism*; 1999; 42 (9 Suppl.); S343.

Pimentel,M. et al.; *The American Journal of Gastroenterology*; 2000; 95 (12); 3503-3506.

Pimentel,M. "Small Intestinal Bacterial Overgrowth: A Possible Association with Fibromyalgia;" *Journal of Musculoskeletal Pain*; 9(3).

Tatemoto, K. and Mutt, V.; "Isolation of Two Novel Candidate Hormones Using a Chemical Method for Finding Naturally Occurring Polypeptides 1;" *Nature*; Jun. 1980; 285 (5764); 417-418.

* cited by examiner

METHODS FOR MANIPULATING UPPER GASTROINTESTINAL TRANSIT, BLOOD FLOW, AND SATIETY, AND FOR TREATING VISCERAL HYPERALGESIA

This application is a division of U.S. patent application Ser. No. 09/837,797, filed Apr. 17, 2001, allowed, which is a continuation-in-part of U.S. patent application Ser. No. 09/374,142, filed on Aug. 11, 1999, and issued as U.S. Pat. No. 6,861,053 on Mar. 1, 2005, and also a continuation-in-part of U.S. patent application Ser. No. 09/374,143, filed on Aug. 11, 1999, and issued as U.S. Pat. No. 6,562,629 on May 11, 2003, and also a continuation-in-part of U.S. patent application Ser. No. 09/546,119, filed on Apr. 10, 2000 and issued as U.S. Pat. No. 6,558,708 on May 6, 2003, which is a continuation-in-part of U.S. patent application Ser. No. 09/420,046, filed Oct. 18, 1999, abandoned, which is a continuation-in-part of U.S. patent application Ser. No. 09/359,583, filed on Jul. 22, 1999, abandoned, which was a continuation of U.S. patent application Ser. No. 08/832,307, filed on Apr. 3, 1997 and issued as U.S. Pat. No. 5,977,175 on Nov. 2, 1999, which was a continuation of U.S. patent application Ser. No. 08/442,843, filed on May 17, 1995, abandoned, and claims priority to PCT applications; PCT/US01/1 1238 filed Mar. 07, 2001; PCT/US00/22168 filed Aug. 11, 2000; and PCT/US00/22030 filed Aug. 11, 2000.

FIELD OF THE INVENTION

The present invention relates to methods and pharmaceutical compositions for controlling the presentation of and response to lumenal content in the gastrointestinal tract.

BACKGROUND OF THE INVENTION

A principal function of the gastrointestinal tract is to process and absorb food. The stomach, which is both a storage and digestive organ, works to optimize the conditions for the digestion and absorption of food in the small intestine. Following the stomach and preceding the large bowel (colon) is the small intestine, which comprises three regions: the duodenum, jejunum, and ileum. A major function of the small intestine is one of absorption of digested nutrients.

The passage of a meal through the gastrointestinal tract, which leads to digestion and absorption of nutrients, is controlled by a complex system of inhibitory and stimulatory motility mechanisms which are set in motion by the composition of the meal ingested. Specific receptors for fats and proteins, and the osmolality, acidity and particle size of the meal activate propulsive and inhibitory reactions, which modulate transit and thus absorption. In normal human subjects, the mechanisms that regulate gastrointestinal transit can, under some circumstances, be sensitized or desensitized in response to the subject's recent dietary history. (K. M. Cunningham et al., *Gastrointestinal adaptation to diets of differing fat composition in human volunteers*, Gut 32(5): 483–86 [1991]).

The rate of transit through the small intestine is of great significance for the rate and extent of absorption from the small intestine. Disruption of the normal digestive and absorptive processes frequently manifests as a variety of syndromes, such as, malnutrition, weight loss, diarrhea, steatorrhea, vitamin deficiency, electrolyte imbalance, and the like. Chronic diarrhea is a common problem found in a variety of gastrointestinal disorders where water, solutes and nutrients are malabsorbed (Read, N. W., *Diarrhea motrice*, Clin. Gastroenterol. 15: 657–86 [1986]).

Specifically, conditions such as short bowel syndrome, postgastrectomy dumping and ileal resection can lead to symptoms such as postprandial distension, cramping, abdominal pain, gaseousness, nausea, palpitations, flushing, steatorrhea or weight loss. These symptoms can persist despite the use of anti-diarrheal medications, anticholinergic agents (Ivey, K J., *Are anticholinergics of use in the irritable bowel syndrome?*, Gastroenterology 68: 1300–07 [1975]), somatostatin analogues (Reasbeck P G, and A M Van Rij, *The effect of somatostatin on dumping after surgery: A preliminary report*, Surgery 1986; 99: 462–468 [1986]), conjugated bile acid replacement therapy (C. Gruy-Kapral et al., *Conjugated bile acid replacement therapy for short-bowel syndrome*, Gastroenterol. 116:15–21 [1999]), or large quantities of opiates (O'Brien, J. D. et al., *Effect of codeine and loperamide on upper intestinal transit and absorption in normal subjects and patients with postvagotomy diarrhea*, Gut 19: 312–18 [1988]). Additionally, even with treatment, fecal loss of water, solutes and nutrients can still be so excessive in some patients that long term use of parenteral fluids and nutrition can be required for survival (Rombeau, J. L. and R. H. Rolandelli, *Enteral and parenteral nutrition in patients with entericfistulas and short bowel syndrome*, Surg. Clin. North Am. 67:551–571 [1989]).

Abnormally slow gastrointestinal transit time can also have painful and serious consequences. Opioids (e.g., morphine), used for short-term or long-term pain management, commonly causes a slowing of gastrointestinal transit that can lead to bowel obstruction (ileus) or constipation. (E.g., Murthy, B. V. et al., *Intestinal pseudo-obstruction associated with oral morphine*, Eur. J. Anaesthesiol. 15(3):370–71 [1998]). Chronic constipation can result in complications including hemorrhoids, anal fissure, rectal prolapse, stercoral ulcer, melanosis coli, fecal impaction, fecal incontinence, ischemic colitis, colonic volvulus, colonic perforation, encopresis, and urinary retention. Delayed transit can also be a manifestation of a motility disorder such as idiopathic chronic intestinal pseudo-obstruction.

The small intestine is also an important site for the absorption of pharmacological agents. The proximal part of the small intestine has the greatest capacity for absorption of drugs. Intestinal absorption of drugs is influenced to a great extent by many of the same basic factors that affect the digestion and absorption of nutrients, water and electrolytes. Absorption of a drug in the gastrointestinal tract is a function of characteristics of the drug, such as its molecular structure, as well as attributes of the gastrointestinal tract. The rate of absorption of certain drugs, which are absorbed slowly and usually incompletely, varies according to the small intestinal transit time. Intestinal transit is important in the design of pharmaceutical preparations, especially when the absorption site of a drug is located in a particular segment of the gastrointestinal tract.

Many drugs and dosage formulations have been and continue to be developed because of the need to overcome the physiological and physicochemical limitations associated with drug delivery such as poor stability, short biological half-life, inefficient absorption and poor bioavailability. Applications of controlled release technology have moved towards control of absorption via regulation of the input to the gastrointestinal tract. However, recent pharmaceutical attempts to alter gastric emptying and small intestinal transit times have not been very successful. (Khosla and Davis, J. Pharm. Pharmacol. 39:47–49 [1987]; Davis et al., Pharm. Res. 3:208–213 [1986]).

For drug absorption to proceed efficiently, the drug must first arrive at a normal absorbing surface in a form suitable for absorption; it must remain there long enough in a form and in a concentration that enhance absorption; and it must be absorbed by a normal epithelial cell without being metabolized by that cell. Accordingly, considerable advantage would be obtained if a pharmaceutical dosage form could be retained for a longer period of time within the stomach and/or the small intestine for proper absorption to occur.

The period of time during which nutrients and/or drugs are in contact with the mucosa of the small intestine is crucial for the efficacy of digestion and absorption. Inadequate residence time can lead to fecal loss of nutrients and diarrhea. Therefore, modulation of the motility rate and transit time of nutrients and/or drugs through the gastrointestinal tract will ensure optimal utilization of the absorptive surface, as well as prevent transport mechanisms from being overloaded (which could occur if substrates were passed on too rapidly and exceeded the absorptive capacity of already maximally loaded surfaces in the small intestine).

The speed of transit through the small intestine is normally regulated by inhibitory mechanisms located in the proximal and distal small intestine known as the jejunal brake and the ileal brake. Inhibitory feedback is activated to slow transit when end products of digestion make contact with nutrient sensors of the small intestine. (E.g., Lin, H. C., U.S. Pat. No. 5,977,175; Dobson, C. L. et al., *The effect of oleic acid on the human ileal brake and its implications for small intestinal transit of tablet formulations*, Pharm. Res. 16(1):92–96 [1999]; Lin, H. C. et al., *Intestinal transit is more potently inhibited by fat in the distal (Ileal brake) than in the proximal (jejunal brake) gut*, Dig. Dis. Sci. 42(1): 19–25 [1997]; Lin, H. C. et al., *Jejunal brake: inhibition of intestinal transit by fat in the proximal small intestine*, Dig. Dis. Sci., 41(2):326–29 [1996a]).

Specifically, jejunal and ileal brakes slow transit by the release of gut peptides such as peptide YY and by the activation of neural pathways such as those involving endogenous opioids. (Lin, H. C. et al., *Fat-induced ileal brake in the dog depends on peptide YY*, Gastroenterol. 110(5):1491–95 [1996b]). Transit is then slowed by the stimulation of nonpropagative intestinal contractions which inhibit movement of the lumenal content. The removal or impairment of these inhibitory mechanisms can lead to abnormally rapid transit. For example, in patients with a history of resection of the terminal ileum, intestinal transit can become uncontrolled and abnormally accelerated when the ileal brake is no longer intact. Time for processing of food can then be so reduced that few end products of digestion are available to trigger the jejunal brake as the remaining inhibitory mechanism.

Peptide YY and its analogs or agonists have been used to manipulate endocrine regulation of cell proliferation, nutrient transport, and intestinal water and electrolyte secretion. (E.g., Balasubramaniam, *Analogs of peptide yy and uses thereof*, U.S. Pat. No. 5,604,203; WO9820885A1; EP692971A1; Croom et al., *Method of enhancing nutrient uptake*, U.S. Pat. No. 5,912,227; Litvak, D. A. et al., *Characterization of two novel proabsorptive peptide YY analogs, BIM-43073D and BIM-43004C*, Dig. Dis. Sci. 44(3):643–48 [1999]). A role for peptide YY in the regulation of intestinal motility, secretion, and blood flow has also been suggested, as well as its use in a treatment of malabsorptive disorders (Liu, C. D. et al., *Peptide YY: a potential proabsorbtive hormone for the treatment of malabsorptive disorders*, Am. Surg. 62(3):232–36 [1996]; Liu, C. D. et al., Intraluminal peptide YY induces colonic absorption in vivo, Dis. Colon Rectum 40(4):478–82 [1997]; Bilchik, A. J. et al., *Peptide YY augments postprandial small intestinal absorption in the conscious dog*, Am. J. Surg. 167(6): 570–74 [1994]).

Lin et al. immuno-neutralized peptide YY in vivo to block the ileal brake response and, thus, showed that it is mediated by peptide YY. (Lin, H. C. et al., *Fat-induced ileal brake in the dog depends on peptide YY*, Gastroenterology, 110(5): 1491–95 [1996b]). Serum levels of peptide YY increase during the ileal brake response to nutrient infusion into the distal ileum. (Spiller, R. C. et al., *Further characterisation of the 'ileal brake' reflex in man—effect of ileal infusion of partial digests of fat, protein, and starch on jejunal motility and release of neurotensin, enteroglucagon, and peptide YY*, Gut, 29(8):1042–51 [1988]; Pironi, L. et al., *Fat-induced ileal brake in humans: a dose-dependent phenomenon correlated to the plasma levels of peptide YY*, Gastroenterology, 105(3):733–9 [1993]; Dreznik, Z. et al., *Effect of ileal oleate on interdigestive intestinal motility of the dog*, Dig. Dis. Sci., 39(7):1511–8 [1994]; Lin, C. D. et al., *Interluminal peptide YY induces colonic absorption in vivo*, Dis. Colon Rectum, 40(4):478–82 [April 1997]). In contrast, in vitro studies have shown peptide YY infused into isolated canine ileum dose-dependently increased phasic circular muscle activity. (Fox-Threlkeld, J. A. et al., *Peptide YY stimulates circular muscle contractions of the isolated perfused canine ileum by inhibiting nitric oxide release and enchancing acetylcholine release*, Peptides, 14(6):1171–78 [1993]).

Kreutter et al. taught the use of $\beta_3$-adrenoceptor agonists and antagonists for the treatment of intestinal motility disorders, as well as depression, prostate disease and dyslipidemia (U.S. Pat. No. 5,627,200).

Bagnol et al. reported the comparative immunovisualization of mu and kappa opioid receptors in the various cell layers of the rat gastrointestinal tract, including a comparatively large number of kappa opioid receptors in the myenteric plexus (Bagnol, D. et al., *Cellular localization and distribution of the cloned mu and kappa opioid receptors in rat gastrointestinal tract*, Neuroscience, 81(2):579–91[1997]). They suggested that opioid receptors can directly influence neuronal activity in the gastrointestinal tract.

Kreek et al. taught the use of opioid receptor antagonists, such as naloxone, naltrexone, and nalmefene, for the relief of gastrointestinal dysmotility. (Kreek et al., Method for controlling gastrointestinal dysmotility, U.S. Pat. No. 4,987, 136). Riviere et al. taught the use of the opioid receptor antagonist fedotozine in the treatment of intestinal obstructions (Riviere, P. J. M. et al., U.S. Pat. No. 5,362,756). Opioid-related constipation, the most common chronic adverse effect of opioid pain medications in patients who require long-term opioid administration, such as patients with advanced cancer or participants in methadone maintenance, has been treated with orally administered methylnaltrexone and naloxone. (Yuan, C. S. et al., *Methylnaltrexone for reversal of constipation due to chronic methadone use: arandomized controlled trial*, JAMA 283(3):367–72 [2000]; Meissner, W. et al., *Oral naloxone reverses opioid-associated constipation*, Pain 84(1):105–9 [2000]; Culpepper-Morgan, J. A., et al., *Treatment of opioid-induced constipation with oral naloxone: a pilot study*, Clin. Pharmacol. Ther. 52(1):90–95 [1992]; Yuan, C. S. et al., *The safety and efficacy of oral methylnaltrexone in preventing morphine-induced delay in oral-cecal transit time*, Clin. Pharmacol. Ther. 61(4):467–75 [1997]; Santos, F. A. et al., *Quinine-induced inhibition of gastrointestinal transit in mice: pos-*

*sible involvement of endogenous opioids*, Eur. J. Pharmacol., 364(2–3):193–97 [1999]. Naloxone was also reported to abolish the ileal brake in rats (Brown, N. J. et al., *The effect of an opiate receptor antagonist on the ileal brake mechanism in the rat*, Pharmacology, 47(4):230–36 [1993]).

Receptors for 5-Hydroxytryptamine (5-HT), also known as serotonin, have been localized on various cells of the gastrointestinal tract. (Gershon, M. D., *Review article: roles played by 5-hydroxytryptamine in the physiology of the bowel*, Aliment. Pharmacol. Ther., 13 Suppl 2:15–30 [1999]; Kirchgessner, A. L. et al., *Identification of cells that express 5-hydroxytryptamine 1A receptors in the nervous systems of the bowel and pancreas*, J. Comp. Neurol., 15:364(3): 439–455 [1996]). Brown et al. reported that subcutaneous administration of 5-HT3 receptor antagonists, granisetron and ondansetron, in rats delayed intestinal transit of a baked bean meal but abolished the ileal brake induced by ileal infusion of lipid. They postulated the presence of 5-HT3 receptors on afferent nerves that initiate reflexes that both accelerate and delay intestinal transit. (Brown, N. J. et al., *Granisetron and ondansetron: effects on the ileal brake mechanism in the rat*, J. Pharm. Pharmacol. 45(6):521–24 [1993]). Kuemmerle et al. reported neuro-endocrine 5-HT-mediation of motilin-induced accelerated gastrointestinal motility. (Kuemmerle, J. F. et al., *Serotonin neural receptors mediate motilin-induced motility in isolated, vascularly perfused canine jejunum*, J. Surg. Res., 45(4):357–62 [1988]).

5-HT is a mediator for the so-called "peristaltic reflex" in the mammalian colon, which mediates colonic evacuation. (E.g., Grider, J. R. et al., *5-Hydroxytryptamine4 receptor agonists initiate the peristaltic reflex in human, rat, and guinea pig intestine*, Gastroenterology, 115(2):370–80 [1998]; Jin, J. G. et al., *Propulsion in guinea pig colon induced by 5-hydroxytryptamine (HT) via 5-HT4 and 5-HT3 receptors*, J. Pharmacol. Exp. Ther., 288(1):93–97 [1999]; Foxx-Orenstein, A. E. et al., *5-HT4 receptor agonists and delta-opioid receptor antagonists act synergistically to stimulate colonic propulsion*, Am J. Physiol., 275(5 Pt. 1):G979–83 [1998]; Foxx-Orenstein, A. E., *Distinct 5-HT receptors mediate the peristaltic reflex induced by mucosal stimuli in human and guinea pig intestine*, Gastroenterology 111(5): 1281–90 [1996]; Wade, P. R. et al., *Localization and function of a 5-HT transporter in crypt epithelia of the gastrointestinal tract*, J. Neurosci., 16(7):2352–64 [1996]).

The intestinal response to 5-HT has been best described in terms of the peristaltic reflex in in vitro models. Bulbring and Crema first showed that luminal 5-HT resulted in peristalsis (Bulbring et al., J. Physiol. 140:381–407 [1959]; Bulbring et al., Brit. J. Pharm. 13:444–457 [1958]). Since the stimulation of peristalsis by 5-HT was unaffected by extrinsic denervation (Bulbring et al., QJ Exp. Physiol. 43:26–37 [1958]), the peristaltic reflex was considered to be intrinsic to the enteric nervous system. Using a modified Trendelenburg model that compartmentalized the peristaltic reflex into the sensory limb, the ascending contraction limb (orad to stimulus) and the descending relaxation limb (aborad to stimulus), Grider, et al. reported that (1) mucosal stimulation but not muscle stretch released 5-HT to activate a primary sensory neuron to release calcitonin gene-related peptide (CGRP)(Grider et al., Am. J. Physiol. 270: G778–G782 [1996]) via 5-HT4 receptors in humans and rats (also 5-HT1p in rats) and 5-HT3 receptors in guinea pigs; (2) cholinergic interneurons are then stimulated by CGRP to initiate both ascending contraction via an excitatory motor neuron that depends on substances P and K and acetylcholine (Grider et al., Am. J. Physiol. 257:G709–G714 [1989]) and descending relaxation (Grider, Am. J. Physiol. 266: G1139–G1145 [1994]; Grider et al. [1996], Jin et al., J. Pharmacol. Exp. Ther. 288:93–97 [1999]) via an inhibitory motor neuron that depends on pituitary adenylate cyclase-activating peptide (PACAP), nitric oxide and vasoactive inhibitory peptide (VIP)(Grider et al., Neuroscience 54:521–526 [1993]; Grider et al., J. Auton. Nerv. Syst. 50:151–159 [1994]); and (3) peristalsis is controlled by [a]an opioid pathway that inhibits descending relaxation by suppressing the release of VIP; [b] a somatostatin pathway that inhibits this opioid pathway (Grider, Am. J. Physiol. 275:G973–G978 [1998]); and [c] a GABA (Grider, Am. J. Physiol. 267:G696–G701 [1994]) and a gastrin releasing peptide (GRP) (Grider, Gastroenterol. 116:A1000 [1999]) pathway that stimulate VIP release. An opioid pathway that inhibits the excitatory motor neurons responsible for ascending contraction has also been described (Gintzler et al., Br. J. Pharmacol. 75:199–205 [1982]; Yau et al., Am. J. Physiol. 250:G60–G63 [1986]). These observations are consistent with neuroanatomic and electrophysiological observations.

In addition, mucosal stroking has been found to induce 5-HT release by intestinal mucosal cells, which in turn activates a 5-HT4 receptor on enteric sensory neurons, evoking a neuronal reflex that stimulates chloride secretion (Kellum, J. M. et al., *Stroking human jejunal mucosa induces 5-HT release and Cl⁻ secretion via afferent neurons and 5-HT4 receptors*, Am. J. Physiol. 277(3 Pt 1):G515–20 [1999]).

Agonists of 5-HT⅘, 5-HT3 receptors, as well as opioid Δ receptor antagonists, were reported to facilitate peristaltic propulsive activity in the colon in response to mechanical stroking, which causes the endogenous release of 5-HT and calcitonin gene-related protein (CGRP) in the stroked mucosal area. (Steadman, C. J. et al., *Selective 5-hydroxytrypamine type 3 receptor antagonism with ondansetron as treatment for diarrhea-predominant irritable bowel syndrome: a pilot study*, Mayo Clin. Proc. 67(8):732–38 [1992]). Colonic distension also results in CGRP secretion, which is associated with triggering the peristaltic reflex.

On the other hand, gastric distension is thought to be one of many factors inducing satiety and/or suppressing the rate of ingestion. (Bergstrom, J., *Mechanism of uremic suppression of appetite*, J. Ren. Nutr. 9(3):129–32 [1999]; Phillips, R. J. and Powley, T. L., *Gastric volume rather than nutrient content inhibits food intake*, Am. J. Physiol. 271(3 Pt 2);R766–69 [1996]; Pappas, T. N. et al., *Gastric distension is a physiologic satiety signal in the dog*, Dig. Dis. Sci. 34(10:1489–93 [1989]; Lepionka, L. et al., *Proximal gastric distension modifies ingestion rate in pigs*, Reprod. Nutr. Dev. 37(4):449–57 [1997]; McHugh, P R. and Moran, T. H., *The stomach, cholecystokinin, and satiety*, Fed. Proc. 45(5): 1384–90 [1986]; Lin, H. C. et al., *Frequency of gastric pacesetter potential depends on volume and site of distension*, Am. J. Physiol. 270(3 Pt 1):G470–5 [1996c]).

Another factor thought to contribute to satiety is glucagon-like peptide-1 (7–36) amide (GLP-1), which is processed from proglucagon in the distal ileum as well as in the central nervous system. In the periphery, GLP-1 acts as an incretin factor (inducer of insulin secretion) and profoundly inhibits upper gastrointestinal motility (e.g., ileal brake), the latter function presumably involving the central nervous system (Turton, M. D. et al., *A role for glucagon-like peptide-1 in the central regulation of feeding*, Nature 379 (6560):69–72 [1996]; Dijk, G. and Thiele, T. E., *Glucagon-like peptide-1 (7–36) amide: a central regulator of satiety and interoceptive stress*, Neuropeptides 33(5):406–414 [1999]). Within the central nervous system, GLP-1 has a satiating effect, since administration of GLP-1 into the third cerebral ventricle reduces short-term food intake (and meal size), while administration of GLP-1antagonists have the opposite effect (Dijk, G. and Thiele [1999]; but see, Asarian, L. et al., *Intracerebroventicular glucagon-like peptide-1 (7–36) amide inhibits sham feeding in rats without eliciting satiety*, Physiol. Behav. 64(3):367–72 [1998]). Lactate is another putative satiety factor. (Silberbauer, C. J. et al., *Prandial lactate infusion inhibits spontaneous feeding in rats*, Am. J. Physiol. Regul. Integr. Comp. Physiol. 278(3): R646–R653 [2000]). Meyer taught a method for controlling appetite involving the delivery to the ileum of food grade nutrients, including sugars, free fatty acids, polypeptides, amino acids for controlling satiety (Meyer, J. H., *Composition and method for inducing satiety*, U.S. Pat. No. 5,753,253).

Satiety can also be regulated by cytokines, such as IL-1, which is thought to operate directly on the hypothalamus or, alternatively, to increase the synthesis of tryptophan (Laviano, A. et al., *Peripherally injected IL-1 induces anorexia and increases brain tryptophan concentrations*, Adv. Exp. Med. Biol. 467:105–08 [1999]). Tryptophan is a precursor of 5-HT, which is itself a peripheral satiety signal, which has been thought to be acting through an afferent vagal nerve pathway. (E.g., Faris P. L. et al., *Effect of decreasing afferent vagal activity with ondansetron on symptoms of bulimia nervosa: a randomised, double-blind trial*, Lancet 355(9206):792–97 [2000]; Kitchener, S. J. and Dourish, C. T., *An examination of the behavioral specificity of hypophagia induced by 5-HT1B, 5-HT1C and 5-HT2 receptor agonist using the post-prandial satiety sequence in rats*, Psychopharmacology (Berl) 113(3–4):369–77 [1994]; Simansky, K. J. et al., *Peripheral serotonin is an incomplete signal for eliciting satiety in sham-feeding rats*, Pharmacol. Biochem. Behav. 43(2):847–54 [1992]; Edwards, S. and Stevens, R., *Peripherally administered 5-hydroxytryptamine elicits the full behavioural sequence of satiety*, Physiol. Behav. 50(5):1075–77 [1991]).

There may also be some interactions between 5-HT receptor-mediated effects and cholecystokinin-mediated effects on satiety. (Voight, J. P. et al., *Evidence for the involvement of the 5-HT1A receptor in CKK induced satiety in rats*, Nauyn Schmiedebergs Arch. Pharmacol. 351(3):217–20 [1995]; Varga, G. et al., *Effect of deramciclane, a new 5-HT receptor antagonist, on cholecystokinin-induced changes in rat gastrointestinal function*, Eur. J. Pharmacol. 367(2-3):315–23 [1999]; but see, Eberle-Wang, K. and Simansky, K. J., *The CKK-A receptor antagonist, devazepide, blocks the anorectic action of CKK but not peripheral serotonin in rats*, Pharmacol. Biochem. Behav. 43(3):943–47 [1992]). The neuropeptide hormone cholecystokinin is known to induce satiety, inhibit gastric emptying, and to stimulate digestive pancreatic and gall bladder activity. (Blevins, J. E. et al., *Brain regions where cholecystokinin suppresses feeding in rats*, Brain Res. 860(1-2):1–10 [2000]; Moran, T. H. and McHugh, P. R., *Cholecystokinin suppresses food intake by inhibiting gastric emptying*, Am. J. Physiol. 242(5):R491–97 [1982]; McHugh, P R. and Moran, T. H. [1986]; Takahashi, H. et al., *Composition for digestion of protein*, JP5246846A).

Cholecystokinin, and other neuropeptides, such as bombesin, amylin, proopiomelanocortin, corticoptropin-releasing factor, galanin, melanin-concentrating hormone, neurotensin, agouti-related protein, leptin, and neuropeptide Y, are important in the endocrine regulation of energy homeostasis. (Maratos-Flier, E., *Promotion of eating behavior*, U.S. Pat. No. 5,849,708; Inui, A., *Feeding and body-weight regulation by hypthalamic neuropeptides-mediation of the actions of leptin*, Trends Neurosci. 22(2):62–67 [1999]; Bushnik, T. et al., *Influence of bombesin on threshold for feeding and reward in the rat*, Acta Neurobiol. Exp. (Warsz) 59(4):295–302 [1999]; Sahu, A., *Evidence suggesting that galanin (GAL), melanin-concentrating hormone (MCH), neurotensin (NT), proopiomelanocotin (POMC) and neuropeptide Y (NPY) are targets of leptin signaling in the hypothalamus*, Endocrinol. 139(2):795–98 [1999]). Many of these neuropeptides are multi-functional, binding several different receptors at different sites in the body. For example, neuropeptide Y (NPY), a 36-amino-acid peptide widely expressed in the brain is a potent appetite inducing signal molecule as well as a mitogen and a vasoconstrictor active in cardiovascular homeostatis. (Kokot, F. and Ficek, R., *Effects of neuropeptide Y on appetite*, Miner. Electrolyte Metab. 25(4–6):303–05 [1999]).

Neuropeptide Y (NPY) and other neuropeptides may be involved in alternative biochemical satiety-regulating cascades within the hypothalamus. (E.g., King, P. J. et al., *Regulation of neuropeptide Y release from hypothalamic slices by melanocortin-4 agonists and leptin*, Peptides 21(1):45–48 [2000]; Hollopeter G. et al., *Response of neuropeptide Y-deficient mice to feeding effectors*, Regul. Pept. 75–76:383–89 [1998]). Bruno et al. taught a method of regulating appetite and metabolism in animals, including humans, which involves inter alia administering a composition that modulates synthesis and secretion of neuropeptide Y. (Bruno, J. F. et al., U.S. Pat. No. 6,013,622). Moreover, the neuropeptide Y-leptin endocrine axis has been considered a central mechanism of satiety regulation in mammals. Neuropeptide Y and leptin have opposite effects in the arcuate-paraventricular nucleus (ARC-PVN) of the hypothalamus, with leptin being satiety-inducing and a suppressor of neuropeptide Y (and agouti-related protein) expression. (E.g., Baskin, D. G. et al., *Leptin sensitive neurons in the hypothalamus*, Horm. Metab. Res. 31(5):345–50 [1999]). In phenotypically obese mice with an ob/ob genotype, adipose cells fail to secrete leptin, and neuropeptide Y is overexpressed in the hypothalamus. (Erickson, J. C. et al., *Attenuation of the obesity syndrome of ob/ob mice by the loss of neuropeptide Y*, Science 274(5293):1704–07 [1996]).

Neuropeptide Y mediates its effects through binding to Y1, Y2, Y4, and Y5 G-protein-coupled receptors on the surfaces of cells of the ARC-PVN of the hypothalamus. (Naveilhan, P. et al., *Normal feeding behavior, body weight and leptin response require the neuropeptide Y Y2 receptor*, Nat. Med. 5(10):1188–93 [1999]; King, P. J. et al., *Regulation of neuropeptide Y release by neuropeptide Y receptor ligands and calcium channel antagonists in hypothalamic slices*, J. Neurochem. 73(2):641–46 [1999]). Peptide YY can also bind to these receptors. In addition, Y1, Y2, Y4/PP1, Y5 and Y5/PP2/Y2 receptors for peptide YY are localized in myenteric and submuscosal nerve cell bodies, endothelial cells, and endocrine-like cells of the rat intestinal tract. (Jackerott, M. et al., *Immunocytochemical localization of the NPY/PYY Y1 receptor in enteric neurons, endothelial cells, and endocrine-like cells of the rat intestinal tract*, J. Histochem Cytochem., 45(12): 1643–50 (December 1997); Mannon, P. J. et al., *Peptide YY/neuropeptide Y Y1 receptor expression in the epithelium and mucosal nerves of the human colon*, Regul. Pept., 83(1): 11–19 [1999]). But until now, a way of manipulating satiety has been unknown that exploits linkages between afferent and efferent neural pathways with the hypothalamic endocrine regulation of satiety and post-prandial visceral blood flow.

A treatment for visceral hyperalgesia or hypersensitivity is also a desideratum. Visceral hyperalgesia, or pain hypersensitivity, is a common clinical observation in small intestinal bacterial overgrowth (SIBO), Crohn's disease, and irritable bowel syndrome (IBS). As many as 60% of subjects with IBS have reduced sensory thresholds for rectal distension compared to normal subjects. (H. Mertz et al., *Altered rectal perception is a biological marker of patients with the irritable bowel syndrome*, Gastroenterol.109:40–52 [1995]). While the experience of pain is intertwined with a person's emotions, memory, culture, and psychosocial situation (D. A. Drossman and W. G. Thompson, *Irritable bowel syndrome: a graduated, multicomponent treatment approach*, Ann. Intern. Med. 116:1009–16 [1992]) and the etiology for this hyperalgesia has remained elusive, evidence shows that certain cytokine mediated-immune responses can influence the perception of pain. Cytokines, including IL-1 ($\alpha$ and $\beta$), IL-2, IL-6, and TNF-$\alpha$, can be released in response to a variety of irritants and can modulate the perception of pain, possibly through the mediation of kinin $B_1$ and/or $B_2$ receptors (see, M. M. Campos et al., *Expression of $B_1$ kinin receptors mediating paw oedema formalin-induced nociception. Modulation by glucocorticoids*, Can. J. Physiol. Pharmacol. 73:812–19 [1995]; R. O. P. de Campos et al., *Systemic treatment with Mycobacterium bovis bacillus calmett-guerin (BCG) potentiates kinin $B_1$ receptor agonist-induced nociception and oedema formation in the formalin test in mice*, Neuropeptides 32(5):393–403 [1998]). Cytokine and neuropeptide levels are altered in IBS. An increase in substance P (neuropeptide)-sensitive nerve endings has been observed in subjects with IBS. (X. Pang et al., *Mast cell substance P-positive nerve involvement in a patient with both irritable bowel syndrome and interstitial cystitis*, Urology 47:436–38 [1996]). It has also been hypothesized that there is a sensitization of afferent pathways in IBS. (E. A. Mayer et al., *Basic and clinical aspects of visceral hyperalgesia*, Gastroenterol 1994;107:271–93 [1994]; L. Bueno et al., *Mediators and pharmacology of visceral sensitivity: from basic to clinical investigations*, Gastroenterol. 112:1714–43 [1997]).

In summary, a need exists for manipulating upper gastrointestinal transit and post-prandial visceral blood flow, by which absorption of ingested nutrients and/or drugs in the small intestine can be optimized to prevent and/or reduce ineffectiveness thereof due to malabsorption and to enhance the bioavailability and effectiveness of drugs. A need also exists to manipulate satiety and to treat visceral hyperalgesia, by which optimal nutritional intake and visceral comfort can be achieved. Through a unifying conception of visceral neural regulatory pathways, the present invention satisfies these needs and provides related advantages as well.

SUMMARY OF THE INVENTION

The present invention takes advantage of a novel understanding of the peripheral neural connections that exist between the enteric nervous system of the upper gastrointestinal tract, including an intrinsic serotonergic neural pathway, and the vertebral ganglia, and thence to the central nervous system. The present invention provides a means to enhance region-to region (e.g., gut-to-CNS or gut-to gut) communications by way of replicating 5-HT as a signal (or releasing 5-HT at a distance as a surrogate signal). Thus, the present invention provides a way to increase 5-HT in locations in the central nervous by transmitting a neural signal from the gut, or to transmit a 5-HT-mediated neural signal originating in one location in the gut via an intrinsic cholinergic afferent neural pathway to a second distant location in the gut where a serotonergic signal of the same or greater intensity is replicated.

The present technology, therefore, allows bi-directional neurally mediated modulation of the rate of upper gastrointestinal transit, feelings of satiety, visceral pain perception, and post-prandial visceral blood flow in a mammalian subject, such as a human. The present invention allows the artificially directed transmission and/or amplification of nervous signals from one location in the enteric nervous system to another via a prevertebral ganglion, bypassing the central nervous system, or alternatively to artificially direct nervous signal transmission from the enteric nervous system to the central nervous system, including the hypothalamus, and back again. The invention takes advantage of an intrinsic serotonergic neural pathway involving an intrinsic cholinergic afferent neural pathway that projects from peptide YY-sensitive primary sensory neurons in the intestinal wall to the prevertebral celiac ganglion. The prevertebral celiac ganglion is in turn linked by multiple prevertebral ganglionic pathways to the central nervous system, to the superior mesenteric ganglion, to the inferior mesenteric ganglion, and also back to the enteric nervous system via an adrenergic efferent neural pathway that projects from the prevertebral celiac ganglion to one or more enterochromaffincells in the intestinal mucosa and to serotonergic interneurons that are, in turn, linked in the myenteric plexus or submucous plexus to opioid interneurons. The opioid interneurons are in turn linked to excitatory and inhibitory motoneurons. The opioid interneurons are also linked by an intestino-fugal opioid pathway that projects to the prevertebral celiac ganglion, with one or more neural connections therefrom to the central nervous system, including the spinal cord, brain, hypothalamus, and pituitary, and projecting back from the central nervous system to the enteric nervous system.

In particular, the present invention includes a method of manipulating the rate of upper gastrointestinal transit of a substance in a mammal, whether the substance be a food or drug. The method involves administering by an oral or enteral delivery route a pharmaceutically acceptable composition comprising an active agent to the mammal's upper gastrointestinal tract. Depending on the desired results, the active agent to be selected can be an active lipid; a serotonin, serotonin agonist, or serotonin re-uptake inhibitor; peptide YY or a peptide YY functional analog; calcitonin gene-related peptide or a functional analog thereof; an adrenergic agonist; an opioid agonist; a combination of any of any of these; or an antagonist of a serotonin receptor, peptide YY receptor, adrenoceptor, opioid receptor, and/or calcitonin gene-related peptide (CGRP) receptor.

If it is desired to slow the rate of upper gastrointestinal transit, the active agent is an active lipid; a serotonin, serotonin agonist, or serotonin re-uptake inhibitor; peptide YY or a peptide YY functional analog; CGRP or a CGRP functional analog; an adrenergic agonist; an opioid agonist; or a combination of any of any of these, which is delivered in an amount and under conditions such that the cholinergic intestino-fugal pathway, at least one prevertebral ganglionic pathway, the adrenergic efferent neural pathway, the serotonergic interneuron and/or the opioid interneuron are activated thereby. This is also the basis for the inventive method for prolonging the residence time of an orally or enterally administered substance by promoting its dissolution, bioavailability and/or absorption in the small intestine.

Alternatively, if it is desired to accelerate the rate of upper gastrointestinal transit, then an antagonist of a serotonin receptor, peptide YY receptor, adrenoceptor, opioid receptor, CGRP receptor, or a combination of any of these is delivered in an amount and under conditions such that the cholinergic intestino-fugal pathway, at least one prevertebral ganglionic pathway, the adrenergic efferent neural pathway, the serotonergic interneuron and/or the opioid interneuron are blocked thereby.

The invention also includes a method of manipulating satiety in a mammalian subject. The method involves administering a pharmaceutically acceptable composition comprising an active agent by an oral or enteral delivery route to the mammal's upper gastrointestinal tract. Depending on the desired results, the active agent to be selected can be an active lipid; a serotonin, serotonin agonist, or serotonin re-uptake inhibitor; peptide YY or a peptide YY functional analog; CGRP or a CGRP functional analog; an adrenergic agonist; an opioid agonist; a combination of any of any of these; or an antagonist of a serotonin receptor, peptide YY receptor, CGRP receptor; adrenoceptor and/or opioid receptor.

If it is desired to induce a feeling of satiety in the subject, for example in cases of obesity, the active agent is an active lipid; a serotonin, serotonin agonist, or serotonin re-uptake inhibitor; peptide YY or a peptide YY functional analog; calcitonin gene-related peptide or a functional analog; CGRP or a CGRP functional analog; an adrenergic agonist; an opioid agonist; or a combination of any of these, which is delivered in an amount and under conditions such that the cholinergic intestino-fugal pathway, at least one prevertebral ganglionic pathway, the adrenergic efferent neural pathway, the serotonergic interneuron and/or the opioid interneuron are activated thereby.

If it is desired to suppress satiety in the subject, for example in cases of wasting such as are seen among cancer patients, the active agent is an antagonist of a serotonin receptor, peptide YY receptor, a CGRP receptor; an adrenoceptor, opioid receptor, or a combination of any of these receptor antagonists, delivered in an amount and under conditions such that the cholinergic intestino-fugal pathway, at least one prevertebral ganglionic pathway, the adrenergic efferent neural pathway, the serotonergic interneuron and/or the opioid interneuron are blocked thereby.

Similarly, an inventive method of treating visceral pain or visceral hypersensitivity in a human subject method involves administering an active agent by an oral or enteral delivery route to human subject. The active agent is selected from among antagonists of serotonin receptors; peptide YY receptors; CGRP receptors; adrenoceptors; and opioid receptors, and is delivered in an amount and under conditions such that activation of a cholinergic intestino-fugal pathway, prevertebral ganglionic pathways, gangalion to central nervous system pathways, the adrenergic efferent neural pathway, the serotonergic interneuron and/or the opioid interneuron is blocked by the action of the active agent. The sensation of esophageal, gastric, biliary, intestinal, colonic or rectal pain experienced by the human subject is thereby reduced. The method is of benefit, for example, in treating some irritable bowel syndrome (IBS) patients who experience visceral pain and/or hypersensitivity.

The present invention further provides methods and pharmaceutically acceptable compositions for enhancing the bioavailability and therapeutic effectiveness of drugs.

These and other advantages and features of the present invention will be described more fully in a detailed description of the preferred embodiments which follows. In further describing the invention, the disclosures of related applications U.S. Ser. Nos. 09/420,046; 09/359,583; 08/832,307 and 08/442,843 are incorporated by reference.

DETAILED DESCRIPTION OF THE INVENTION

Figure 1:
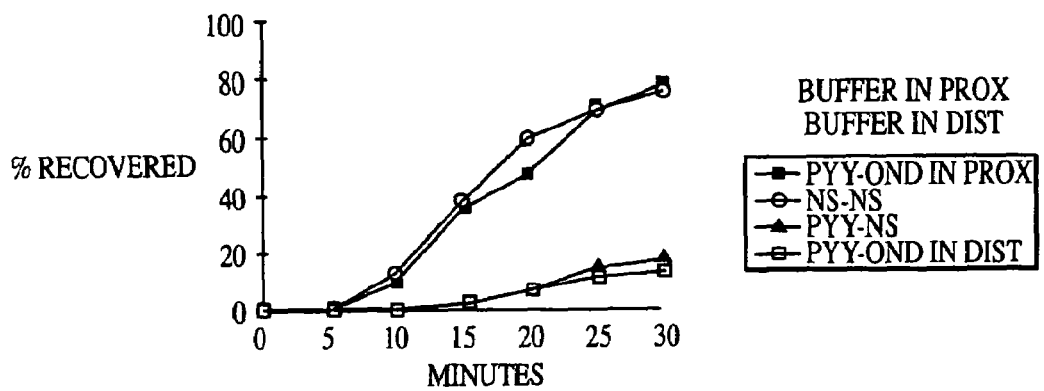
FIG. 1 demonstrates that slowing of the rate of intestinal transit by fat depends on peptide YY (PYY), which is a physiological fat signal molecule.

The upper gastrointestinal tract includes the entire alimentary canal, except the cecum, colon, rectum, and anus. While some digestive processes, such as starch hydrolysis, begin in the mouth and esophagus, of particular importance as sites of digestion are the stomach and small intestine, which includes the duodenum, jejunum, and the ileum. Important steps in dietary lipid absorption begin in the stomach, where an intricate control system of inhibitory and stimulatory motility mechanisms are set in motion by the composition of the meal ingested. These mechanisms prevent too rapid emptying of gastric contents into the duodenum, which would overwhelm its capacity for lipid or fat absorption. Such preventative mechanisms ensure a maximum interface of the water-insoluble lipid with the aqueous contents of the intestinal tract.

The next step in absorption of fats or lipids (terms used herein interchangeably) occurs upon their entry into the small intestine. In the early portion of the small intestine, specific receptors for fats and proteins, and the osmolality, acidity and the particle size of the meal activate propulsive and inhibitory reactions (i.e., ileal braking), which modulate their transit and absorption. The rate of passage through the small intestine (i.e., intestinal transit time) is of great significance for the rate and extent of absorption from the small intestine.

In the duodenum, the fats which have been released from the stomach encounter bile acids and pancreatic enzymes. The function of the bile acids is to render soluble the insoluble triglyceride molecules.

The intestinal absorption of lipids is normally very efficient over wide ranges of dietary fat intake. A normal person generally absorbs approximately 95–98% of dietary lipid. When the normal digestive and absorptive processes are impaired, malabsorption syndromes frequently ensue. The inventive method of manipulating upper gastrointestinal transit is useful for optimizing the digestive and absorptive processes for any individual mammal, including humans, and excepting ruminants such as camels, deer, antelopes, goats, sheep, and cattle.

Malabsorption syndromes include a large heterogeneous group of gastrointestinal disorders with the common characteristic of failure to assimilate ingested substances normally. The defect is characterized by decreased or impaired function of almost any organ of the gut, including the liver, biliary tract, pancreas, and lymphatic system, as well as the intestine. The clinical manifestations can vary from a severe symptom complex of rapid intestinal transit, dumping syndrome, diarrhea, weight loss, distention, steatorrhea, and asthenia to symptoms of specific nutrient deficiencies (i.e., malnutrition).

Examples of gastrointestinal disorders that frequently manifest as one or more malabsorption syndromes are postgastrectomy syndrome, dumping syndrome, AIDS-associated chronic diarrhea, diabetes-associated diarrhea, postvagotomy diarrhea, bariatric surgery-associated diarrhea (including obesity surgeries: gastric bypass, gastroplasties and intestinal bypass), short bowel syndrome (including resection of the small intestine after trauma, radiation induced complications, Crohn's disease, infarction of the intestine from vascular occlusion), tube-feeding related diarrhea, chronic secretory diarrhea, carcinoid syndrome-associated diarrhea, gastrointestinal peptide tumors, endocrine tumors, chronic diarrhea associated with thyroid disorders, chronic diarrhea in bacterial overgrowth, chronic diarrhea in gastrinoma, choleraic diarrhea, chronic diarrhea in giardiasis, antibiotic-associated chronic diarrhea, diarrhea-predominant irritable bowel syndrome, chronic diarrhea associated with maldigestion and malabsorption, chronic diarrhea in idiopathic primary gastrointestinal motility disorders, chronic diarrhea associated with collagenous colitis, surgery-associated acute diarrhea, antibiotic-associated acute diarrhea, infection-associated acute infectious diarrhea, and the like.

The rate at which food passes through the gastrointestinal tract is an important factor that affects the absorptive capacity and the outcome following gastric surgery and/or intestinal resection. Resection of extensive sections of bowel as well as loss of absorptive surface secondary to diseased small bowel mucosa can lead to specific malabsorption syndromes. Resection or disease of large amounts of terminal ileum are known to cause vitamin B12 and bile acid deficiencies, which, in turn, can lead to fat and other fat-soluble substances being less well absorbed. Bypassed loops of bowel, created by either surgery or fistula formation, and strictures can result in blind loop syndromes with bacterial overgrowth and subsequent malabsorption.

Malnutrition is a common problem in patients with inflammatory bowel diseases such as, for example, Crohn's disease or ulcerative colitis. Weight loss is found in 70–80% of patients with Crohn's disease and 18–62% of patients with ulcerative colitis.

The role of nutritional support as a primary therapy for inflammatory bowel diseases is not well established. Given the natural history of inflammatory bowel diseases, with frequent relapses and spontaneous remissions, and the difficulty and variability in quantifying disease activity, it has been difficult to design clinical trials that definitively establish the role of nutrition as a primary therapy for inflammatory bowel diseases. The use of elemental diets as primary therapy for inflammatory bowel diseases has also been examined. Parenteral nutrition and elemental diets appear to have limited roles in the long-term treatment of patients with inflammatory bowel diseases.

Short bowel syndrome generally refers to a condition in which less than 150 cm of remaining small bowel is associated with a massive loss of absorptive capacity. It is characterized by severe diarrhea and malabsorption. Patients with short bowel syndrome often experience malabsorption of protein, carbohydrate and fat resulting in calorie depletion and steatorrhea.

The most important therapeutic objective in the management of short bowel is to maintain the patient's nutritional status. By necessity, it is achieved primarily by parenteral nutrition support in the early postoperative period. Enteral nutrition support can be started early after operation when the ileus has resolved. Maximization of enteral absorption of nutrients is important for long-term survival. Generally, such maximization requires that the enteral intake greatly exceed the absorptive needs to ensure that the nutritional requirements are met.

Functional pancreatic insufficiency can also cause steatorrhea after gastric resection. Steatorrhea is the presence of excess fat in the feces. It is usually caused by a defect in gastrointestinal digestion and/or absorption. Steatorrhea rarely exists without malabsorption of other substances. For example, conditions such as osteomalacia related to calcium and vitamin D deficiency or anemia due to selective iron or B12 deficiencies are often associated with the malabsorption that occurs with steatorrhea. Weight loss occurs because of a loss of nutrients and energy. Diarrhea is another major symptom associated with steatorrhea. It is present in 80–97% of patients with malabsorption.

Dumping syndrome is one of the most common causes of morbidity after gastric surgery. This syndrome is characterized by both gastrointestinal and vasomotor symptoms. Gastrointestinal symptoms include postprandial fullness, crampy abdominal pain, nausea, vomiting and explosive diarrhea. Vasomotor symptoms include diaphoresis, weakness, dizziness, flushing, palpitations, and an intense desire to lie down. Patients with severe dumping symptoms may limit their food intake to minimize symptoms and as a result lose weight and become malnourished. In severe cases, as a last resort surgical treatment of dumping syndrome has been utilized.

Pharmaceutical treatment for severe dumping includes octreotide acetate (Sandoz), a long acting somatostatin analogue, which has been used with some success. Octreotide is administered subcutaneously and acts to slow gastric emptying, inhibit insulin release, and decrease enteric peptide secretion. Octreotide, unfortunately, is accompanied by several complications, which include injection site pain, tachyphylaxis, iatrogenic diabetes, malabsorption and cholelithiasis.

Diarrhea is a common problem after any abdominal operation. Treatment includes simple dietary changes, opiates and/or opioid-type drugs such as Lomotil or paregoric, antidiarrheal agents such as Diasorb (attapulgite), Donnagel (kaolin, hydroscyamine sulfate, atropine sulfate and scopalamine hydrobromide), Kaopectate, Motofen (difenoxin hydrochloride and atropine sulfate) and Pepto-Bismol for inhibitory effect on intestinal transit. Each modality of treatment, however, has had limited success and with the exception of dietary changes, all have negative side effects associated with use.

Diarrhea is a common problem in motility disorders of the gastrointestinal tract, such as in diarrhea-predominant irritable bowel syndrome, small intestinal bacterial overgrowth and diabetes.

Diarrhea is also a common complication associated with enteral feeding. Multiple etiologies for diarrhea are postulated, and its genesis may be a multifactorial process (Edes et al., *Am. J. Med.* 88:91–93 (1990). Causes include concurrent use of antibiotics or other diarrhea-inducing medications, altered bacterial flora, formula composition, rate of infusion, hypoalbuminemia, and enteral formula contamination. The composition of formula can also affect the incidence of diarrhea. The use of fiber-containing formulas to control diarrhea related to tube feeding is unsettled (Frankenfield et al., *Am. J. Clin. Nutr.* 50:553–558 [1989]).

Ileus or bowel obstruction are common complications associated with the long-term administration of opioid drugs such as morphine, heroin, opium, codeine, or methadone. In addition, ileus is a common post-operative complication that often prevents the resumption of feeding.

Satiety encompasses a lack of appetite for food or a cessation of food-seeking or food-ingesting behavior. Thus, satiety is a desirable state in conditions in which food intake is preferably curtailed, such as obesity. Alternatively, it can be desirable to suppress a state of satiety in conditions of anorexia or cachexia resulting from causes including illness, starvation, or chemotherapy.

Visceral hyperalgesia encompasses excessive or abnormal sensitivity to visceral sensations that are not normally consciously perceived, including hypersensitivity approaching a level of discomfort or pain. Visceral hyperalgesia is a common feature of SIBO, IBS, or Crohn's disease, which can severely impinge on a person's quality of life and nutritional state.

Techniques such as Doppler utrasonography and phase-contrast magnetic resonance imaging have made it possible to record blood flow to the gastrointestinal tract through the superior mesenteric artery directly and continuously in unanaesthetized, healthy humans. Several research groups have demonstrated how blood flow to the gastrointestinal tract increases gradually and markedly after a meal, and more so after a big meal than after a small one. The increase in post-prandial blood flow reaches its maximum after 20–40 minutes and lasts for 1.5–2 hours. In the postprandial period there is a parallel and similar increase in cardiac output; the meal thus imposes an increased work load on the heart.

The normal postprandial response is important to effective digestion and nutrient absorption. However, abnormally low postprandial visceral blood flow is a common complication of conditions such as insulin resistance in adults or of phototherapy in infants. (E.g., Summers, L. K. et al., *Impaired post-prandial tissue regulation of blood flow in insulin resistance: determinant of cardiovascular risk?*, Atherosclerosis 147(1):11–15 [1999]; Pezatti, M. et al., *Changes in mesenteric blood flow response to feeding: conventional versus fiber-optic phototherapy*, Pediatrics 105 (2):350–53 [2000]). On the other hand, abnormally increased visceral or gastrointestinal blood flow is a feature of ulcerative colitis and cirrhosis, which at the very least places abnormal stress on the heart. (E.g., Ludwig, D. et al., *Mesenteric blood flow is related to disease activity and risk of relapse in ulcerative colitis: a perspective follow-up study*, Gut 45(4):546–52 [1999]; Sugano, S. et al., *Azygous venous blood flow while fasting, postprandially, after endoscopic variceal ligation, measured by magnetic resonance imaging*, J. Gastroenterol. 34(3):310–14 [1999]). The present invention provides a method of manipulating postprandial visceral blood flow to optimize digestion and absorption and treat other pathological complications related to abnormal blood flow.

A tremendous amount of research has been undertaken in attempting to elucidate the role of nutrition and absorption in gastrointestinal disorders. Despite this research, few standards of care presently exist for the use of nutrition and absorption in most aspects of these disorders.

Accordingly, the present invention provides a method of manipulating upper gastrointestinal transit, whether to slow it to prolong the residence time of a substance in the small intestine of a subject for an amount of time sufficient for digestion and absorption of the substance to occur therein, or whether to accelerate upper gastrointestinal transit, for example, in subjects experiencing delayed transit resulting from the administration of opioid medications.

In order to optimally digest and absorb fat, intestinal transit is slowed by this nutrient in a dose-dependent fashion as the fat-induced jejunal brake (Lin, H. C. et al. [1996a]) and ileal brake (Lin, H. C. et al., *Intestinal transit is more potently inhibited by fat in the distal [ileal] brake than in the proximal [jejunal] brake*, Dig. Dis. Sci. 42:19–25 [1996d]). To achieve these responses, the sensory nerves of the small intestine must detect and respond to the fat in the intestinal lumen. Sensory nerves that respond specifically to the presence of fat in the lumen (fat-sensitive primary sensory neurons) are found in the lamina propria, separated from the intestinal lumen by the mucosa. Since these fat-sensitive sensory nerves do not have access to the lumen (Mei, N., *Recent studies on intestinal vagal efferent innervation. Functional implications*, J. Auton. Nerv. Syst. 9:199–206 [1983]; Melone, J., *Vagal receptors sensitive to lipids in the small intestine of the cat*, J. Auton. Nerv. Syst. 17:231–241 [1986]), one or more intermediary signals must be available. PYY is a signal for fat (Lin, H. C. et al., *Slowing of intestinal transit by fat in proximal gut depends on peptide YY*, Neurogastroenterol. Motility 10:82 [1998]; Lin, H. C. et al. [1996b]) and is released in response to fat in the lumen of the can or distal gut. Intestinal cells such as those that release PYY, do have direct access to the luminal content and serve as an intermediary signal-transmitting link between luminal fat and the fat-sensitive primary sensory neurons in the lamina propria.

Serotonin or 5-hydroxytryptamine (5-HT) from enterochromaffin cells (ECC) also has this signaling role. 5-HT is also produced by serotonergic interneurons of the myenteric plexus (Gershon, M. D., *The enteric nervous system*, Annu. Rev. Neurosci. 4:227–272 [1981]; Gershon, M. D. et al., *Serotonin: synthesis and release from the myenteric plexus of the mouse intestine*, Science 149:197–199 [1965]; Holzer, P. and Skotfitsch, G., *Release of endogenous 5-hydroxytryptamine from the myenteric plexus of the guinea-pig isolated small intestine*, Br. J. Pharmacol. 81:381–86 [1984]).

In addition to mediating neural signal transmission in the intrinsic serotonergic neural pathway, the release of 5-HT can occur as a result of activation of an extrinsic neural pathway consisting of a cholinergic afferent nerve and an adrenergic efferent nerve (Kunze, W. A. et al., *Intracellular recording of from myenteric neurons of the guinea-pig ileum* that responds to stretch, J. Physiol. 506:827–42 [1998]; Smith, T. K. and Furness, J. B., *Reflex changes in circular muscle activity elicited by stroking the mucosa: an electrophysiological analysis in the isolated guinea-pig ileum*, J. Auton. Nerv. Syst. 25:205–218 [1988]). Although the location of this extrinsic neural pathway is currently unknown, the extrinsic nerves going back and forth between the gut and the prevertebral ganglia (Bayliss, W. M. and Starling, E. H., *The movement and innervation of the small intestine*, J. Physiol. 24:99 [1899], Kosterlitz, H. W. and Lees, G. M., *Pharmacological analysis on intrinsic intestinal reflexes*, Pharmacol. Rev. 16:301–39 [1964]; Kuemmerle, J. F. and Makhlouf, G. M., *Characterization of of opioid receptors in intestinal muscle cells by selective radioligands and receptor protection*, Am. J. Physiol. 263:G269-G276 [1992]; Read, N. W. et al., *Transit of a meal through the stomach, small intestine, and colon in normal subjects and its role in the pathogenesis of diarrhea*, Gastroenterol. 79:1276–82 [1980]) are likely candidates since these nerves allow different regions of the gut to communicate and also consist of a cholinergic afferent and an adrenergic efferent. In accordance with the inventive methods, the release of 5-HT by a signal projecting from one part of the intestine to another via extrinsic nerves provides a relay mechanism for the slowing of transit through the proximal gut by the fat-induced ileal brake or through the distal gut by the fat-induced jejunal brake.

The pharmaceutically acceptable composition comprises the active agent, and is formulated to deliver the active agent to a desired section of the upper gastrointestinal tract. The inventive pharmaceutically acceptable compositions also comprise a pharmaceutically acceptable carrier. Optionally, a drug or other substance to be absorbed can be included in the same composition, or alternatively can be provided in a separate formulation.

In some preferred embodiments, the pharmaceutically acceptable composition includes the active agent in a dose and in a form effective to prolong the residence time of an orally or enterally administered substance by slowing the transit of the substance through the small intestine for an amount of time sufficient for absorption of said substance to occur therein.

The invention contemplates a range of optimal residence times which are dependent upon the character of the substance (i.e., nutrients, drugs). As used herein, "substance" encompasses the lumenal content of the gastrointestinal tract which includes, for example, digested and partially digested foods and nutrients, dissolved and/or solubilized drugs as well as incompletely dissolved and/or solubilized forms thereof, electrolyte-containing lumenal fluids, and the like.

The small intestinal residence time for optimal absorption of digested foods and nutrients can be calculated using an average orocecal transit time as a reference. The normal orocecal transit time is approximately 2–3 hours in the fasted state. The inventive composition should target an intestinal residence within the same average time frame of approximately 2–3 hours.

The pharmaceutical industry has published a great deal of information on the dissolution time for individual drugs and various compounds. Such information is found in the numerous pharmacological publications which are readily available to those of skill in the art. For example, if the in vitro model for dissolution and release of drug "X" is 4 hours, then the small intestinal residence time for optimal absorption of drug "X" would be at least 4 hours and would also include additional time allowing for gastric emptying to occur in vivo. Thus, for drugs, the appropriate residence time is dependent on the time for release of the drug.

As used herein, "digestion" encompasses the process of breaking down large molecules into their smaller component molecules.

As used herein, "absorption" encompasses the transport of a substance from the intestinal lumen through the barrier of the mucosal epithelial cells into the blood and/or lymphatic systems.

As used herein, a drug is a chemotherapeutic or other substance used to treat a disorder, abnormal condition, discomfort, wound, lesion, or injury, of a physical, biochemical, mental, emotional or affective nature. Examples of drugs include, but are not limited to, somatostatin analogues, insulin release inhibitors, anti-diarrheal agents, antibiotics, fiber, electrolytes, analgesics, antipyretics, migraine treatment, migraine prophylaxis, antifungal agents, antiviral agents, Quinolones, AIDS therapeutic agents, anti-infectives, aminoglycosides, antispasmodics, parasympathomimetics, anti-tuberculous agents, anti-malarial agents, accines, anti-parasitic agents, cephalosporins, macrolides, azalides, tetracyclines, penicillins, anti-arthritic therapy agents, gout therapy agents, nonsteroidal anti-inflammatory agents, gold compounds, antianemic agents, antianginal agents, antiarrhythmics, anticoagulants, post-MI agents, vasodilators, beta-adrenergic blockers, calcium channel blockers, nitrates, thrombolytic agents, anticoagulants, antifibrolytic agents, hemorrheologic agents, antiplatelet agents, vitamins, antihemophilic agents, heart failure agents, ACE inhibitors, cardiac glycosides, blood flow modifying agents, bile salts, growth promoting agents, growth suppressive agents, sympathomimetics, inotropic agents, antihypertensive agents, central alpha-adrenergic agonists, peripheral vasodilator, sympatholytics, diuretics, diuretic combinations, mineral supplements, hypolipedemic agents, acne treatments, antidiarrheal agents, antinauseants, antiemetics, antispasmodics, antiulcer, antireflux agents, appetite suppressants, appetite enhancers, gallstone-dissolving agents, gastrointestinal anti-inflammatory agents, antacids, antiflatulents, anti-gas agents, laxatives, stool softeners, digestants, digestive enzymes, enzyme supplements, Alzheimer's therapy, anticonvulsants, antiparkinson agents, sedatives, benzodiazepines, benzodiazepine receptor antagonists, receptor agonists, receptor antagonists, interferons, immunosuppressive therapy, immunomodulatory agents, muscle relaxants, hypnotics, antianxiety agents, antimanic agents, antidepressants (e.g., tricyclic antidepressants, such as amitryptaline (Elavil); tetracyclic antidepressants, such as maprotiline; serotonin re-uptake inhibitors, such as Prozac or Zoloft; monoamine oxidase inhibitors, such as phenelzine; and miscellaneous antidepressants, such as trazadone, venlafaxine, mirtazapine, nefazodone, or bupropion [Wellbutrin]), antiobesity agents, behavior modifiers, psychostimulants, neurostimulants, abuse deterrents, anxiolytics (e.g., benzodiazepine compounds, such as Librium, Atavin, Xanax, Valium, Tranxene, and Serax, or other anxiolytic agents such as Paxil), antipsychotics, antianaphylactic agents, antihistamines, antipruritics, anti-inflammatory agents, bronchodilators, antiasthmatic agents, cystic fibrosis therapy agents, mast-cell stabilizers, steroids, xanthines, anticholinergic agents, bioactive peptides, polypeptides, hormones, drugs acting at neuroeffector junctional sites, prostaglandins, narcotics, hypnotics, alcohols, psychiatric therapy agents, anti-cancer chemotherapy agents, drugs affecting motility, oral hypoglycemics, androgens, estrogens, nutriceuticals, herbal medications, insulin, serotonin receptor agonist, serotonin receptor antagonists, alternative medicines, amino acids, dietary supplements, analeptic agents, respiratory agents, cold remedies, cough suppressants, antimycotics, bronchodilators, constipation aids, contraceptives, decongestants, expectorants, motion sickness products, homeopathic preparations.

In one preferred embodiment, a major function of the inventive compositions is to slow gastrointestinal transit and control gastrointestinal intestinal residence time of a substance to enable substantial completion of lumenal and mucosal events required for absorption of the substance to occur in the small intestine. Of equal significance is the function of the inventive compositions to control the presentation of a substance to a desired region of the small intestine for absorption.

In another preferred embodiment, the inventive pharmaceutically acceptable compositions limit the presentation of a substance to the proximal region of the small intestine for absorption.

Depending on the desired results, useful active agents include, active lipids; serotonin, serotonin agonists, or serotonin re-uptake inhibitors; peptide YY or peptide YY functional analogs; CGRP or CGRP functional analogs; adrenergic agonists; opioid agonists; or a combination of any of any of these; antagonists of serotonin receptors, peptide YY receptors, adrenoceptors, opioid receptors, CGRP receptors, or a combination of any of these. Also useful are antagonists of serotonin receptors, peptide YY receptors, CGRP receptors; adrenoceptors and/or opioid receptors.

Serotonin, or 5-hydroxytryptamine (5-HT) is preferably used at a dose of 0.005–0.75 mg/kg of body mass. Serotonin agonists include HTF-919 and R-093877; Foxx-Orenstein, A. E. eta 1., Am. J. Physiol. 275(5 Pt 1):G979–83 [1998]). Serotonin re-uptake inhibitors include Prozac or Zoloft.

Serotonin receptor antagonists include antagonists of 5-HT3,5-HT1P, 5-HT1A, 5-HT2, and/or 5-HT4 receptors. Examples include ondansetron or granisetron, 5HT3 receptor antagonists (preferred dose range of 0.04–5 mg/kg), deramciclane (Varga, G. et al., *Effect of deramciclane, a new 5-HT receptor antagonist, on cholecystokinin-induced changes in rat gastrointestinal function*, Eur. J. Pharmacol. 367(2-3):315–23 [1999]), or alosetron. 5-HT4 receptor antagonists are preferably used at a dose of 0.05–500 picomoles/kg.

Peptide YY (PYY) and its functional analogs are preferably delivered at a dose of 0.5–500 picomoles/kg. PYY functional analogs include PYY (22–36), BIM-43004 (Liu, CD. et al., J. Surg. Res. 59(1):80–84 [1995]), BIM-43073D, BIM-43004C (Litvak, D. A. et al., Dig. Dis. Sci. 44(3): 643–48 [1999]). Other examples are also known in the art (e.g., Balasubramaniam, U.S. Pat. No. 5,604,203).

PYY receptor antagonists preferably include antagonists of Y4/PP1, Y5 or Y5/PP2/Y2, and most preferably Y1 or Y2. (E.g., Croom et al., U.S. Pat. No. 5,912,227) Other examples include BIBP3226, CGP71683A (King, P. J. et al., J. Neurochem. 73(2):641–46 [1999]).

CGRP receptor antagonists include human CGRP(8–37) (e.g., Foxx-Orenstein et al., Gastroenterol. 111(5):1281–90 [1996]).

Adrenergic agonists include norepinephrine.

Adrenergic or adrenoceptor antagonists include β-adrenoceptor antagonists, including propranolol and atenolol. They are preferably used at a dose of 0.05–2 mg/kg.

Opioid agonists include delta-acting opioid agonists (preferred dose range is 0.05–50 mg/kg, most preferred is 0.05–25 mg/kg); kappa-acting opioid agonists (preferred dose range is 0.005–100 microgram/kg); mu-acting opioid agonists (preferred dose range is 0.05–25 microgram/kg); and episilon-acting agonists. Examples of useful opioid agonists include deltorphins (e.g., deltorphin II and analogues), enkephalins (e.g., [d-Ala(2), Gly-ol(5)]-enkephalin [DAMGO]; [D-Pen(2,5)]-enkephalin [DPDPE]), dinorphins, trans-3,4-dichloro-N-methyl-N-[2-(1-pyrrolidinyl) cyclohexyl-]benzeneacetamide methane sulfonate (U-50, 488H), morphine, codeine, endorphin, or β-endorphin.

Opioid receptor antagonists include mu-acting opioid antagonists (preferably used at a dose range of 0.05–5 microgram/kg); kappa opioid receptor antagonists (preferably used at a dose of 0.05–30 mg/kg); delta opioid receptor antagonists (preferably used at a dose of 0.05–200 microgram/kg); and epsilon opioid receptor antagonists. Examples of useful opioid receptor antagonists include naloxone, naltrexone, methylnaltrexone, nalmefene, H2186, H3116, or fedotozine, i.e., (+)-1-1 [3,4,5-trimethoxy)benzyloxymethyl]-1-phenyl-N,N-dimethylpropylamine. Other useful opioid receptor antagonists are known (e.g., Kreek et al., U.S. Pat. No. 4,987,136).

The active agents listed above are not exhaustive but rather illustrative examples, and one skilled in the art is aware of other useful examples.

As used herein, "active lipid" encompasses a digested or substantially digested molecule having a structure and function substantially similar to a hydrolyzed end-product of fat digestion. Examples of hydrolyzed end products are molecules such as diglyceride, monoglyceride, glycerol, and most preferably free fatty acids or salts thereof.

In a preferred embodiment, the active agent is an active lipid comprising a saturated or unsaturated fatty acid. Fatty acids contemplated by the invention include fatty acids having between 4 and 24 carbon atoms.

Examples of fatty acids contemplated for use in the practice of the present invention include caprolic acid, caprulic acid, capric acid, lauric acid, myristic acid, oleic acid, palmitic acid, stearic acid, palmitoleic acid, linoleic acid, linolenic acid, trans-hexadecanoic acid, elaidic acid, columbinic acid, arachidic acid, behenic acid eicosenoic acid, erucic acid, bressidic acid, cetoleic acid, nervonic acid, Mead acid, arachidonic acid, timnodonic acid, clupanodonic acid, docosahexaenoic acid, and the like. In a preferred embodiment, the active lipid comprises oleic acid.

Also preferred are active lipids in the form of pharmaceutically acceptable salts of hydrolyzed fats, including salts of fatty acids. Sodium or potassium salts are preferred, but salts formed with other pharmaceutically acceptable cations are also useful. Useful examples include sodium- or potassium salts of caprolate, caprulate, caprate, laurate, myristate, oleate, palmitate, stearate, palmitolate, linolate, linolenate, trans-hexadecanoate, elaidate, columbinate, arachidate, behenate, eicosenoate, erucate, bressidate, cetoleate, nervonate, arachidonate, timnodonate, clupanodonate, docosahexaenoate, and the like. In a preferred embodiment, the active lipid comprises an oleate salt.

The active agents suitable for use with this invention are employed in well dispersed form in a pharmaceutically acceptable carrier. As used herein, "pharmaceutically acceptable carrier" encompasses any of the standard pharmaceutical carriers known to those of skill in the art. For example, one useful carrier is a commercially available emulsion, Ensure®, but active lipids, such as oleate or oleic acid are also dispersible in gravies, dressings, sauces or other comestible carriers. Dispersion can be accomplished in various ways. The first is that of a solution.

Lipids can be held in solution if the solution has the properties of bile (i.e., solution of mixed micelles with bile salt added), or the solution has the properties of a detergent (e.g., pH 9.6 carbonate buffer) or a solvent (e.g., solution of Tween). The second is an emulsion which is a 2-phase system in which one liquid is dispersed in the form of small globules throughout another liquid that is immiscible with the first liquid (Swinyard and Lowenthal, "Pharmaceutical Necessities" REMINGTON'S PHARMACEUTICAL SCIENCES, 17th ed., AR Gennaro (Ed), Philadelphia College of Pharmacy and Science, 1985 p.1296). The third is a suspension with dispersed solids (e.g., microcrystalline suspension). Additionally, any emulsifying and suspending agent that is acceptable for human consumption can be used as a vehicle for dispersion of the composition. For example, gum acacia, agar, sodium alginate, bentonite, carbomer, carboxymethylcellulose, carrageenan, powdered cellulose, cholesterol, gelatin, hydroxyethyl cellulose, hydroxypropyl cellulose, hydroxypropyl methylcellulose, methylcellulose, octoxynol 9, oleyl alcohol, polyvinyl alcohol, povidone, propylene glycol monostearate, sodium lauryl sulfate, sorbitan esters, stearyl alcohol, tragacanth, xantham gum, chondrus, glycerin, trolamine, coconut oil, propylene glycol, thyl alcohol malt, and malt extract.

Any of these formulations, whether it is a solution, emulsion or suspension containing the active agent, can be incorporated into capsules, or a microsphere or particle (coated or not) contained in a capsule.

The pharmaceutically acceptable compositions containing the active agent, in accordance with the invention, is in a form suitable for oral or enteral use, for example, as tablets, troches, lozenges, aqueous or oily suspensions, dispersible powders or granules, emulsions, hard or soft capsules, syrups, elixirs or enteral formulas. Compositions intended for oral use are prepared according to any method known to the art for the manufacture of pharmaceutical compositions. Compositions can also be coated by the techniques described in the U.S. Pat. Nos. 4,256,108; 4,160,452; and 4,265,874, to form osmotic therapeutic tablets for controlled release. Other techniques for controlled release compositions, such as those described in the U.S. Pat. No. 4,193,985; and 4,690,822; 4,572,833 can be used in the formulation of the inventive pharmaceutically acceptable compositions.

An effective amount of active lipid is any amount that is effective to slow gastrointestinal transit and control presentation of a substance to a desired region of the small intestine. For example, an effective amount of active lipid, as contemplated by the instant invention, is any amount of active lipid that can trigger any or all of the following reflexes: intestino-lower esophageal sphincter (relaxation of LES); intestino-gastric feedback (inhibition of gastric emptying); intestino-intestinal feedback (ileo-jejunal feedback/ileal brake, jejuno-jejunal feedback/jejunal brake, intestino-CNS feedback (for example, intensifying intestinal signalling of satiety); intestino-pancreatic feedback (control of exocrine enzyme output); intestino-biliary feedback (control of bile flow); intestino-mesenteric blood flow feedback (for the control of mucosal hyperemia); intestino-colonic feedback (so called gastro-colonic reflex whereby the colon contracts in response to nutrients in the proximal small intestine).

Methods of administering are well known to those of skill in the art and include most preferably oral administration and/or enteral administration. Representative methods of administering include giving, providing, feeding or force-feeding, dispensing, inserting, injecting, infusing, perfusing, prescribing, furnishing, treating with, taking, swallowing, eating or applying. Preferably the pharmaceutically acceptable composition comprising the active agent is administered in the setting of a meal, i.e., along with or substantially simultaneously with the meal, most preferably an hour or less before the meal. It is also useful to administer the active agent in the fasted state, particularly if the pharmaceutical composition containing the active agent is formulated for long acting or extended release. In some embodiments, such as the inventive method for manipulating post-prandial blood flow, the pharmaceutical composition is also usefully administered up to an hour after a meal, and most preferably within one hour before or after the meal.

In order to stretch biologic activity so that one has a convenient, daily dosage regimen, the present invention contemplates that the inventive compositions can be administered prior to ingestion of the food, nutrient and/or drug.

In a preferred embodiment, the inventive compositions (depending on the formulation) are administered up to a period of 24 hours prior to ingestion of the food, nutrient and/or drug, but most preferably between about 60 to 5 minutes before ingestion. The period of time prior to ingestion is determined on the precise formulation of the composition. For example, if the formulation incorporates a controlled release system, the duration of release and activation of the active lipid will determine the time for administration of the composition. Sustained release formulation of the composition is useful to ensure that the feedback effect is sustained.

In a preferred embodiment, the pharmaceutically acceptable composition of the invention contains an active lipid and is administered in a load-dependent manner which ensures that the dispersion of active lipid is presented to the entire length of the small intestine. Administration is in one or more doses such that the desired effect is produced. In some preferred embodiments, the load of active lipid per dose is from about 0.5 grams to about 2.0 grams, but can range up to about 25 grams per dose as needed. Generally, patients respond well to the most preferred amount of active lipid, which is in the range of about 1.6 to 3.2 grams. For patients who fail to respond to this dose range, a dose between 6 and 8 grams is typically effective.

Sequential dosing is especially useful for patients with short bowel syndrome or others with abnormally rapid intestinal transit times. In these patients, the first preprandial administration of the active lipid occurs in a condition of uncontrolled intestinal transit that can fail to permit optimal effectiveness of the active lipid. A second (or more) preprandial administration(s) timed about fifteen minutes after the first or previous administration and about fifteen minutes before the meal enhances the patient's control of intestinal lumenal contents and the effectiveness of the active lipid in accordance with the inventive methods. Normalization of nutrient absorption and bowel control throughout the day, including during the patient's extended sleeping hours, is best achieved by a dietary regimen of three major meals with about five snacks interspersed between them, including importantly, a pre-bedtime snack; administration of a dose of the inventive composition should occur before each meal or snack as described above.

Treatment with the inventive compositions in accordance with the inventive methods can be of singular occurrence or can be continued indefinitely as needed. For example, patients deprived of food for an extended period (e.g., due to a surgical intervention or prolonged starvation), upon the reintroduction of ingestible food, can benefit from administration of the inventive compositions before meals on a temporary basis to facilitate a nutrient adaptive response to normal feeding. On the other hand some patients, for example those with surgically altered intestinal tracts (e.g., ileal resection), can benefit from continued pre-prandial treatment in accordance with the inventive methods for an indefinite period. However, clinical experience with such patients for over six years has demonstrated that after prolonged treatment there is at least a potential for an adaptive sensory feedback response that can allow them to discontinue treatment for a number of days without a recurrence of postprandial diarrhea or intestinal dumping.

The use of pharmaceutically acceptable compositions of the present invention in enteral feeding contemplates adding the composition directly to the feeding formula. The composition can either be compounded as needed into the enteral formula when the rate of formula delivery is known (i.e., add just enough composition to deliver the load of active lipids). Alternatively, the composition of the invention can be compounded at the factory so that the enteral formulas are produced having different concentrations of the composition and can be used according to the rate of formula delivery (i.e., higher concentration of composition for lower rate of delivery).

If the inventive composition were to be added to an enteral formula and the formula is continuously delivered into the small intestine, the composition that is initially presented with the nutrient formula would be slowing the transit of nutrients that are delivered later. Except for the start of feeding when transit can be too rapid because the inhibitory feedback from the composition has yet to be fully activated, once equilibrium is established, it is no longer logistically an issue of delivering the composition as a premeal although the physiologic principle is still the same.

Before dietary fats can be absorbed, the motor activities of the small intestine in the postprandial period must first move the output from the stomach to the appropriate absorptive sites of the small intestine. To achieve the goal of optimizing the movement of a substance through the small intestine, the temporal and spatial patterns of intestinal motility are specifically controlled by the nutrients of the lumenal content.

Without wishing to be bound by any theory, it is presently believed that early in gastric emptying, before inhibitory feedback is activated, the load of fat entering the small intestine can be variable and dependent on the load of fat in the meal. Thus, while exposure to fat can be limited to the proximal small bowel after a small load, a larger load, by overwhelming more proximal absorptive sites, can spill further along the small bowel to expose the distal small bowel to fat. Thus, the response of the duodenum to fat limits the spread of fat so that more absorption can be completed in the proximal small intestine and less in the distal small intestine. Furthermore, since the speed of movement of lumenal fat must decrease when more fat enters the duodenum, in order to avoid steatorrhea, intestinal transit is inhibited in a load-dependent fashion by fat. This precise regulation of intestinal transit occurs whether the region of exposure to fat is confined to the proximal gut or extended to the distal gut.

In accordance with the present invention it has been observed that inhibition of intestinal transit by fat depends on the load of fat entering the small intestine. More specifically, that intestinal transit is inhibited by fat in a load-dependent fashion whether the nutrient is confined to the proximal segment of the small bowel or allowed access to the whole gut.

As the term is commonly used in the art, the "proximal" segment of the small bowel, or "proximal gut", comprises approximately the first half of the small intestine from the pylorus to the mid-gut. The distal segment, or "distal gut" includes approximately the second half, from the mid-gut to the ileal-cecal valve.

Accordingly, the present invention provides a method of slowing gastrointestinal transit in a subject having a gastrointestinal disorder, said method comprising administering to said subject a composition comprising an active lipid in an amount sufficient to prolong the residence time of a substance in the small intestine.

Inventive methods and compositions are useful in the management of nutritional and absorption in subjects having a variety of gastrointestinal symptoms such as, abnormally rapid or slow upper gastrointestinal transit, dumping syndrome, diarrhea, weight loss, distention, steatorrhea, and asthenia to symptoms of specific nutrient deficiencies (i.e., malnutrition), cachexia, anorexia, bulimia, and obesity.

Examples of gastrointestinal disorders for which the inventive methods and compositions are therapeutic include postgastrectomy syndrome, dumping syndrome, AIDS-associated chronic diarrhea, diabetes-associated diarrhea, postvagotomy diarrhea, bariatric surgery-associated diarrhea (including obesity surgeries: gastric bypass, gastroplasties and intestinal bypass), short bowel syndrome (including resection of the small intestine after trauma, radiation induced complications, Crohn's disease, infarction of the intestine from vascular occlusion), tube-feeding related diarrhea, chronic secretory diarrhea, carcinoid syndrome-associated diarrhea, gastrointestinal peptide tumors, endocrine tumors, chronic diarrhea associated with thyroid disorders, chronic diarrhea in bacterial overgrowth, chronic diarrhea in gastrinoma, choleraic diarrhea, chronic diarrhea in giardiasis, antibiotic-associated chronic diarrhea, diarrhea-predominant irritable bowel syndrome, chronic diarrhea associated with maldigestion and malabsorption, chronic diarrhea in idiopathic primary gastrointestinal motility disorders, chronic diarrhea associated with collagenous colitis, surgery-associated acute diarrhea, antibiotic-associated acute diarrhea, infection-associated acute infectious diarrhea, and the like.

The instant invention further provides a method and composition for treating diarrhea in a subject, said method comprising administering to said subject a composition comprising an active lipid in an amount sufficient to prolong the residence time of the lumenal contents of the small intestine. The inventive composition can be delivered as a single unit, multiple unit (for more prolonged effect via enterically coated or sustained release forms) or in a liquid form.

Since cholesterol and triglycerides are so insoluble in plasma, after mucosal absorption of lipids, the transport of these lipids from the intestine to the liver occurs through lipoproteins called chylomicrons.

While fat absorption from the lumen is rate-limiting for the proximal half of the small intestine, chylomicron synthesis or release is rate-limiting for the distal one half of the small intestine. As a result, chylomicrons formed by the distal small intestine are larger than those from the proximal small intestine (Wu, 1975). In the capillary bed of the peripheral circulatory system, the enzyme lipoprotein lipase hydrolyzes and removes most of the triglycerides from the chylomicron. The lipoprotein that remains, now rich in cholesterol esters and potentially atherogenic, is called a chylomicron remnant. This postprandial lipoprotein is then removed from the circulation by the liver (Zilversmit, *Circulation* 60(3):473 [1979]).

Elevated levels of atherogenic serum lipids have been directly correlated with atherosclerosis (Keinke et al., *Q. J. Exp. Physiol.* 69:781–795 [1984]).

The present invention provides a novel method to minimize atherogenic postprandial lipemia by optimizing proximal fat absorption. In other words, the present invention provides a novel method by which atherogenic serum lipids can be controlled preabsorptively by the fed motility response of the small intestine to lumenal fat.

Preabsorptive control depends on the triggering of a specific pattern of proximal intestinal motility which slows transit to minimize the spread of fat into the distal gut. After a small meal of cholesterol-containing, fatty foods, the small intestine limits the site of fat absorption to the proximal small intestine by generating nonpropagated motility to slow intestinal transit. Since chylomicrons produced by the proximal small intestine are small in size, the size distribution of postprandial lipoproteins is shifted to minimize postprandial lipemia. However, during gorging of a high cholesterol, high fat meal, the ability of the small intestine to optimize proximal fat absorption is reduced by the time-dependent fading of the effect of fat on nonpropagated motility. As a result, after the first 1–2 hours, faster intestinal transit works to displace lumenal fat into the distal small intestine where large, cholesterol-enriched, atherogenic chylomicrons are formed and released into the circulation.

In addition to the dietary effects on intestinal transit, studies suggest that nicotine inhibits intestinal motility. (McGill [1979]; Maida [1990]) (Booyse [1981]) (Carlson [1970]). In the postprandial situation, this nicotine-related inhibitory effect alters the potentially protective, braking or nonpropagated pattern of motility. As a result, nicotine can facilitate the spreading of ingested lipids into the distal small intestine and impair the preabsorptive control of lipids. The methods of the present invention provide means to minimize the nicotine-induced inhibition of this postprandial response and to maximize proximal fat absorption.

Oral pharmaceutical preparations account for more than 80% of all drugs prescribed. It is essential, therefore, to control the multiple factors that influence their intestinal absorption as a determinant of ultimate therapeutic effectiveness.

Disintegration and dissolution are factors determining drug absorption that takes place only after a drug is in solution. Drugs ingested in solid form must first dissolve in the gastrointestinal fluid before they can be absorbed, and tablets must disintegrate before they can dissolve. The dissolution of a drug in the gastrointestinal tract is often the rate-limiting step governing its bioavailability. In any given drug, there can be a 2- to 5-fold difference in the rate or extent of gastrointestinal absorption, depending on the dosage or its formulation.

The rate of gastric emptying bears directly on the absorption of ingested drugs and on their bioavailability. Some drugs are metabolized or degraded in the stomach, and delayed gastric emptying reduces the amount of active drug available for absorption.

The pharmaceutical industry has developed all sorts of slow and/or sustained-release technology. These efforts have been directed to delaying gastric emptying. Sustained-release formulations employ several methods. The most common is a tablet containing an insoluble core; a drug applied to the outside layer is released soon after the medication is ingested, but drug trapped inside the core is released more slowly. Capsules containing multiparticulate units of drug with coatings that dissolve at different rates are designed to give a sustained-release effect. However, the basic problem with sustained-release medications is the considerable variability in their absorption due to the inability to monitor the individual's ingestion of the medication and thus, inability to control transit. Accordingly, slow release of drug in the absence of slow transit in the gut is meaningless.

The instant invention solves the bioavailability problem in this instance. The methods and compositions of this invention enable one to manipulate the balance of dissolution and gastrointestinal transit by increasing gastrointestinal residence time.

To facilitate drug absorption in the proximal small intestine, the present invention provides a method for prolonging the gastrointestinal residence time which will allow drugs in any dosage form to more completely dissolve and be absorbed. Since the inventive compositions slow gastrointestinal transit (delays both gastric emptying and small intestinal transit) a more rapid dissolving dosage form is preferred.

Accordingly, the present invention provides pharmaceutical oral articles and enteral formulas that slow gastrointestinal transit and prolong residence time of a substance. The composition of the invention enhance dissolution, absorption, and hence bioavailability of drugs ingested concurrently therewith or subsequent thereto.

Pharmaceutical compositions of the present invention can be used in the form of a solid, a solution, an emulsion, a dispersion, a micelle, a liposome, and the like, wherein the resulting composition contains one or more of the compounds of the present invention, as an active ingredient, in admixture with an organic or inorganic carrier or excipient suitable for enteral or parenteral applications. The active ingredient can be compounded, for example, with the usual non-toxic, pharmaceutically acceptable carriers for tablets, pellets, capsules, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes can be used.

The active lipid is included in the pharmaceutical composition in an amount sufficient to produce the desired effect upon the process or condition of diseases.

Pharmaceutically acceptable compositions containing the active agent can be in a form suitable for oral use, for example, as tablets, troches, lozenges, aqueous or oily suspensions, dispersible powders or granules, emulsions, hard or soft capsules, syrups, elixirs or enteral formulas. Compositions intended for oral use can be prepared according to any method known to the art for the manufacture of pharmaceutical compositions and such compositions can contain one or more other agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing the active ingredient in admixture with non-toxic pharmaceutically acceptable excipients can also be manufactured by known methods. The excipients used can be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets can be uncoated or they can be coated by known techniques to delay disintegration and absorption in the gastrointestinal tract and thereby provide a sustained action over a longer period. For example, a time delay material such as glyceryl monostearate or glyceryl distearate can be employed. They can also be coated by the techniques described in the U.S. Pat. Nos. 4,256,108; 4,160,452; and 4,265,874, to form osmotic therapeutic tablets for controlled release. Other techniques for controlled release compositions, such as those described in the U.S. Pat. Nos. 4,193,985; and 4,690,822; 4,572,833 can be used in the formulation of the inventive pharmaceutically acceptable compositions.

In some cases, formulations for oral use can be in the form of hard gelatin capsules wherein the active ingredient is mixed with an inert solid diluent, for example, calcium carbonate, calcium phosphate or kaolin. They can also be in the form of soft gelatin capsules wherein the active ingredient is mixed with water or an oil medium, for example, peanut oil, liquid paraffin, or olive oil.

The methods and compositions of the invention are most needed for drugs that have slow dissolution characteristics. Since the drug is released slowly in such formulations that are now enterically coated or packaged in a sustained release form, there is great potential for the drug to be passed into the colon still incompletely absorbed. In embodiment of the method of manipulating the rate of upper gastrointestinal transit, the role of the inventive pharmaceutically acceptable compositions is to increase the gastrointestinal residence time to allow the poorly dissoluting drugs to be fully absorbed.

In one embodiment of the present invention, the pharmaceutically acceptable composition is an enterically coated or a sustained release form that permits intestinal transit to be slowed for a prolonged period of time. The drug can also be packaged in an enterically coated or sustained release form so that it can also be released slowly. This combination would probably have the longest biologic activity and be favored if a high initial drug plasma peak is not desirable.

In an alternative embodiment, inventive pharmaceutically acceptable compositions are formulated for controlled release (enterically coated or sustained release form) whereas a rapid release formulation is contemplated for the drug (tablet or capsule with rapid dissolution characteristics or composition in a liquid form). This simpler strategy is used if the inventive pharmaceutically acceptable composition is able to "hold" the drug in the proximal small intestine for a period long enough for complete absorption of the drug to take place and a high initial peak of the drug is desirable.

Another embodiment is a rapid release formulation of the inventive pharmaceutically acceptable composition. This form is administered following slow release of the drug which is enterically coated or a sustained release form.

Also contemplated by the instant invention is the combination of a rapid release form of the inventive pharmaceutically acceptable composition and a rapid release of the drug.

Accordingly, the methods and compositions of the instant invention can be combined with the existing pharmaceutical release technology to provide control over not only the gastrointestinal transit and residence time of a drug, but also over the time of release of the active agent. More specifically, the combination of invention methods and compositions with existing release technology provides control over the multiple factors that influence intestinal absorption of a drug. The ability to control such factors enables optimization of the bioavailability and ultimate therapeutic effectiveness of any drug.

The present invention provides a means to enhance region-to region (e.g., gut-to-CNS or gut-to gut) communications by way of replicating 5-HT as a signal (or releasing 5-HT at a distance as a surrogate signal). Thus, the present invention provides a way to increase 5-HT in locations in the central nervous by transmitting a neural signal from the gut. Gut-to-brain serotonergic signal replication can be used for preventing or treating anti-anxiety/panic disorders, depression, phobias, bulimia and other eating disorders, obsessive-compulsive disorders, mood disorders, bipolar disorders, aggression/anger, dysthmia, alcohol and drug dependence, nicotine dependence, psychosis, improving cognition/memory, improving brain blood flow, antinociception/analgesia, and/or suppression of feeding. The inventive technology can replace or supplement the use of serotonin reuptake inhibitors.

In particular, the invention relates to a method of transmitting to and replicating at a second location in the central nervous system a serotonergic neural signal originating at a first location in the proximal or distal gut of the mammalian subject. The method involves administering by an oral or enteral delivery route to the mammalian subject a pharmaceutically acceptable composition containing an active agent, which is an active lipid; serotonin, a serotonin agonist, or a serotonin re-uptake inhibitor; peptide YY or a peptide YY functional analog; CGRP, or a CGRP functional analog. The composition is formulated to deliver the active agent to the first location in the proximal or distal gut. Substantially simultaneously with the active agent, an adrenoceptor antagonist is also delivered orally or enterally to the mammal, either in the same composition or by administering orally or enterally a second separate composition containing the adrenoceptor antagonist. Thus, a serotonergic neural signal is produced in the upper gastrointestinal tract; the signal is transmitted via the intrinsic cholinergic afferent neural pathway to the prevertebral ganglion and thence to the central nervous system. The neural signal is ultimately replicated at the second location in the central nervous system, for example in the hypothalamus, as a serotonergic neural signal.

Similarly, the inventive technology provides a method of transmitting to and replicating at a second location in the upper gastrointestinal tract a serotonergic neural signal originating at a first location in the proximal or distal gut of a mammal. For example, the first location can be in the proximal gut and the second location can be elsewhere in the proximal gut or in the distal gut. Or conversely, the first location can be in the distal gut and the second location can be elsewhere in the distal gut or in the proximal gut.

A preferred embodiment includes administering by an oral or enteral delivery route to the mammal a pharmaceutically acceptable composition containing an active agent, which is an active lipid; serotonin, a serotonin agonist, or a serotonin re-uptake inhibitor; peptide YY or a peptide YY functional analog; CGRP, or a CGRP functional analog. The composition is formulated to deliver the active agent to the first location in the proximal or distal gut, whereby a serotonergic neural signal is produced, and then transmitted via an intrinsic cholinergic afferent neural pathway and the prevertebral ganglion and is replicated at the second location as a serotonergic neural signal.

Some embodiments of the method of manipulating the rate of upper gastrointestinal transit of a substance involve slowing the rate of upper gastrointestinal transit, for example after a meal. This aspect of the invention is useful in increasing the absorption or bioavailablity of drugs or for increasing nutrient absorption. In response to luminal fat in the proximal or distal gut, a serotonin (5-HT)-mediated anti-peristaltic slowing response is normally present. Therefore, some embodiments of the method involve increasing 5-HT in the gut wall by administering to the mammal and delivering to the proximal and/or distal gut, an active lipid, or serotonin, a serotonin agonist, or a serotonin re-uptake inhibitor.

Alternatively, the active agent is PYY, or a PYY functional analog. PYY or the PYY analog activates the PYY-sensitive primary sensory neurons in response to fat or 5-HT. Since the predominant neurotransmitter of the PYY-sensitive primary sensory neurons is calcitonin gene-related peptide (CGRP), in another embodiment, CGRP or a CGRP functional analog is the active agent.

In other embodiments the point of action is an adrenergic efferent neural pathway, which conducts neural signals from one or more of the celiac, superior mesenteric, and inferior mesenteric prevertebral ganglia, back to the enteric nervous system. The active agent is an adrenergic receptor (i.e., adrenoceptor) agonist to activate neural signal transmission to the efferent limb of the anti-peristaltic reflex response to luminal fat.

Since adrenergic efferent neural pathway(s) from the prevertebral ganglia to the enteric nervous system stimulate serotonergic interneurons, which in turn stimulate enteric opioid interneurons, in other embodiments of the method, the active agent is 5-HT, 5-HT receptor agonist, or a 5-HT re-uptake inhibitor to activate or enhance neural signal transmission at the level of the serotoneregic interneurons.

Alternatively, the active agent is an opioid receptor agonist to activate or enhance neural signal transmission via the opioid interneurons.

Some embodiments of the method of manipulating the rate of upper gastrointestinal transit of a substance involve accelerating the rate of gastrointestinal transit, for example after a meal. This aspect of the invention is useful in countering the transit-slowing effects of opioid medications or for decreasing nutrient absorption in the treatment of obesity. In response to luminal fat in the proximal or distal gut, a serotonin-mediated anti-peristaltic slowing response is normally exhibited. But this anti-peristaltic response to the release of 5-HT in the proximal or distal gut wall is switched to a peristaltic response to 5-HT by administering to the mammal and delivering a PYY receptor antagonist to the proximal and/or distal gut. The PYY antagonist blocks or reduces the activation of primary sensory neurons in response to fat or 5-HT. In another embodiment, a calcitonin gene-related peptide receptor antagonist is contained in the pharmaceutical composition, to block the action of CGRP, the neurotransmitter of the primary sensory neurons, which are activated by PYY.

In other embodiments the point of action is an adrenergic efferent neural pathway, which conducts neural signals from one or more of the celiac, superior mesenteric, and inferior mesenteric prevertebral ganglia, back to the enteric nervous system. The active agent is an adrenergic receptor (i.e., adrenoceptor) antagonist to block neural signal transmission to the efferent limb of the anti-peristaltic reflex response to luminal fat.

Since adrenergic efferent neural pathway(s) from the prevertebral ganglia to the enteric nervous system stimulate serotonergic interneurons, which in turn stimulate enteric opioid interneurons, in other embodiments of the method, the active agent is a 5-HT receptor antagonist to block or reduce neural signal transmission at the level of the serotoneregic interneurons.

Alternatively, the active agent is an opioid receptor antagonist to block neural signal transmission via the opioid interneurons.

Some embodiments of the method of manipulating postprandial visceral blood flow involve increasing visceral blood flow, which includes mesenteric, enteric, and gastric blood flow. This aspect of the invention is useful in increasing the absorption or bioavailablity of drugs or for increasing nutrient absorption. Some embodiments involve increasing 5-HT in the gut wall by administering and delivering to the proximal and/or distal gut, an active lipid, or serotonin, a serotonin agonist, or a serotonin re-uptake inhibitor.

Alternatively, the active agent is PYY, or a PYY functional analog. PYY or the PYY analog activates the PYY-sensitive primary sensory neurons in response to fat or 5-HT. Since the predominant neurotransmitter of the PYY-sensitive primary sensory neurons is calcitonin gene-related peptide (CGRP), in another embodiment, CGRP or a CGRP functional analog is the active agent.

In other embodiments the point of action is an adrenergic efferent neural pathway, which conducts neural signals from one or more of the celiac, superior mesenteric, and inferior mesenteric prevertebral ganglia, back to the enteric nervous system. The active agent is an adrenergic receptor (i.e., adrenoceptor) agonist to activate neural signal transmission to the efferent limb of the anti-peristaltic reflex response to luminal fat.

Since adrenergic efferent neural pathway(s) from the prevertebral ganglia to the enteric nervous system stimulate serotonergic interneurons, which in turn stimulate enteric opioid interneurons, in other embodiments of the method, the active agent is 5-HT, a 5-HT receptor agonist, or a 5-HT re-uptake inhibitor to activate or enhance neural signal transmission at the level of the serotoneregic interneurons.

Alternatively, the active agent is an opioid receptor agonist to activate or enhance neural signal transmission via the opioid interneurons.

Some embodiments of the method of manipulating postprandial visceral blood flow involve decreasing post-prandial visceral blood flow by administering a PYY receptor antagonist to the proximal and/or distal gut. The PYY antagonist blocks or reduces the activation of primary sensory neurons in response to fat or 5-HT, thereby decreasing post-prandial visceral blood flow compared to blood flow without the active agent.

In another embodiment, a calcitonin gene-related peptide receptor antagonist is the active agent, to block the action of CGRP, the predominant neurotransmitter of the primary sensory neurons, which are activated by PYY.

In other embodiments the point of action is an adrenergic efferent neural pathway, which conducts neural signals from one or more of the celiac, superior mesenteric, and inferior mesenteric prevertebral ganglia, back to the enteric nervous system. The active agent is an adrenergic receptor (i.e., adrenoceptor) antagonist.

Since adrenergic efferent neural pathway(s) from the prevertebral ganglia to the enteric nervous system stimulate serotonergic interneurons, which in turn stimulate enteric opioid interneurons, in other embodiments of the method, the active agent contained in the active agent is a 5-HT receptor antagonist to block or reduce neural signal transmission at the level of the serotoneregic interneurons.

Alternatively, the active agent is an opioid receptor antagonist to block neural signal transmission via the opioid interneurons.

Some embodiments of the method of manipulating satiety involve inducing satiety. Fat in the intestinal lumen can induce satiety. In response to luminal fat in the proximal or distal gut satiety is induced. This fat signal is serotonin (5-HT)-mediated. Therefore, some embodiments of the method involve increasing 5-HT in the gut wall by administering to the mammal and delivering to the proximal and/or distal gut, an active lipid, or serotonin, a serotonin agonist, or a serotonin re-uptake inhibitor.

Alternatively, the active agent is PYY, or a PYY functional analog. PYY or the PYY analog activates the PYY-sensitive primary sensory neurons in response to fat or 5-HT. Since the predominant neurotransmitter of the PYY-sensitive primary sensory neurons is calcitonin gene-related peptide (CGRP), in another embodiment, CGRP or a CGRP functional analog is the active agent.

In other embodiments the point of action is an adrenergic efferent neural pathway, which conducts neural signals from one or more of the celiac, superior mesenteric, and inferior mesenteric prevertebral ganglia, back to the enteric nervous system. The active agent is an adrenergic receptor (i.e., adrenoceptor) agonist to activate neural signal transmission to the efferent limb of the response to luminal fat.

Since adrenergic efferent neural pathway(s) from the prevertebral ganglia to the enteric nervous system stimulate serotonergic interneurons, which in turn stimulate enteric opioid interneurons, in other embodiments of the method, the active agent is 5-HT, a 5-HT receptor agonist, or a 5-HT re-uptake inhibitor to activate or enhance neural signal transmission at the level of the serotonergic interneurons.

Alternatively, the active agent is an opioid receptor agonist to activate or enhance neural signal transmission via the opioid interneurons.

In a most preferred embodiment of the method for inducing satiety a combination of active agents is employed. The combination includes active lipid, 5-HT, a 5-HT agonist, PYY, and/or a PYY functional analog together with an adrenoceptor antagonist. The active lipid, 5-HT, 5-HT agonist, PYY, and/or PYY functional analog initiate the satiety signal from the enteric nervous system, while the adrenoceptor antagonist blocks the neural signal transmission of signal from prevertebral ganglion back to the gut enteric nervous system, so that the signal is gated in the direction of prevertebral ganglion to the central nervous system, particularly projecting from the prevertebral ganglion to the hypothalamus of the mammalian subject.

Some embodiments of the method of manipulating satiety involve suppressing satiety by administering a PYY receptor antagonist to the proximal and/or distal gut. The PYY antagonist blocks or reduces the activation of primary sensory neurons in response to fat or 5-HT. In another embodiment, a calcitonin gene-related peptide receptor antagonist is the active agent, to block the action of CGRP, the neurotransmitter of the primary sensory neurons, which are activated by PYY.

In other embodiments the point of action is an adrenergic efferent neural pathway, which conducts neural signals from one or more of the celiac, superior mesenteric, and inferior mesenteric prevertebral ganglia, back to the enteric nervous system. The active agent is an adrenergic receptor (i.e., adrenoceptor) antagonist.

Since adrenergic efferent neural pathway(s) from the prevertebral ganglia to the enteric nervous system stimulate serotonergic interneurons, which in turn stimulate enteric opioid interneurons, in other embodiments of the method, the active agent is a 5-HT receptor antagonist to block or reduce neural signal transmission at the level of the serotoneregic interneurons.

Alternatively, the active agent is an opioid receptor antagonist to block neural signal transmission via the opioid interneurons.

The invention includes a method for treating visceral pain or visceral hyperalgesia, which involves blocking or substantially reducing activation, i.e., neural signal transmission, of any of a cholinergic intestino-fugal pathway, one or more prevertebral ganglionic pathways, a gangalion to central nervous system pathway, the adrenergic efferent neural pathway, the serotonergic interneuron and/or the opioid interneuron such that activation thereof is substantially reduced by the action of the active agent. The result is that the sensation of esophageal, gastric, biliary, intestinal, colonic or rectal pain experienced by the human subject is reduced. Most preferably the point of neural blockade, for example one or more of the prevertebral ganglia, prevents transmission of neural signals from the enteric nervous system to the central nervous system.

In a most preferred embodiment of the method, the pharmaceutically acceptable composition includes an opioid agonist specific for the opioid receptors of the prevertebral ganglionic cells, preferably an agonist of 5-HT3,5-HT1P, 5-HT2, and/or 5-HT4, in combination with an opioid receptor antagonist to enhance activation of the enteric nervous system-to-prevertebral ganglion opioid neural pathway. While the opioid agonist will be available to the prevertebral ganglion after absorption into the systemic circulation from the lumen, the opioid receptor antagonist, preferably naloxone, acts from the intestinal lumen in the proximal and/or distal gut on the opioid receptors of the enteric nervous system to inhibit the effect of the opioid agonist in slowing the rate of gut transit. Since the opioid antagonist is nearly completely eliminated by the liver before reaching systemic circulation, the opioid agonist acts systemically on the prevertebral ganglion to block the transmission of neural signals to the central nervous system, without incurring an opioid-induced slowing effect on gut transit.

In other embodiments of the method, the point of blockade is the PYY-sensitive primary sensory neurons of the intestinal wall. In one embodiment, the administered pharmaceutical composition contains a PYY antagonist to prevent or reduce activation of primary sensory neurons in response to fat or 5-HT. In another embodiment, a calcitonin gene-related peptide receptor antagonist is contained in the pharmaceutically acceptable composition, to block the action of CGRP, the neurotransmitter of the primary sensory neurons, which are activated by PYY.

Detecting neural pathway activation or blockage is not necessary to the practice of the inventive methods. However, one skilled in the art is aware of methods for measuring outcomes, such as the rate of intestinal transit, for example, by using the lactulose breath hydrogen test in humans to detect an effect on the rate of upper gastrointestinal transit after treatment in accordance with the method of manipulating upper gastrointestinal transit. For example, the effect on fat-induced slowing of transit can be measured when various agonists and/or antagonists are used, e.g., cholinergic antagonists, such as atropine or hexamethonium, to test for cholinergic pathway activation, propranolol to test for adrenergic pathway activation, ondansetron to test for serotonergic pathway activation, naloxone or another opioid receptor antagonist for the opioid pathways. In this way, after a standard fat meal, the expected rate of transit would be accelerated with these agents to confirm that these pathways were activated. Biochemical or immunochemical assays can also be performed to quantitate various neurotransmitters, such as 5-HT or PYY, in biological samples from the mammalian subject, e.g., collected intestinal juice. By way of example, serotonin in the sample can be assayed after the intestine is exposed to fat. Ways of collecting intestinal juice for such measurement are known, including by direct aspiration via endoscope or fluoroscopically placed nasointestinal tube or using capsules on a string that is equipped to allow serotonin to enter the capsule in the manner of a microdialysate.

Behavioral or subjective indicators of outcome related to outcomes of satiety manipulation or the experience of visceral pain are also useful.

The following examples are intended to illustrate, but not limit, the present invention.

EXAMPLE I

Oleate and Oleic Acid Slow Upper Gut Transit and Reduce Diarrhea in Patients with Rapid Upper Gut Transit and Diarrhea Rapid transit through the upper gut can result in diarrhea, maldigestion and absorption, and weight loss; and pharmacologic treatment with opiates or anticholinergics often is required. It was tested whether fatty acids could be used to slow upper gut transit and reduce diarrhea in patients with rapid transit and diarrhea.

In a preliminary study, five patients with persistent diarrhea for 3 to 22 months, (one each due to vagal denervation, ileal resection for Crohn's disease, and vagotomy and antrectomy, and two due to idiopathic causes) were studied. Each patient demonstrated rapid upper gut transit on routine lactulose breath hydrogen testing (or variations thereof measuring labelled carbon dioxide)(Cammack et al. *Gut* 23:957–961 [1982]). This test relies on the metabolism of certain carbohydrate materials (e.g. lactulose) by the microbial flora within the caecum. By generating gas which can be detected in the expired air, it is possible to make some estimation about the initial arrival of the administered material within the colon.

Each patient received orally in random order, 0, 1.6 or 3.2 g of sodium oleate in 25 mL Ensure (Ross), followed by 100 mL water. Thirty minutes after each dose of oleate, patients received 10 g lactulose orally, followed by 25 mL water. Breath samples were collected in commercially available breath testing bags (Quintron, Menomonee Falls, Wis.) every 10–15 minutes, and the hydrogen content of the samples was measured using a breath analyzer (Microlyzer Model 12, Quintron Instruments, Menomonee Falls, Wis.), calibrated against gas samples of known hydrogen concentration. With a syringe, a 40-mL sample of the expired breath was withdrawn from the collection bag and analyzed immediately for hydrogen concentration (ppm). The hydrogen concentration value from each sample was plotted against time. Upper gut transit time was defined as the time in minutes from ingestion of lactulose ($t_0$) until a rise of $H_2$ of >10 ppm. Data were further analyzed using 1-way repeated measures analysis of variance (ANOVA).

| Results (mean ± SE): | | | |
|---|---|---|---|
| | Oleate (g) | | |
| | 0 | 1.6 | 3.2 |
| Transit time (min) | 46 ± 8.6 | 116 ± 11.1 | 140 ± 11.5 |

Upper gut transit was significantly prolonged by oleate in a dose-dependent fashion (p<0.005, significant trend). During prolonged ingestion of oleate 15–30 minutes prior to meals, all patients reported reduced diarrhea. The patient with Crohn's disease reported complete resolution of chronic abdominal pain as well as post prandial bloating and nausea, and gained 22 lbs. In addition, the patient with vagotomy and antrectomy reported resolution of postprandial dumping syndrome (flushing, nausea, light-headedness).

The effect of an active lipid on transit time was determined in 8 normal human subjects (1 male and 7 females with a mean age of 35±2.6 years [SE]) and 45 patients (20 males and 25 females with a mean age of 49.1±2.5 [SE], age range from 18 to 90 years) with chronic diarrhea (i.e., continuous diarrhea for more than two months) associated with a wide variety of diagnoses and conditions (e.g., Crohn's disease; irritable bowel syndrome; short bowel syndrome; Indiana pouch; AIDS; ulcerative colitis; vagotomy; antrectomy; ileostomy; partial and complete colectomy; colon cancer; diabetes mellitus type 1; pancreatic insufficiency; radiation enteropathy; esophagectomy/gastric pull-up; total and subtotal gastrectomy; gastorjejunostomy), made by referring gastroenterologists. The method was the same as described above, except oleic acid (Penta Manufacturing, Livingston, N.J.) replaced sodium oleate in 50 mL of Ensure emulsion. All subjects refrained from taking antibiotics for at least two weeks before each testing date and during stool measurement periods. Patients were also instructed to refrain from anti-diarrheal drugs, laxatives, somatostatin analogues or anticholinergics for at least 48 hours before each test. In both the normal and patient groups, there was a significant slowing of upper gut transit time in response to oleic acid, as summarized below (p<0.001):

| | Transit time (min) (mean ± SE) | | |
|---|---|---|---|
| | Oleic Acid (g) | | |
| | 0 | 1.6 | 3.2 |
| Normal | 105.2 ± 12.1 | 116 ± 11.1 | 140 ± 11.5 |
| Patients | 29.3 ± 2.8 | 57.2 ± 4.5 | 83.3 ± 5.2 |

Continuing oleic acid treatment at home was offered to "responders" (i.e., patients who experienced a greater than 100% increase in baseline transit time with 3.2 g oleic acid). Of the 36 responders out of the original 45 patients, 18 provided records of stool volume and frequency on- and off-treatment for comparison. The inconvenient and unappealing nature of stool collection and measurement were the primary reasons reported by responders who chose not to participate in stool collection. After completing a set of three preliminary breath hydrogen tests, each participating responder was asked to refrain from taking oleic acid for two days in order to measure off-treatment stool output for a 24-hour period. Patients were issued a stool pattern record form and a stool collection container with graduated volume markings to record the frequency and volume of bowel movements. After two days without oleic acid, each patient took 3.2 g of oleic acid mixed with 25 mL of Ensure emulsion three times a day, 30 minutes before breakfast, lunch and dinner. After taking oleic acid for two days, patients recorded stool output for another 24-hour period. With this oleic acid emulsion treatment, stool frequency decreased from 6.9±0.8 to 5.4±0.9 bowel movements per 24-hour period (p<0.05), and stool volume decreased from 1829.0±368.6 to 1322.5±256.9 per 24-hour period (p<0.05).

A slight and transient burning sensation in the mouth or throat was the only adverse effect reported by any patient taking the oleic acid treatment.

These experiments demonstrate that active lipids, such as oleate and oleic acid, are effective in slowing upper gut transit in a dose-dependent manner and reduce diarrhea among patients with rapid transit and diarrhea. This novel treatment is effective in other chronic diarrheal conditions associated with rapid transit.

EXAMPLE II

Fat in Distal Gut Inhibits Intestinal Transit More Potently Than Fat in Proximal Gut In 4 dogs equipped with duodenal (10 cm from pylorus) and mid-gut (160 cm from pylorus) fistulas, intestinal transit was compared across an isolated 150 cm test segment (between fistulas) while 0, 15, 30 or 60 mM oleate was delivered into either the proximal or distal segment of the gut as a solution of mixed micelles in pH 7.0 phosphate buffer at 2 mL/min for 90 minutes. The segment of gut not receiving oleate was perfused with phosphate buffer, pH 7.0, at 2 mL/min. 60 minutes after the start of the perfusion, ~20 µCi of $^{99m}$Tc-DTPA (diethylenetriaminepentaacetic acid) was delivered as a bolus into the test segment. Intestinal transit was then measured by counting the radioactivity of 1 ml samples collected every 5 minutes from the diverted output of the mid-gut fistula.

Intestinal transit was calculated by determining the area under the curve (AUC) of the cumulative percent recovery of the radioactive marker. The square root values of the AUC (Sqrt AUC), where 0=no recovery by 30 minutes and 47.4=theoretical, instantaneous complete recovery by time 0, were compared across region of fat exposure and oleate dose using 2-way repeated measures ANOVA.

| Region of fat exposure | Oleate dose (mM) (mean ± SE) | | |
|---|---|---|---|
| | 15 | 30 | 60 |
| Proximal 1/2 of gut | 41.6 ± 1.4 | 40.6 ± 10.2 | 34.4 ± 3.0 |
| Distal 1/2 of gut | 25.6 ± 1.4 | 18.9 ± 1.5 | 7.0 ± 3.8 |

Control: buffer into both proximal and distal 1/2 of gut = 41.4 ± 4.6.

These experiments demonstrate that intestinal transit is slower when fat is exposed in the distal ½ of gut (region effect p<0.01). These experiments also demonstrate that oleate is effective to inhibit intestinal transit in a dose-dependent fashion (dose effect, p<0.05); and that dose dependent inhibition of intestinal transit by oleate depends on the region of exposure (interaction between region and dose, p<0.01).

EXAMPLE III

Case Studies Showing Successful Treatment of Diarrhea With Oleic Acid

Postgastrectomy Dumping Syndrome. The patient was a 57 year old female with a history of subtotal gastrectomy and gastrojejunostomy for peptic ulcer and gastric cancer. Symptoms on presentation of nausea, cramping pain, lightheadedness, bloating and explosive diarrhea occurring after every meal were consistent with severe dumping syndrome. These symptoms persisted despite aggressive medical therapy including the use of tincture of opium and anticholinergics. Her upper gut transit times were (min) 16 (0 g oleic acid), 99 (1.6 g oleic acid) and 108 (3.2 g oleic acid).

After one pre-meal treatment with oleic acid (3.2 g mixed with 25 mL of Ensure), this patient reported immediate benefit. With continued treatment with oleic acid (3.2 g mixed with 25 mL of Ensure, gravy or other comestible emulsion three times a day, 30 minutes before breakfast, lunch and dinner), she had only rare episodes of dumping symptoms (only about once per month). Her weight increased from 118 to 130 lbs, and bowel movements decreased from 4 to 5 liquid to 2 to 3 formed bowel movements per day.

Diarrhea-Predominant Irritable Bowel Syndrome. The patient was a 39-year old male with a history of adolescent-onset, persistent diarrhea. After a routine gastrointestinal work-up failed to provide an explanation for his symptoms, he was given the diagnosis of diarrhea-predominant irritable bowel syndrome. He presented with complaints of excessive gas, postprandial bloating, diarrhea and urgency, and 3 to 7 liquid bowel movements per day. His upper gut transit times were (min) 30 (0 g oleic acid), 117 (1.6 g oleic acid) and 101 (3.2 g oleic acid). With continuing oleic acid treatment as described above, he reported his bowel frequency reduced to a single, solid bowel movement per day. He also reported complete relief from the symptoms of gaseousness, bloating and rectal urgency.

History of Ileal Resection. The patient was a 64 year old female who had chronic diarrhea since 1990, when she underwent an intestinal resective surgery to create an Indiana Pouch from her ileum to drain her right kidney. After the surgery, the patient had approximately 4 to 6 watery bowel movements per day with a 24-hour stool volume of 950 mL. At the time of presentation, she had reported a weight loss of 20 lbs over the previous 6-month period despite greater than normal appetite and food intake. Her upper gut transit times were (min) 60 (0 g oleic acid), 68 (1.6 g oleic acid) and 148 (3.2 g oleic acid). With continuing oleic acid treatment as described above, her 24-hour stool volume decreased to 200 mL, and her stool frequency was reduced to a single solid bowel movement daily.

Short Bowel Syndrome. The patient was a 38-year old male with a thirty-year history of Crohn's disease. Five intestinal resections had resulted in a remainder of about 100 cm of small intestine and descending colon. He presented at 93 lbs; with severe difficulties with oral intake, and was readied with placement of a central line for life-long total parenteral nutrition (TPN). He was experiencing more than 20 bowel movements per day, with pain, bloating and nausea at each meal. Baseline upper gut transit time was 14 min. His transit time was prolonged to 47 and 158 min with 1.6 and 3.2 grams of oleic acid, respectively. After the patient began taking oleic acid three times a day, his stool volume decreased during the first 24-hour period from 3400 mL to 1400 mL. Over the course of 2 months of oleic acid treatment, he gained 30 lbs without TPN, and he was able to enjoy an unrestricted diet without symptoms.

A 42-year-old female patient with a history of Crohn's disease and intestinal resective surgeries developed severe diarrhea after her latest intestinal resection and iliostomy. Before treatment, her stool volume was about 1025 mL per day. With oleic acid (6.6 grams in 50 mL of Ensure), her stool volume decreased to 600 mL per day.

EXAMPLE IV

Administration of Active Lipid Increases Drug Bioavailability

Relatively rapid basal upper gut transit in Patients with Inflammatory Bowel Disease (IBD). The mean upper gut transit time for IBD patients (n=18) at 0 grams of oleic acid was 79.1±11.0 min., compared to 118.7±9.8 min for normal subjects (n=5)(p=0.04, t-test).

Measurement of basal drug bioavailability. The hypothesis that the bioavailability of oral drug is lower in IBD patients was tested by measuring serum levels of acetaminophen after oral administration of 1000 mg of this drug in a liquid formulation. Acetaminophen was chosen, because it is absorbed rapidly and almost exclusively and entirely in the proximal intestine; it is safe in a therapeutic dose range; and is only minimally bound to plasma proteins. After subjects ingested the drug, periodic samples of blood were collected from a plastic tube inserted into a vein in each subject's arm. The blood was then analyzed spectrophotometrically for concentration of acetaminophen. Peak plasma level, time to peak concentration and area under the curve (AUC; representing the plasma acetaminophen concentration over time) were derived from these data. Relative drug bioavailability was determined by comparing AUC values. In control experiments without oleic acid, IBD patients had a smaller AUC than normal subjects, consistent with lower acetaminophen bioavailability; the mean AUC for normal patients (n=5) was 1438.9±208.5. The mean AUC for IBD patients (n=18) was 687.3±98.2. (p<0.05, t-test).

Active lipid increases upper gut transit time and drug bioavailability. The mean transit time for normal subjects (n=5) at 0 grams of oleic acid was 118.7±9.8 min, at 4 grams of Oleic acid was 136.0±15.4 min. (P<0.05, t-test). The mean AUC for normal subjects at 0 grams of oleic acid was 1438.9±208.5; at 4 grams of oleic acid it was 1873.3±330.5 (p<0.05, t-test). The mean transit time for IBD patients (n=18) at 0 grams of oleic acid was 79.1±11.0 min; at 4 grams of oleic acid it was 114.6±16.0 min. (p<0.05, t-test). The mean AUC for IBD patients at 0 grams of oleic acid was 687.3±98.2; at 4 grams of oleic acid it was 1244.9±250.4. (p<0.05, t-test). These data show that oleic acid slowed gut transit time and increased bioavailability of the drug in both normal and IBD groups.

EXAMPLE V

Manipulation of the Rate of Upper Gastrointestinal Transit

The experiments described below are based on a previously described chronic multi-fistulated dog model, employing surgically fistulated male or female mongrel dogs weighing about 25 kg each. (Lin, H. C. et al., *Inhibition of gastric emptying by glucose depends on length of intestine exposed to nutrient*, Am. J. Physiol. 256:G404–G411 [1989]). The small intestines of the dogs were each about 300 cm long from the pylorus to the ileal-cecal valve. The duodenal fistula was situated 15 cm from the pylorus; the mid-gut fistula was situated 160 cm from the pylorus. Occluding Foley catheters (balloon catheters that are inflated to produce a water-tight seal with the luminal surface) were placed into the distal limb of a duodenal fistula and a mid-gut fistula, fat or other test agents were administered luminally to the thus compartmentalized "proximal" section of the gut, i.e., between the fistulas, or to the compartmentalized "distal" section of the gut, i.e., beyond the mid-gut fistula. Perfusate was pumped into a test section through the catheter at a rate of 2 mL/minute. Test agents were administered along with buffer perfusate, but some test agents were administered intravenously, where specifically noted.

Intestinal transit measurements were made by tracking the movement of a liquid marker across the approximately 150 cm intestinal test segment by delivering about 20 μCi $^{99m}$Tc chelated to diethyltriamine pentaacetic acid (DTPA)(Cunningham, K. M. et al., *Use of technicium-99m (V)thiocyanate to measure gastric emptying of fat*, J. Nucl. Med. 32:878–881 [1991]) as a bolus into the test segment after 60 minutes of a 90-minute perfusion. The output from the mid-gut fistula was collected every 5 min thereafter for 30 minutes, which period is illustrated in FIGS. 1–13. Using a matched dose of $^{99m}$Tc to represent the original radioactivity (Johansson, C., *Studies of gastrointestinal interactions*, Scand. J. Gastroenterol. 9(Suppl 28):1–60 [1974]; Zierler, K., *A simplified explanation of the theory of indicator dilution for measurement of fluid flow and volume and other distributive phenomena*, Bull. John Hopkins 103:199–217 [1958]), the radioactivity delivered into the animal as well as the radioactivity of the recovered fistula output were all measured using a gamma well counter. After correcting all counts to time zero, intestinal transit was calculated as the cumulative percent recovery of the delivered $^{99m}$Tc-DTPA. This method has been well validated over the years and appreciated for its advantage of minimal inadvertent marker loss. To demonstrate this point, we perfused phosphate buffer, pH 7.0, through the proximal gut and followed the cumulative recovery of this marker (% recovery) over time (n=1). There was a very high level of marker recovery, with 90% of the marker recovered by 30 minutes and 98% of the marker recovered by 45 minutes.

(1) Slowing of intestinal transit by PYY depends on ondansetron-sensitive 5-HT-mediated pathway. Peptide YY (PYY) slows transit and is a signal for luminal fat (Lin, H. C. et al., *Fat-induced ileal brake in the dog depends on peptide YY*, Gastroenterol. 110(5):1491–95 [1996b]; Lin, H. C. et al., *Slowing of intestinal transit by fat in proximal gut depends on peptide YY*, Neurogastroenterol. Motility 10:82 [1998]). Since serotonin (5-HT) can also be a signal for fat (Brown, N. J. et al., *The effect of a 5HT3 antagonist on the ileal brake mechanism in the rat*, J. Pharmacol. 43:517–19 [1991]; Brown, N. J. et al. [1993]), the hypothesis was tested that the slowing of transit by PYY can depend on a 5-HT-mediated pathway by comparing the rate of marker transit during the administration of PYY in the presence or absence of ondansetron (Ond; a 5-HT receptor antagonist) in the proximal versus distal gut (n=2 for each treatment).

Normal saline (0.15 M NaCl) or PYY (0.8 μg/kg/h) was administered intravenously over a 90 minute period, while phosphate buffer, pH 7.0, was perfused into the lumen of the proximal gut through the duodenal fistula at a rate of 2 mL/min for the 90 minutes and was recovered from the output of the mid-gut fistula. The results are summarized in FIG. 1. Transit was slowed by intravenous PYY, with recovery of the marker decreased from 75.1±3.6% (control: IV normal saline [NS]+luminal normal saline, i.e., NS—NS in FIG. 1) to 17.1±11.0% (IV PYY+luminal normal saline, i.e., PYY-NS in FIG. 1). This effect was abolished by adding the specific 5-HT receptor antagonist ondansetron (0.7 mg/kg/h) to the buffer introduced into the proximal gut so that recovery increased to 78.3±4.8% (IV PYY+luminal Ond proximal, i.e., PYY-Ond in prox in FIG. 1) but not by ondansetron in the distal gut, which decreased recovery to 12.9±12.9% (IV PYY+Ond in Distal, i.e., PYY-Ond in Dist). These results imply that slowing of transit by PYY depended on a 5-HT-mediated pathway located in the segment of the small intestine where transit was measured.

(2) The fat induced jejunal brake depends on an ondansetron-sensitive serotonin (5-HT)-mediated pathway. The hypothesis was tested that slowing of transit by fat depends on a serotonergic pathway by comparing intestinal transit during perfusion with buffer or oleate in the presence or absence of the ondansetron, a 5-HT receptor antagonist, in the proximal gut (n=3 each treatment). Buffer or 60 mM oleate was perfused through the duodenal fistula into the lumen of the proximal gut for a 90-minute period, in the manner described in Example V.(1), along with a bolus of normal saline±ondansetron (0.7 mg/kg) at the start of transit measurement. The rate of intestinal transit was slowed by the presence of oleate (p<0.05) in an ondansetron-sensitive manner. (p<0.05). The results are summarized in FIG. 2.

Figure 2:
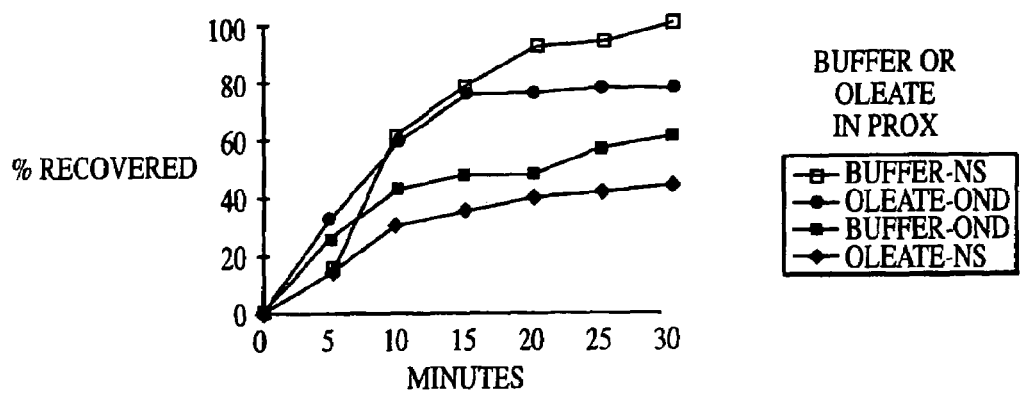
FIG. 2 demonstrates that demonstrates that slowing of the rate of intestinal transit by fat depends on a serotonergic pathway.
Figure 3:
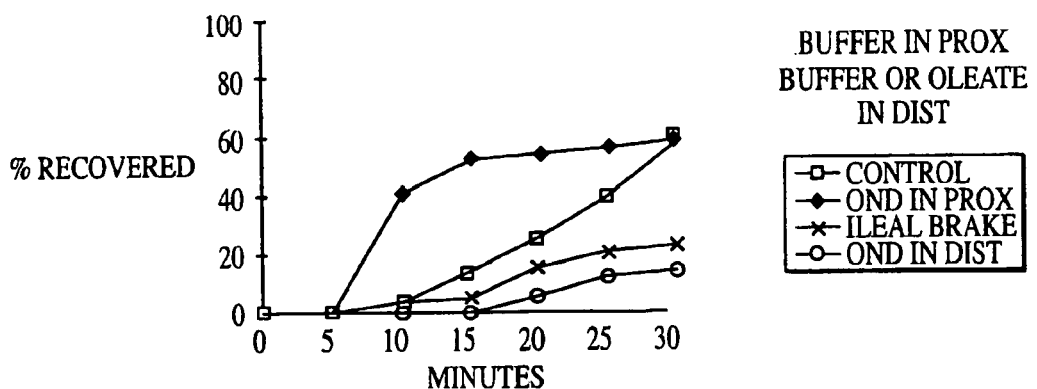
FIG. 3 illustrates that the fat induced ileal brake depends on an ondansetron-sensitive, efferent serotonin (5-HT)-mediated pathway.

Specifically, ondansetron increased recovery of marker in the perfusate from 41.6±4.6% (mean±SE) (luminal oleate+luminal normal saline, i.e., Oleate-NS in FIG. 2) to 73.7±10.6% (luminal oleate+luminal ondansetron, i.e., Oleate-Ond in FIG. 2) during oleate perfusion but decreased recovery from 96.0±4.0% (luminal phosphate buffer+luminal normal saline, i.e., Buffer-NS in FIG. 2) to 57.9±15.9% (luminal buffer+luminal ondansetron, i.e., Buffer-Ond in FIG. 2) during buffer perfusion. These results imply that slowing of intestinal transit by the fat-induced jejunal brake and the acceleration of intestinal transit by buffer distension both depended on an ondansetron-sensitve 5-HT-mediated pathway.

(3) The fat-induced ileal brake depends on an ondansetron-sensitive, efferent serotonin (5-HT)-mediated pathway. The fistulated dog model allows for the ileal brake (oleate in distal gut, buffer in proximal gut) to be separated into the afferent (distal) vs. efferent (proximal) limb of the response. By delivering ondansetron luminally into either the proximal or distal gut, intestinal transit was slowed by the ileal brake (66.4±1.5% [Control in FIG. 3] vs. 26.2±18.0% [Ileal Brake in FIG. 3]; p<0.05). But the ileal brake was abolished by ondansetron delivered to the proximal gut (62.5±10.1%; Ond in Prox in FIG. 3; n=4) but not distal gut (17.4±8.8%; Ond in Dist in FIG. 3; n=4). These results imply that the slowing of intestinal transit by fat in the distal gut depends on an efferent, 5-HT-mediated pathway. Since ondansetron abolished the jejunal brake in Example V.(1) when delivered with fat and abolished the ileal brake in Example V.(2) when delivered with buffer, this region-specific result cannot be explained by inactivation of drug by fat, differences in permeability or absorption.

(4) Ondansetron abolishes the fat-induced ileal brake in a dose-dependent manner. The fat-induced ileal brake was abolished by the 5-HT receptor antagonist ondansetron in a dose-dependent manner. Perfusion of buffer was through both the duodenal and mid-gut fistulas (2 mL/min over 90 minutes); the buffer administered to the mid-gut fistula contained normal saline (Buffer Control in FIG. 4) or 60 mM oleate to induce the ileal brake response (Ileal Brake in FIG. 4). During the ileal brake response, ondansetron was added at $t_0$ as a single bolus in the following doses (mg): 6.25; 12.5; and 25. Results are shown in FIG. 4.

Figure 4:
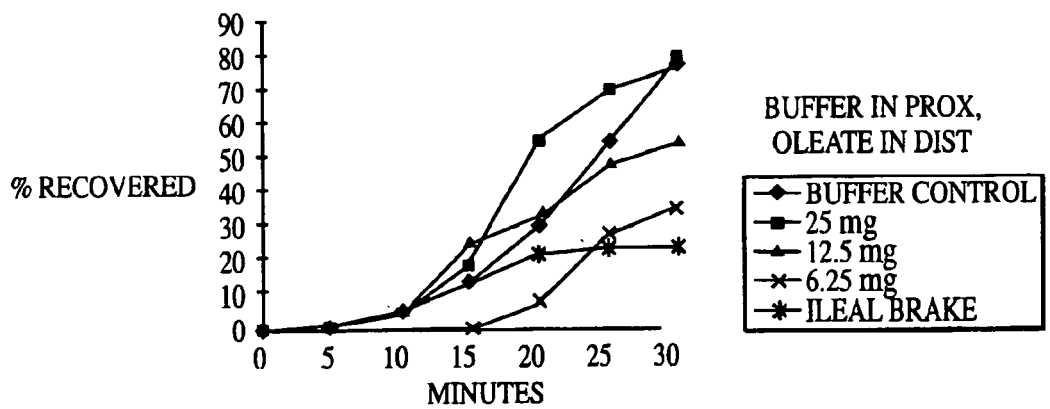
FIG. 4 shows that ondansetron abolishes the fat-induced ileal brake in a dose-dependent fashion.
Figure 5:
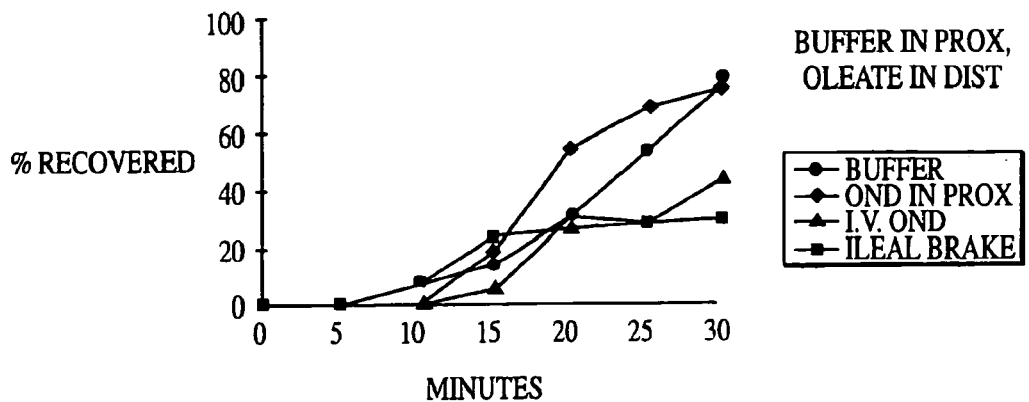
FIG. 5 shows that ondansetron abolishes the fat-induced ileal brake when administered luminally but not intravenously.
Figure 6:
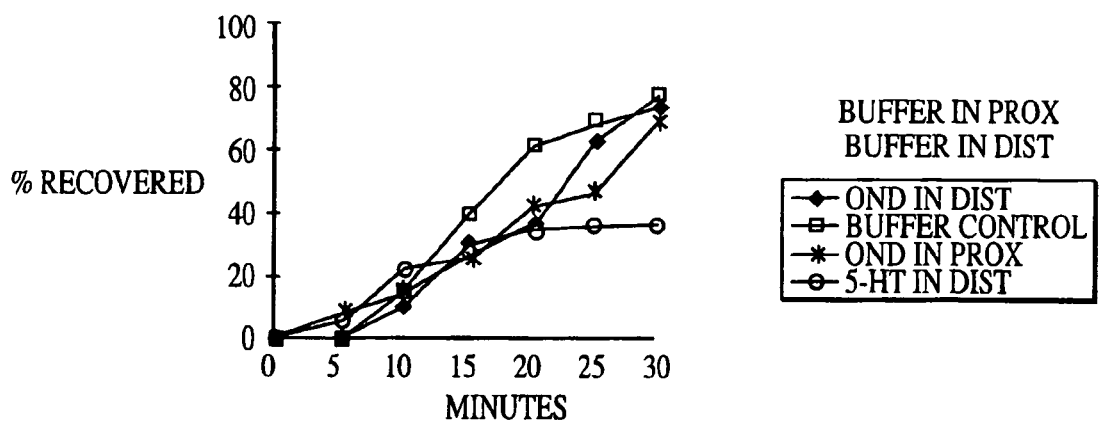
FIG. 6 illustrates that the slowing of intestinal transit by distal gut 5-HT depends on an ondansetron-sensitive 5-HT-mediated pathway in the proximal (efferent) and distal (afferent) gut.

Oleate induced the ileal brake (24.1% marker recovery [Ileal brake in FIG. 4] vs. 81.2% marker recovery for the Buffer Control). The ileal brake was abolished by ondansetron delivered into the proximal gut in a dose-dependent manner (35.4% marker recovery at 6.25 mg ondansetron, 55.8% marker recovery at 12.5 mg ondansetron, and 77.6% marker recovery at 25 mg ondansetron).

(5) Fat in the distal gut causes the release of 5-HT from the proximal gut. To test the hypothesis that fat in the distal gut causes the release of 5-HT in the proximal gut, the amount of 5-HT collected from the output of the mid-gut fistula (proximal gut 5-HT) over a 90-minute period of buffer perfusion through both the duodenal and mid-gut fistulas (2 mL/min); buffer (control) or oleate (60 mM) was administered to the distal gut (n=1). The amount of 5-HT was determined using an ELISA kit specific for 5-HT (Sigma; Graham-Smith, D. G., *The carcinoid syndrome*, In: *Topics in Gastroenterology*, Truclove, S. C. and Lee, E. (eds.); Blackwells, London, p. 275 [1977]; Singh, S. M. et al., *Concentrations of serotonin in plasma—a test for appendicitis?*, Clin. Chem. 34:2572–2574 [1988]). The amount of 5-HT released by the proximal gut increased in response to fat in the distal gut from 100 µg in the control (buffer minus oleate) to 338 µg (buffer plus oleate to distal gut), showing that 5-HT is released in the proximal gut in response to fat in the distal gut. Thus, the release of 5-HT by the proximal gut can serve as a relayed signal for fat in the distal gut. The relayed release of 5-HT in the proximal gut in response to fat in the distal gut is consistent with Example V.(2), showing that slowing of intestinal transit by fat depends on an efferent 5-HT-mediated pathway to the proximal gut.

(6) Ondansetron abolishes the fat-induced ileal brake when administered luminally but not intravenously. To test the hypothesis that the effect of ondansetron is peripheral rather than systemic, ondansetron (0.7 mg/kg/h) was either delivered through the duodenal fistula into the proximal gut (luminal ondansetron, i.e., Ond in prox in FIG. 5) or administered intravenously (i.e., iv Ond in FIG. 5) during fat-induced ileal brake (60 mM oleate input through the mid-gut fistula into the distal gut as described above; n=1). Compared to ileal brake (29% marker recovered), the marker recovery increased to 78% with luminal ondansetron, but intravenous ondansetron had no effect (43% marker recovery). This implies that the 5-HT receptor antagonist worked peripherally (gut) rather than systemically.

(7) The slowing of intestinal transit by distal gut 5-HT depends on an ondansetron-sensitive 5-HT-mediated pathway in the proximal gut (efferent) and distal gut (afferent). To test the hypothesis that intestinal transit is slowed by 5-HT in the distal gut via a 5-HT-mediated pathway(s), intestinal transit with 5-HT (0.05 mg/kg/h) administered to the distal gut was measured to compare the effect of ondansetron (0.7 mg/kg) administered in a bolus either in the proximal gut or distal gut (n=2 each treatment). The results are summarized in FIG. 6. Marker recovery decreased from 75.1±2.5% (Buffer Control in FIG. 6) to 35.8±2.1% (buffer+5-HT in the distal gut, minus ondansetron, i.e., 5-HT in Dist in FIG. 6) but this slowing effect was abolished by ondansetron administered to either the proximal gut (70.6±3.5% recovery; Ond in Prox in FIG. 6) or distal gut (76.9±4.2% recovery; Ond in Dist in FIG. 6). These results imply that distal gut 5-HT slows intestinal transit via 5-HT3 receptor-dependent pathways in both afferent (distal) and efferent (proximal) limb of the response. (See also, Brown, N. J. et al., *Granisetron and ondansetron: effects on the ileal brake mechanism in the rat*, J. Pharm. Pharmacol. 45(6): 521–24 [1993]). This result contrasts with that for fat in the distal gut (see, Example V.[3]) to imply that the afferent limb of the response to fat involves a signal other than 5-HT, such as PYY.

(8) 5-HT in the distal gut slows intestinal transit in a dose-dependent manner. Intestinal transit during buffer perfusion of both the proximal and distal guts (81.2% recovery) was slowed by 5-HT in distal gut so that marker recovery decreased to 73.8% at 2 mg 5-HT (0.033 mg 5-HT/kg/h), 53.1% at 3 mg (0.05 mg 5-HT/kg/h) and 11.6% at 4 mg (0.066 mg 5-HT/kg/h) dose over a 90 minute period (n=1).

(9) 5-HT in the distal gut causes release of 5-HT in the proximal gut. To test the hypothesis that 5-HT in the distal gut causes the release of 5-HT in the proximal gut, the amount of 5-HT collected from the output at the mid-gut fistula (Proximal gut 5-HT) over a 90-minute period of buffer perfusion through both the duodenal and mid-gut fistulas (2 mL/min each) was compared in the presence or absence of 5-HT (0.05 mg/kg/h) administered to the distal gut (n=1). 5-HT concentration was determined using an ELISA kit specific for 5-HT (Sigma). The amount of 5-HT released by the proximal gut increased from 156 µg in the control (minus distal 5-HT) to 450 µg (plus 5-HT to distal gut), implying that 5-HT is released by the proximal gut in response to 5-HT in the distal gut. Thus, the release of 5-HT by the proximal gut can serve as a relayed signal for distal gut 5-HT. This relayed release of 5-HT in the proximal gut explains the results of Example V.(6) showing that the slowing of intestinal transit by distal gut 5-HT was abolished by ondansetron in the proximal gut (efferent limb of response) as well as in the distal gut (afferent limb of response).

(10) Intravenous PYY causes release of 5-HT in the proximal gut. The amount of 5-HT released from the proximal gut in response to intravenous PYY or saline (Control) during buffer perfusion (2 mL/min over 90 minutes) through both the duodenal and mid-gut fistulas was measured to test the hypothesis that intravenous PYY (0.8 mg/kg/h) causes the release of 5-HT in the proximal gut. 5-HT was measured as in Example V.(9) above. The amount of 5-HT released by the proximal gut increased from 140.1 µg (Control) to 463.1 µg in response to intravenous PYY.

This result was comparable with the response when 60 mM oleate was administered to the distal gut (buffer only to the proximal gut) during the perfusion without intravenous PYY (509.8 µg of 5-HT; n=1), which implies that the release of 5-HT in the proximal gut stimulated by fat in the distal gut can be mediated by PYY.

(11) Slowing of intestinal transit by fat in the distal gut depends on an extrinsic adrenergic neural pathway. A distension-induced intestino-intestinal inhibitory neural reflex projects through the celiac prevertebral celiac ganglion via a cholinergic afferent and an adrenergic efferent (Szurszewski, J. H. and King, B. H., *Physiology of prevertebral ganglia in mammals with special reference to interior mesenteric ganglion*, In: Handbook of Physiology: The Gastrointestinal System, Schultz, S. G. et al. (eds.), American Physiological Society, distributed by Oxford University Press, pp. 519–592 [1989]). Intestinal transit was measured during fat perfusion of the distal small intestine in the presence or absence of intravenous propranolol (50 µg/kg/h; n=2), a β-adrenoceptor antagonist, to test the hypothesis that the slowing of intestinal transit by fat in the distal gut also depends on an adrenergic pathway. Perfusion of buffer was through both the duodenal and mid-gut fistulas (2 mL/min over 90 minutes); the buffer administered to the mid-gut fistula contained 60 mM oleate. The results are illustrated in FIG. 7.

Figure 7:
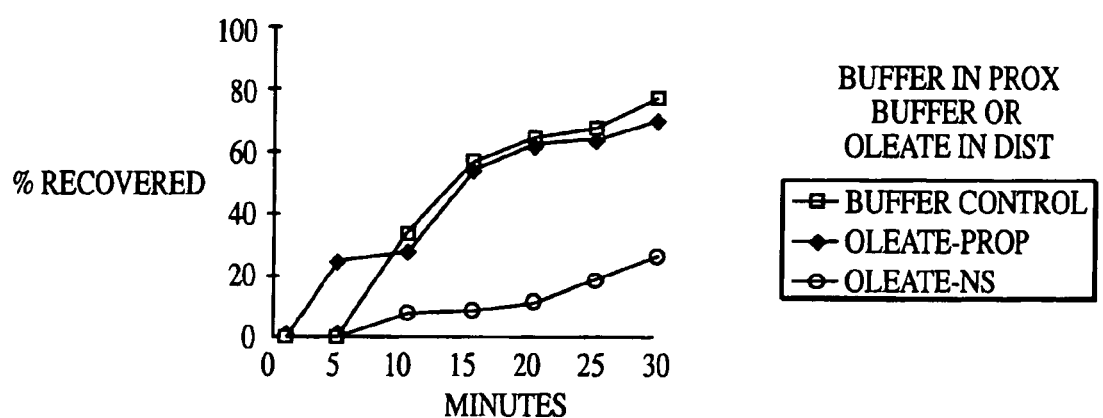
FIG. 7 illustrates that slowing of intestinal transit by distal gut fat depends on an extrinsic adrenergic neural pathway.
Figure 8:
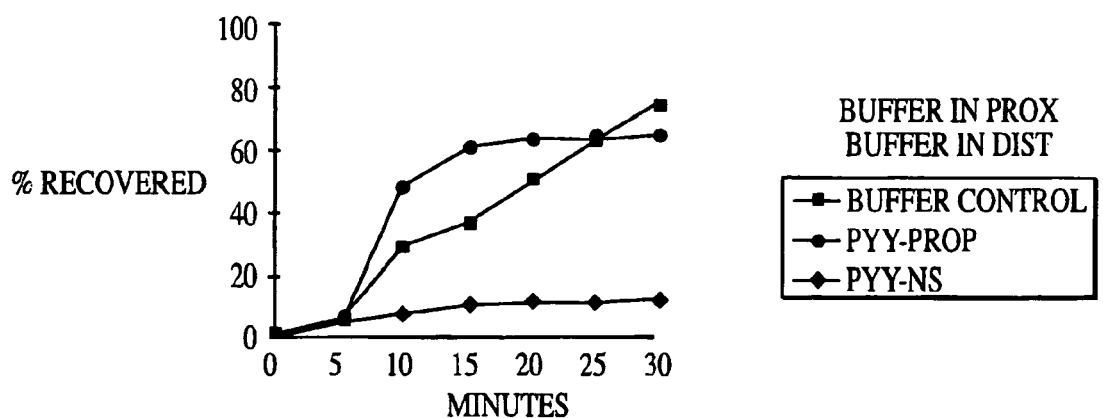
FIG. 8 illustrates that slowing of intestinal transit by PYY depends on an extrinsic adrenergic neural pathway.
Figure 9:
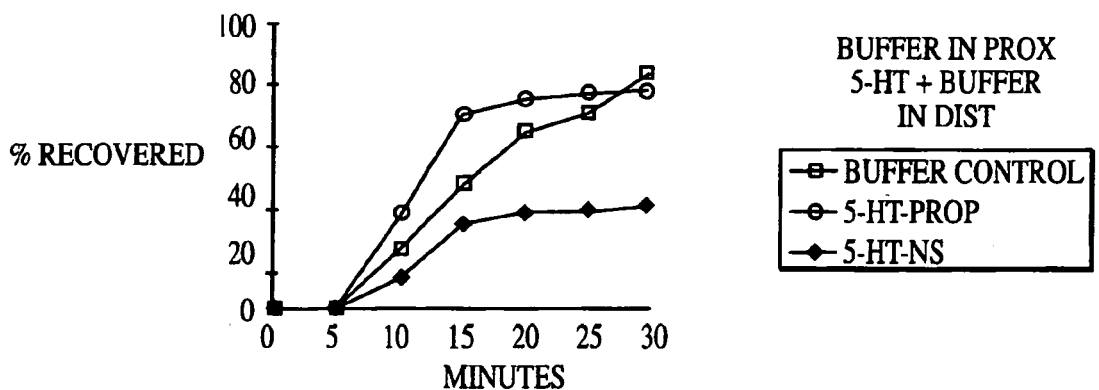
FIG. 9 illustrates that slowing of intestinal transit by 5-HT in the distal gut depends on an extrinsic adrenergic neural pathway.

Intestinal transit was slowed by distal gut fat (79.7±5.8% marker recovery [Buffer Control in FIG. 7] compared to 25.8±5.2% recovery with fat perfusion into the distal gut [Oleate-NS in FIG. 7]). Intravenous propranolol abolished this jejunal brake effect so that recovery increased to 72.1±4.7% (oleate+propranolol, i.e., Oleate-Prop in FIG. 7), implying that the slowing of transit by fat in the distal gut depends on a propranolol-sensitive, adrenergic pathway. This result supports the hypothesis that the response to fat involves an adrenergic efferent, such as the extrinsic nerves projecting through the prevertebral ganglia.

(12) Slowing of intestinal transit by PYY depends on an extrinsic adrenergic neural pathway. Intestinal transit during buffer perfusion of the proximal and distal small intestine in the presence or absence of intravenous propranolol (50 µg/kg/h; n=2) was measured, to test the hypothesis that the slowing of intestinal transit by PYY (a fat signal) also depends on an adrenergic pathway. Perfusion was through both fistulas as described in Example V.(11) except that oleate was not administered to the distal gut, and, instead, 30 µg PYY (0.8 mg/kg/h) was administered intravenously during the 90 minute perfusion period. The results are summarized in FIG. 8.

Slowing of intestinal transit by PYY (78.1±2.2% marker recovery minus PYY [Buffer Control in FIG. 8] vs. 11.8±5.4% recovery with intravenous PYY [PYY-NS in FIG. 8]) was abolished by intravenous propranolol. In the presence of propranolol, marker recovery increased to 66.3±3.1% (PYY-Prop in FIG. 8). This result implies that the slowing of transit by PYY depends on a propranolol-sensitive, adrenergic pathway, which supports the hypothesis that the response to PYY involves an adrenergic efferent such as the extrinsic nerves projecting through the prevertebral ganglia.

(13) Slowing of intestinal transit by 5-HT in the distal gut depends on an extrinsic adrenergic neural pathway. Intestinal transit during buffer perfusion of the proximal and distal small intestine in the presence or absence of intravenous propranolol (50 µg/kg/h; n=2) was measured, to test the hypothesis that the slowing of intestinal transit by 5-HT in the distal gut also depends on an adrenergic pathway. Buffer perfusion was through both fistulas as described in Example V.(12) except that 5-HT (0.05 mg/kg/h) was administered to the distal gut during the 90 minute perfusion period. The results are summarized in FIG. 9.

Slowing of intestinal transit by 5-HT (83.3±3.3% marker recovery minus 5-HT [Buffer Control in FIG. 9] vs. 36.1±2.3% recovery with administration of 5-HT to the distal gut [5-HT-NS in FIG. 9]) was abolished by intravenous propranolol. In the presence of propranolol, marker recovery increased to 77.7±7.6% (5-HT-Prop in FIG. 9). This result implies that the slowing of transit by 5-HT depends on a propranolol-sensitive, extrinsic adrenergic pathway, perhaps similar to that responsible for the response to distal gut fat.

(14) Intestinal transit is slowed by norepinephrine in a 5-HT-mediated neural pathway. Intestinal transit during buffer perfusion of the proximal and distal small intestine with intravenous norepinephrine (NE; adrenergic agent) in the presence or absence of the 5-HT receptor antagonist ondansetron was measured, to test the hypothesis that the slowing of intestinal transit also depends on an adrenergic efferent pathway. Perfusion of buffer was through both the duodenal and mid-gut fistulas (2 mL/min over 90 minutes); norepinephrine (0.12 µg/kg/h) was administered intravenously during the 90 minute perfusion period; and normal saline with or without ondansetron (0.7 mg/kg/h; n=2) was administered in the perfusate to the proximal gut. The results are summarized in FIG. 10.

Figure 10:
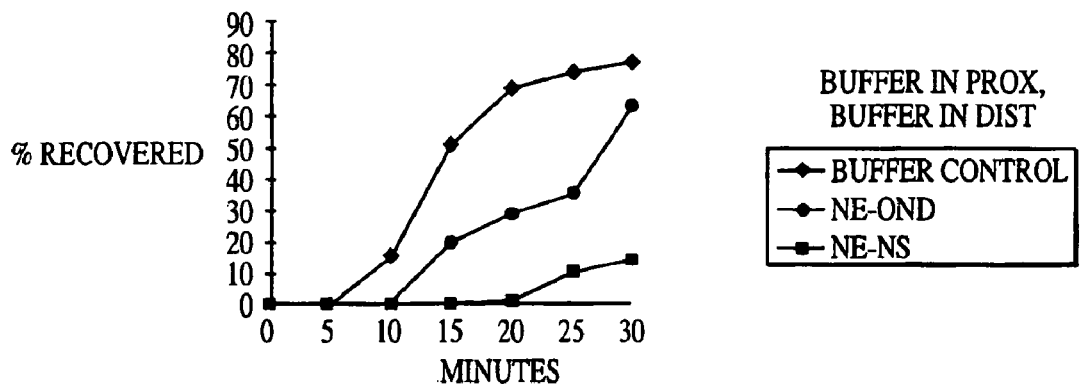
FIG. 10 illustrates that intestinal transit is slowed by norepinephrine (NE) in a 5-HT-mediated neural pathway.

Intestinal transit was slowed by NE so that marker recovery was reduced from 76.9% (Buffer Control in FIG. 10) to 13.3% (NE-NS in FIG. 10). Ondansetron abolished this slowing effect with marker recovery increased to 63.4% (NE-Ond in FIG. 10), to implies that NE (adrenergic efferent) slows transit via a 5-HT-mediated pathway. This result confirms that slowing of intestinal transit is mediated by an adrenergic efferent projecting from the prevertebral ganglion to the gut action on a 5-HT-mediated pathway.

Figure 11:
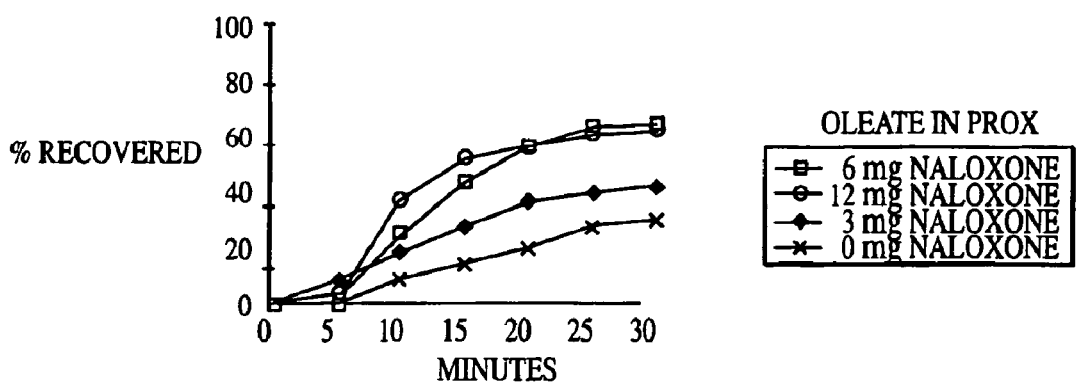
FIG. 11 illustrates that the fat-induced jejunal brake depends on the slowing effect of a naloxone-sensitive, opioid neural pathway.

(15) The fat-induced jejunal brake depends on the slowing effect of a naloxone-sensitive, opioid neural pathway. To test the hypothesis that the slowing of intestinal transit depended on an opioid pathway, the proximal gut was perfused (2 mL/minute for 90 minutes) with buffer containing 60 mM oleate and 0 (normal saline), 3, 6, or 12 mg of naloxone mixed therein, an opioid receptor antagonist. As shown in FIG. 11, the fat-induced jejunal brake response depended on the dose of naloxone mixed with the oleate (p<0.05, 1-way ANOVA)(n=7). Specifically, marker recovery was 30.0±3.6% with 0 mg naloxone, 41.0±5.2% with 3 mg naloxone, 62.8±8.2% with 6 mg naloxone and 60.6±6.1% with 12 mg naloxone. This result demonstrates that proximal gut fat slows intestinal transit via opioid pathway.

(16) The effect of naloxone was specific for fat-triggered feedback. Intestinal transit was compared during perfusion of the proximal gut with buffer containing 0 (normal saline) or 6 mg naloxone (n=3). The rate of intestinal transit was not significantly affected by the opioid receptor antagonist naloxone when fat was not present in the proximal gut. Marker recovery was 88.0±1.3% with naloxone and 81.3±6.1% without naloxone. This implies that the accelerating effect of naloxone was specific for reversing the jejunal brake effect of fat.

(17) The fat-induced ileal brake depends on the slowing effect of an efferent, naloxone-sensitive, opioid neural pathway. The fistulated dog model allowed for the compartmentalization of the afferent limb (distal gut) from efferent limb (proximal gut) of the fat-induced ileal brake. To test for the location of the opioid pathway involved in the slowing of transit by fat, perfusion of buffer was through both the duodenal and mid-gut fistulas (2 mL/min over 90 minutes); the buffer administered through the mid-gut fistula to the distal gut contained 60 mM oleate to induce the ileal brake; 6 mg naloxone was delivered into either the proximal or distal gut (n=11). The results are summarized in FIG. 12.

Figure 12:
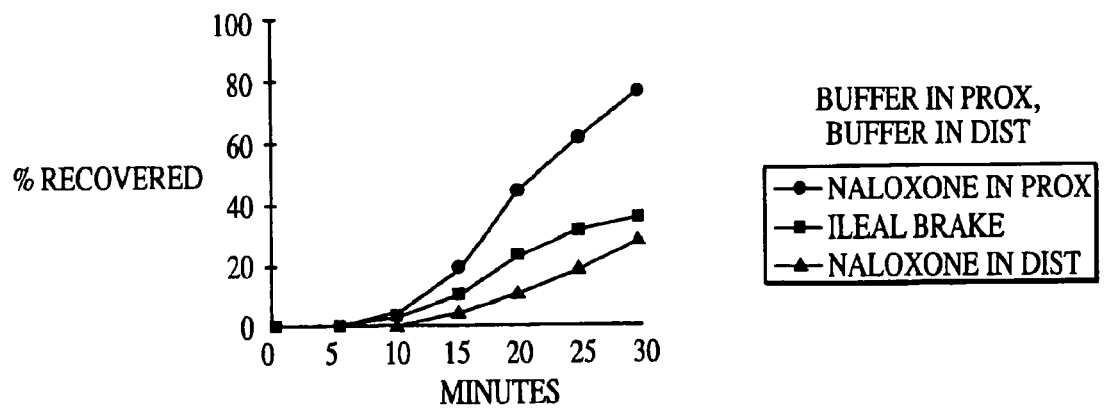
FIG. 12 illustrates that the fat-induced ileal brake depends on the slowing effect of an efferent, naloxone-sensitive, opioid neural pathway.
Figure 13:
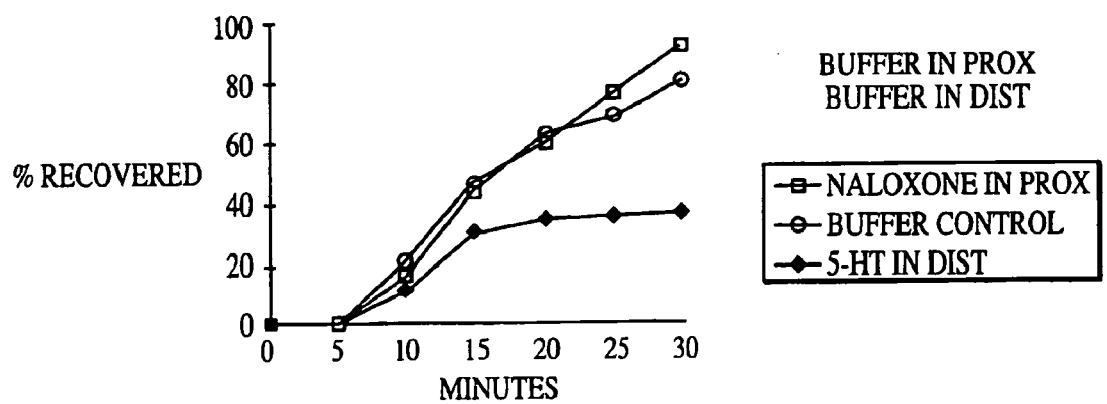
FIG. 13 shows that slowing of intestinal transit by distal gut 5-HT depends on a naloxone-sensitive, opioid neural pathway.

Naloxone delivered to the proximal gut increased marker recovery from 34.6±4.8% to 76.2±5.2% (Naloxone in Prox in FIG. 12), but naloxone delivered to the distal gut had no effect on the ileal brake (marker recovery of 29.4±5.4% [Naloxone in Dist in FIG. 12]). This result implies that the fat-induced ileal brake depends on an efferent, naloxone-sensitive opioid pathway, because an identical amount of naloxone was delivered into either of the two compartments, but the accelerating effect only occurred when naloxone was delivered into the efferent compartment. Therefore, an opioid pathway is involved that is located peripherally, rather than systemically. The accelerating effect in response to the opioid receptor antagonist is a result of the efferent location of the opioid pathway. It cannot be explained on the basis of chemical interaction with the perfusate, since the acceleration of transit was seen when naloxone was mixed with oleate in Example V.(15), as well as with buffer in this experiment.

(18) Mu and kappa opioid antagonists abolish fat-induced ileal brake. The fat-induced ileal brake (marker recovery 33.1%) was abolished by a mu antagonist (H2186, Sigma) delivered into the proximal gut so that marker recovery increased to 43.8% at 0.037 mg H2186, 88.2% at 0.05 mg H2186 and 66.8% at 0.1 mg H2186 over 90 minutes. A similar effect was seen when a kappa antagonist (H3116, Sigma) was used (marker recovery increased to 73.2%% at 0.075 mg H3116, 90.9% at 0.1 mg H3116, and 61.8% at 0.125 mg H3116 over 90 minutes; n=1).

(19) Slowing of intestinal transit by distal gut 5-HT depends on a naloxone-sensitive, opioid neural pathway. In Example V.(5), 5-HT in the distal gut slowed intestinal transit, similar to the effect of fat in the distal gut. Since the ileal brake induced by fat in the distal gut was shown to depend on an efferent, naloxone-sensitive opioid pathway (Example V.(17), it was tested whether the slowing of intestinal transit in response to 5-HT in the distal gut also depends on an efferent, opioid pathway. Buffer was perfused into both the proximal and distal guts at 2 mL/minute for 90 minutes. Either normal saline (Buffer Control in FIG. 13) or 5-HT (0.05 mg/kg/h; 5-HT in Dist in FIG. 13) was administered to the distal gut over the 90 minute perfusion. When the perfusate to the distal gut contained 5-HT (i.e., 5-HT in Dist), naloxone (6 mg) was simultaneuosly delivered through the duodenal fistula to the proximal gut over the 90 minutes (Naloxone in Prox in FIG. 13). Results are summarized in FIG. 13.

First, intestinal transit was slowed by 5HT in the distal gut. Marker recovery was reduced from 79.4±4.1% (Buffer Control) to 37.0±1.8% (5-HT in Dist). Second, naloxone in proximal gut abolished this slowing effect with marker recovery increased to 90.1±4.6% (Naloxone in Prox). These results imply that slowed intestinal transit in response to 5-HT in the distal gut, depends on an efferent opioid pathway.

Although the invention has been described with reference to the disclosed embodiments, those skilled in the art will readily appreciate that the specific embodiments taught hereinabove are only illustrative of the invention. It should be understood that various modifications can be made without departing from the spirit of the invention.

What is claimed is:

1. A method of manipulating the rate of upper gastrointestinal transit of a substance in a mammal having an intrinsic cholinergic afferent neural pathway projecting from a peptide YY-sensitive primary sensory neuron in the intestinal wall to a prevertebral celiac ganglion and having an adrenergic efferent neural pathway projecting from said ganglion to one or more enterochromaffin cells in the intestinal mucosa and/or to a serotonergic interneuron linked in a myenteric plexus and/or submucous plexus to an opioid interneuron, said opioid intemeuron also being linked by an intestino-fugal opioid pathway projecting to said ganglion, with one or more neural connections to the central nervous system and back to the gut projecting from the ganglion, said method comprising:
    providing a pharmaceutically acceptable composition, comprising an active agent selected from the group consisting of
        (A) peptide YY, and
        (B) antagonists of receptors for (A); and
    administering the pharmaceutically acceptable composition to the mammal,
    said active agent being delivered in an amount and under conditions such that the cholinergic intestino-fugal pathway, at least one prevertebral ganglionic pathway, the adrenergic efferent neural pathway, the serotonergic intemeuron and/or the opioid interneuron are activated by the action of (A), whereby the rate of upper gastrointestinal transit is slowed, or such that activation of the cholinergic intestino-fugal pathway, at least one prevertebral ganglionic pathway, the adrenergic efferent neural pathway, the serotonergic intemeuron and/or the opioid intemeuron is blocked by the action of (B), whereby the rate of upper gastrointestinal transit is accelerated.

2. The method of claim 1, wherein administering the pharmaceutically acceptable composition to the mammal further comprises administering the pharmaceutically acceptable composition by a delivery route selected from the group consisting of oral, intravenous, intraperitoneal, and nasal.

3. A method of manipulating satiety in a mammalian subject having a cholinergic afferent neural pathway projecting from a peptide YY-sensitive primary sensory neuron in the intestinal wall to a prevertebral celiac ganglion and having an adrenergic efferent neural pathway projecting from said ganglion to one or more enterochromaffin cells in the intestinal mucosa and/or to a serotonergic interneuron linked in amyenteric plexus to an opioid interneuron, said opioid interneuron also being linked by an intestino-fugal opioid pathway projecting to said ganglion, with one or more neural connections to the central nervous system and back to the gut projecting from the ganglion, said method comprising:
providing a pharmaceutically acceptable composition, comprising an active agent selected from the group consisting of
(A) peptide YY, and
(B) antagonists of receptors for (A); and
administering the pharmaceutically acceptable composition to the mammal,
said active agent being delivered in an amount and under conditions such that the cholinergic intestino-fugal pathway, one or more prevertebral ganglionic pathways, adrenergic efferent neural pathway, the serotonergic interneuron and/or the opioid interneuron are activated by the action of (A), whereby a state of satiety is induced, or such that activation of the cholinergic intestino-fugal pathway, prevertebral ganglionic pathways, ganglion to central nervous system pathways, central nervous system pathways, adrenergic efferent neural pathway, the serotonergic interneuron and/or the opioid interneuron is blocked by the action of (B), whereby satiety is suppressed.

4. The method of claim 3, wherein a neuronal pathway projecting from said ganglion to the hypothalamus of the subject is activated by the action of any of (A) on the primary sensory neuron.

5. The method of claim 3, wherein administering the pharmaceutically acceptable composition to the mammal further comprises administering the pharmaceutically acceptable composition by a delivery route selected from the group consisting of oral, intravenous, intraperitoneal, and nasal.

6. A method of inducing satiety in a mammal having an intrinsic cholinergic afferent neural pathway projecting from a peptide YY-sensitive primary sensory neuron in the intestinal wall to a prevertebral celiac ganglion and having a adrenergic efferent neural pathway projecting from said ganglion to one or more enterochromaffin cells in the intestinal mucosa and/or to a serotonergic interneuron linked in a myenteric plexus and/or submucous plexus to an opioid interneuron, said opioid interneuron also being linked by anintestino-fugal opioid pathway projecting to said ganglion, with one or more neural connections to the central nervous system and back to the gut projecting from the ganglion, said method comprising:
providing a pharmaceutically acceptable composition, comprising peptide YY; and
administering the pharmaceutically acceptable composition to the mammal,
said peptide YY being delivered in an amount and under conditions such that the cholinergic intestino-fugal pathway, prevertebral ganglionic pathways, ganglion to central nervous system pathways, adrenergic efferent neural pathway, the serotonergic interneuron and/or the opioid interneuron are activated by the action of said peptide YY, whereby a state of satiety is induced in the mammal.

7. The method of claim 6, wherein a neuronal pathway from said ganglion to the hypothalamus of the mammal is activated by the action of said peptide YY on the primary sensory neuron.

8. The method of claim 6, wherein administering the pharmaceutically acceptable composition to the mammal further comprises administering the pharmaceutically acceptable composition by a delivery route selected from the group consisting of oral, intravenous, intraperitoneal, and nasal.

9. A method of treating visceral pain or visceral hypersensitivity in a human subject having a cholinergic afferent neural pathway projecting from a peptide YY-sensitive primary sensory neuron in the intestinal wall to a prevertebral celiac ganglion and having a adrenergic efferent neural pathway projecting from said ganglion to one or more enterochromaffin cells in the intestinal mucosa and/or to a serotonergic interneuron linked in a myenteric plexus to an opioid interneuron, said opioid interneuron also being linked by an intestino-fugal opioid pathway projecting to said ganglion, with one or more neural connections to the central nervous system and back to the gut projecting from the ganglion, said method comprising:
providing a pharmaceutically acceptable composition, comprising peptide YY; and
administering the pharmaceutically acceptable composition to the mammal,
said peptide YY being delivered in an amount and under conditions such that activation of a cholinergic intestino-fugal pathway, one or more prevertebral ganglionic pathways, a gangalion to central nervous system pathway, the adrenergic efferent neural pathway, the serotonergic interneuron and/or the opioid interneuron is substantially reduced by the action of said peptide YY, whereby the sensation of esophageal, gastric, biliary, intestinal, colonic or rectal pain experienced by the human subject is reduced.

10. The method of claim 9, wherein administering the pharmaceutically acceptable composition to the mammal further comprises administering the pharmaceutically acceptable composition by a delivery route selected from the group consisting of oral, intravenous, intraperitoneal, and nasal.

11. A method of manipulating post-prandial visceral blood flow to the gastrointestinal tract of a mammal having a cholinergic afferent neural pathway projecting from a peptide YY-sensitive primary sensory neuron in the intestinal wall to a prevertebral celiac ganglion and having an adrenergic efferent neural pathway projecting from said ganglion to one or more enterochromaffin cells in the intestinal mucosa and/or to a serotonergic interneuron linked in a myenteric plexus to an opioid interneuron, said opioid interneuron also being linked by an intestino-fugal opioid pathway projecting to said ganglion, with additional neural connections to the central nervous system and back to the gut projecting from the ganglion, comprising:
providing a pharmaceutically acceptable composition, comprising an active agent selected from the group consisting of
(A) peptide YY, and
(B) antagonists of receptors for (A); and
administering the pharmaceutically acceptable composition to the mammal, said active agent being delivered in an amount and under conditions such that the cholinergic intestino-fugal pathway, prevertebral ganglionic pathways, gangalion to central nervous system pathways, central nervous system pathways, adrenergic efferent neural pathway, the serotonergic interneuron and/or the opioid intemeuron are activated by the action of (A), whereby the flow of blood to the gastrointestinal tract is increased, or such that activation of the cholinergic intestino-fugal pathway, prevertebral ganglionic pathways, gangalion to central nervous system pathways, the adrenergic efferent neural pathway, the serotonergic intemeuron and/or the opioid intemeuron is blocked by the action of (B), whereby the flow of blood to the gastrointestinal tract is decreased.

12. The method of claim 11, wherein administering the pharmaceutically acceptable composition to the mammal further comprises administering the pharmaceutically acceptable composition by a delivery route selected from the group consisting of oral, intravenous, intraperitoneal, and nasal.

* * * * *

UNITED STATES PATENT AND TRADEMARK OFFICE
CERTIFICATE OF CORRECTION

PATENT NO. : 7,081,239 B2
APPLICATION NO. : 10/810020
DATED : July 25, 2006
INVENTOR(S) : Henry C. Lin It is certified that error appears in the above-identified patent and that said Letters Patent is hereby corrected as shown below:

On The Title Page

On page 2 in "U.S. Patent Documents" Column 1, Line 42, delete "5,759,565 A 6/1998 Azria et al." and insert -- 5,759,656 A 6/1998 Collette --.

On page 2 in "U.S. Patent Documents" Column 1, Line 55, delete "5,883,529 A 3/1999 Kumata et al." and insert -- 5,863,529 A 1/1999 Rodriguez --.

On page 2 in "Foreign Patent Documents" Column 2, Line 33, delete "EP 1 468 610 A1 10/2004" and insert -- EP 1 466 610 A1 10/2004 --.

On page 2 in "Foreign Patent Documents" Column 2, Line 61, delete "WO WO 01/76831 A2 10/2001" and insert -- WO WO 01/76631 A2 10/2001 --.

On page 3 in "Other Publications" Column 1, Line 19, delete "discorders" and insert -- disorders --.

On page 3 in "Other Publications" Column 2, Line 13, delete "Vo" and insert -- Vol. --.

On page 3 in "Other Publications" Column 2, Line 48, delete "Brian" and insert -- Brain --.

On page 4 in "Other Publications" Column 2, Line 15, delete "Evicence" and insert -- Evidence --.

On page 4 in "Other Publications" Column 2, Line 62, delete "Propulation" and insert -- Population --.

On page 5 in "Other Publications" Column 1, Line 63, delete "Diseases" and insert -- Disease --.

On page 5 in "Other Publications" Column 2, Line 19, delete "Form" and insert --From--.

On page 6 in "Other Publications" Column 1, Line 53, delete "Carbon-D-Xylose" and insert -- Carbon-14-D-Xylose --.

UNITED STATES PATENT AND TRADEMARK OFFICE
CERTIFICATE OF CORRECTION

PATENT NO. : 7,081,239 B2
APPLICATION NO. : 10/810020
DATED : July 25, 2006
INVENTOR(S) : Henry C. Lin It is certified that error appears in the above-identified patent and that said Letters Patent is hereby corrected as shown below:

On page 6 in "Other Publications" Column 2, Line 47, delete "80-95" and insert -- 90-95 --.

On page 6 in "Other Publications" Column 2, Line 40, delete "Injfections" and insert -- Injections --.

On page 7 in "Other Publications" Column 2, Line 48, delete "(FK508)" and insert -- (FK506) --.

On page 8 in "Other Publications" Column 1, Lines 38-39, delete "Tretment" and insert -- Treatment --.

On page 9 in "Other Publications" Column 1, Line 63, delete "and .;".

On page 11 in "Other Publications" Column 2, Line 18, after "Alpha, IL-1" insert -- Beta, IL-1 --.

On page 12 in "Other Publications" Column 2, Line 19, delete "Diarrhoea" and insert -- Diarrhea --.

On page 14 in "Other Publications" Column 2, Line 31, delete "Flexin" and insert -- Flex in --.

On page 15 in "Other Publications" Column 1, Line 52, delete "Jansenm" and insert -- Jansen --.

On page 15 in "Other Publications" Column 1, Line 40, delete "Ghatei" and insert -- Ghatel --.

In The Specification:

Column 1, Lines 24-25, delete "PCT/US01/1 1238 filed Mar. 07, 2001" and insert -- PCT/US01/11230 filed April 7, 2001 --.

Column 2, Lines 2-3, there should be no new paragraph.

UNITED STATES PATENT AND TRADEMARK OFFICE
CERTIFICATE OF CORRECTION

PATENT NO. : 7,081,239 B2
APPLICATION NO. : 10/810020
DATED : July 25, 2006
INVENTOR(S) : Henry C. Lin It is certified that error appears in the above-identified patent and that said Letters Patent is hereby corrected as shown below:

Column 2, Line 25, delete "*entericfistulas*" and insert -- *enteric fistulas* --.

Signed and Sealed this

Twentieth Day of March, 2007

JON W. DUDAS
*Director of the United States Patent and Trademark Office*

UNITED STATES PATENT AND TRADEMARK OFFICE
CERTIFICATE OF CORRECTION

PATENT NO. : 7,081,239 B2 Page 1 of 1
APPLICATION NO. : 10/810020
DATED : July 25, 2006
INVENTOR(S) : Henry C. Lin It is certified that error appears in the above-identified patent and that said Letters Patent is hereby corrected as shown below:

In column 1, after the cross-reference to related applications but before the "Field of the Invention" section, please insert the following:

--FEDERAL SUPPORT
The U.S. Government has a paid-up license in this invention and the right in limited circumstances to require the patent owner to license others on reasonable terms as provided for by the terms of Grant No. DK046459 awarded by the National Institutes of Health.--

Signed and Sealed this
Twelfth Day of February, 2013

Teresa Stanek Rea
*Acting Director of the United States Patent and Trademark Office*